(12) United States Patent
Liu et al.

(10) Patent No.: US 11,008,339 B2
(45) Date of Patent: May 18, 2021

(54) SUBSTITUTED PYRAZOLE COMPOUNDS CONTAINING PYRIMIDINE AND PREPARATION METHOD AND USE THEREOF

(71) Applicant: Shenyang Sinochem Agrochemicals R&D Co., Ltd., Liaoning (CN)

(72) Inventors: Changling Liu, Liaoning (CN); Aiying Guan, Liaoning (CN); Junfeng Wang, Liaoning (CN); Xufeng Sun, Liaoning (CN); Zhinian Li, Liaoning (CN); Jinbo Zhang, Liaoning (CN); Lanfeng Ban, Liaoning (CN); Sen Ma, Liaoning (CN); Jie Lan, Liaoning (CN); Xiaoli Xia, Liaoning (CN); Jinlong Yang, Liaoning (CN)

(73) Assignee: Shenyang Sinochem Agrochemicals R&D Co., Ltd., Shenyang (CN)

( * ) Notice: Subject to any disclaimer, the term of this patent is extended or adjusted under 35 U.S.C. 154(b) by 54 days.

(21) Appl. No.: 15/568,561

(22) PCT Filed: May 17, 2016

(86) PCT No.: PCT/CN2016/082291
§ 371 (c)(1),
(2) Date: Oct. 23, 2017

(87) PCT Pub. No.: WO2016/184378
PCT Pub. Date: Nov. 24, 2016

(65) Prior Publication Data
US 2018/0141961 A1    May 24, 2018

(30) Foreign Application Priority Data

May 18, 2015 (CN) .......................... 201510252832.7

(51) Int. Cl.
| | | |
|---|---|---|
| C07D 513/04 | (2006.01) | |
| C07D 403/12 | (2006.01) | |
| A01N 43/54 | (2006.01) | |
| C07D 495/04 | (2006.01) | |
| C07D 417/14 | (2006.01) | |
| C07D 401/14 | (2006.01) | |
| A01N 43/56 | (2006.01) | |
| C07D 239/72 | (2006.01) | |
| C07D 403/14 | (2006.01) | |
| C07D 409/14 | (2006.01) | |
| C07D 487/04 | (2006.01) | |
| C07D 498/04 | (2006.01) | |

(52) U.S. Cl.
CPC .......... *C07D 513/04* (2013.01); *A01N 43/54* (2013.01); *A01N 43/56* (2013.01); *C07D 239/72* (2013.01); *C07D 401/14* (2013.01); *C07D 403/12* (2013.01); *C07D 403/14* (2013.01); *C07D 409/14* (2013.01); *C07D 417/14* (2013.01); *C07D 487/04* (2013.01); *C07D 495/04* (2013.01); *C07D 498/04* (2013.01)

(58) Field of Classification Search
CPC .. C07D 487/04; C07D 498/04; C07D 403/12; A01N 43/56; A01N 43/54
See application file for complete search history.

(56) References Cited

U.S. PATENT DOCUMENTS

| | | | | |
|---|---|---|---|---|
| 4,435,402 A | * | 3/1984 | Tsuji ...................... | A01N 43/54 514/256 |
| 6,054,592 A | * | 4/2000 | Muller .................. | A01N 47/24 548/371.1 |
| 6,518,266 B1 | * | 2/2003 | Dhanoa ................. | A01N 43/56 514/229.2 |

(Continued)

FOREIGN PATENT DOCUMENTS

| | | |
|---|---|---|
| CN | 104378986 A | 2/2015 |
| EP | 1329160 A2 | 7/2003 |

(Continued)

OTHER PUBLICATIONS

D.A. Williams et al., "Foye's Principles of Medicinal Chemistry," Fifth Edition, Copyright 2002 Lippincott Williams & Wilkins, pp. 37-67.*

(Continued)

*Primary Examiner* — Monica A Shin
(74) *Attorney, Agent, or Firm* — Suzannah K. Sundby, Esq.; Canady + Lortz LLP

(57) ABSTRACT

Disclosed are substituted pyrazole compounds containing pyrimidinyl as shown in Formula I:

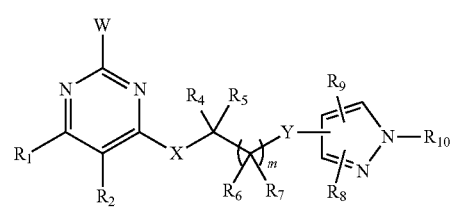

The definitions of each of the substituents can be seen in the description. The compounds of present invention have a good spectrum of bactericidal, insecticidal and acaricidal activity, and have good control effect on downy mildew of cucumber, powdery mildew of wheat, corn rust, rice blast, cucumber anthracnosis and the like. The compounds of present invention also show good insecticidal activity.

16 Claims, No Drawings

(56) References Cited

U.S. PATENT DOCUMENTS

2013/0288893 A1    10/2013   Buysse et al.

FOREIGN PATENT DOCUMENTS

| WO | 1995007278 A1 | 3/1995 | |
|---|---|---|---|
| WO | WO-9507278 A1 * | 3/1995 | ............. A01N 43/54 |

OTHER PUBLICATIONS

International Search Report received in PCT/CN2016/082291 dated Aug. 22, 2016.
Written Opinion received in PCT/CN2016/082291 dated Aug. 22, 2016.

* cited by examiner

SUBSTITUTED PYRAZOLE COMPOUNDS CONTAINING PYRIMIDINE AND PREPARATION METHOD AND USE THEREOF

FIELD OF THE INVENTION

The invention relates to fungicide, insecticide and acaricide. Specifically to the prepatation of a novel substituted pyrazole compounds containing pyrimidinyl and application thereof.

BACKGROUND OF THE INVENTION

Disclosed in Patent WO9507278 were the substituted pyrazole compounds containing pyrimidinyl having general formula and the specific compounds CK1 and CK2 applied as fungicide, insecticide and acaricide in agriculture.

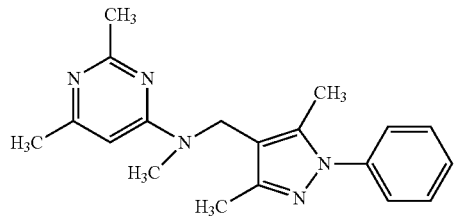

general formula

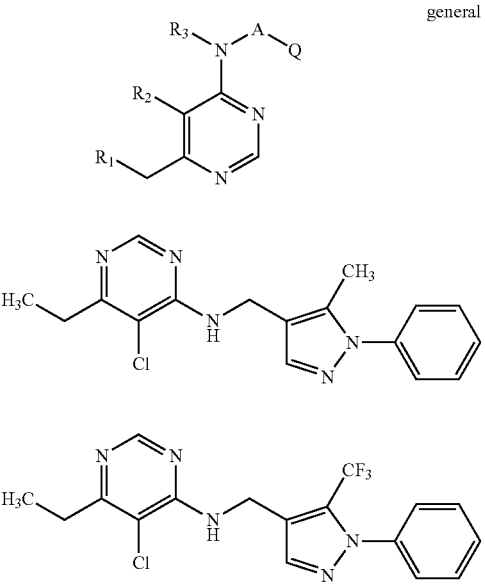

The following compounds CK3, CK4 and CK5 were retrieved via Scifinder database without specific literature disclosed.

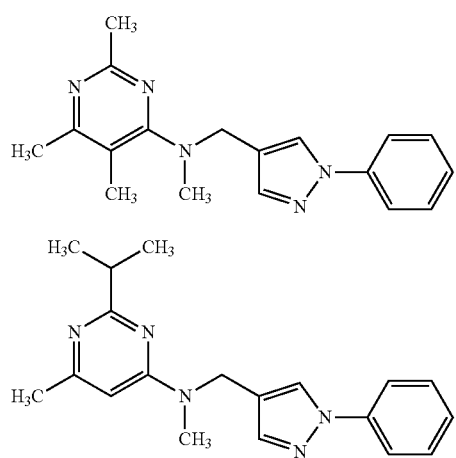

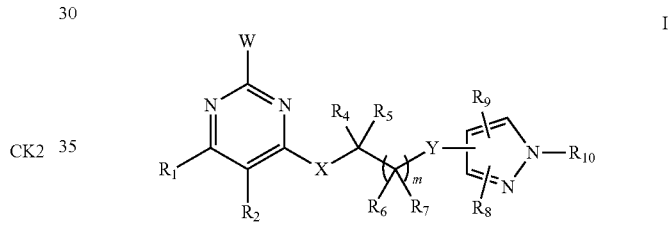

However, the substituted pyrazole compounds containing pyrimidinyl represented by general formula I of the present invention have not been reported in prior literatures.

SUMMARY OF THE INVENTION

The object of the present invention is to provide substituted pyrazole compounds containing pyrimidinyl and application thereof, which can be used to prepare fungicides, insecticides, and acaricides against harmful fungus, bacteria, insects and mites in agricultural or other fields.

In order to achieve the purpose above, the detailed descriptions of the invention are as follows:

The present invention provides a kind of substituted pyrazole compounds containing pyrimidinyl having a structure as represented by general formula I:

Wherein:

$R_1$ is selected from H, halogen, cyano, nitro, amino, carboxyl, $C_1$-$C_{12}$alkyl, halo$C_1$-$C_{12}$alkyl, $C_3$-$C_{12}$cycloalkyl, $C_1$-$C_{12}$alkoxy, halo$C_1$-$C_{12}$alkoxy, $C_1$-$C_{12}$alkylthio, halo$C_1$-$C_{12}$alkylthio, $C_1$-$C_{12}$alkylsulfinyl, $C_1$-$C_{12}$alkylsulfonyl, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_{12}$alkenoxy, halo$C_3$-$C_{12}$alkenoxy, $C_3$-$C_{12}$alkynoxy, halo$C_3$-$C_{12}$alkynoxy, $C_1$-$C_{12}$alkylamino, di($C_1$-$C_{12}$alkyl)amino, $C_1$-$C_{12}$alkylaminocarbonyl, halo$C_1$-$C_{12}$alkylaminocarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl or $C_1$-$C_{12}$alkylthio$C_1$-$C_{12}$alkyl;

$R_2$ is selected from H, halogen, cyano, nitro, amino, carboxyl, CHO, $C_1$-$C_{12}$alkyl, halo$C_1$-$C_{12}$alkyl, $C_1$-$C_{12}$alkoxy or halo$C_1$-$C_{12}$alkoxy;

$R_1$, $R_2$ and their conjoint pyrimidine ring can also form a five-membered ring, six-membered ring, seven-membered ring or eight-membered ring which contains carbon atom, nitrogen atom, oxygen atom or sulphur atom;

X is selected from $NR_3$, O or S;

Y is selected from $NR_3$, O or S;

$R_3$ is selected from H, OH, CHO, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, haloC$_1$-C$_{12}$alkylsulfinyl, C$_1$-C$_{12}$alkylsulfonyl, haloC$_1$-C$_{12}$alkylsulfonyl, C$_1$-C$_{12}$alkylaminosulfonyl, di(C$_1$-C$_{12}$alkyl)aminosulfonyl, C$_1$-C$_{12}$alkylsulfonylaminocarbonyl, C$_1$-C$_{12}$alkylcarbonylaminosulfonyl, C$_3$-C$_{12}$cycloalkyloxycarbonyl, C$_1$-C$_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkylcarbonylC$_1$-C$_{12}$alkyl, C$_1$-C$_{12}$alkoxycarbonylC$_1$-C$_{12}$alkyl, C$_1$-C$_{12}$alkylaminocarbonyl, di(C$_1$-C$_{12}$alkyl)aminocarbonyl, C$_2$-C$_{12}$alkenoxycarbonyl, C$_2$-C$_{12}$alkynoxycarbonyl, C$_1$-C$_{12}$alkoxyC$_1$-C$_{12}$alkoxycarbonyl, C$_1$-C$_{12}$alkylaminothio, di(C$_1$-C$_{12}$alkyl)aminothio, unsubstituted or further substituted (hetero)arylcarbonylC$_1$-C$_6$alkyl, (hetero)arylcarbonyl, (hetero)aryloxycarbonyl, (hetero)arylC$_1$-C$_6$alkyloxycarbonyl or (hetero)arylC$_1$-C$_6$alkyl by 1 to 5 following groups: halo, nitro, cyano, C$_1$-C$_6$alkyl, haloC$_1$-C$_6$alkyl, C$_1$-C$_6$alkoxy or haloC$_1$-C$_6$alkoxy;

R$_4$, R$_5$ may be the same or different, selected respectively from H, halogen, C$_1$-C$_{12}$alkyl, haloC$_1$-C$_{12}$alkyl, C$_1$-C$_{12}$alkoxy or haloC$_1$-C$_{12}$alkoxy; or R$_4$, R$_5$ and their conjoint carbon can also form a C$_3$-C$_8$ cycle;

R$_6$, R$_7$ may be the same or different, selected respectively from H, halogen, C$_1$-C$_{12}$alkyl, haloC$_1$-C$_{12}$alkyl, C$_1$-C$_{12}$alkoxy or haloC$_1$-C$_{12}$alkoxy; or R$_6$, R$_7$ and their conjoint carbon can also form a C$_3$-C$_8$ cycle;

The integer m is selected from 0 to 5;

R$_8$ is selected from H, cyano, halogen, C$_1$-C$_{12}$alkyl, haloC$_1$-C$_{12}$alkyl, C$_1$-C$_{12}$alkoxycarbonyl, haloC$_1$-C$_{12}$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 R$_{11}$;

R$_9$ is selected from H, cyano, halogen, C$_1$-C$_{12}$alkyl, haloC$_1$-C$_{12}$alkyl, C$_1$-C$_{12}$alkoxycarbonyl, haloC$_1$-C$_{12}$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 R$_{11}$;

R$_{10}$ is selected from C$_1$-C$_{12}$alkyl, C$_3$-C$_8$cycloalkyl, haloC$_1$-C$_{12}$alkyl, C$_1$-C$_{12}$alkylcarbonyl, haloC$_1$-C$_{12}$alkylcarbonyl, C$_1$-C$_{12}$alkylsulfonyl, haloC$_1$-C$_{12}$alkylsulfonyl, C$_1$-C$_{12}$alkoxycarbonyl, C$_1$-C$_{12}$alkoxyC$_1$-C$_{12}$alkyl, C$_1$-C$_{12}$alkoxycarbonylC$_1$-C$_{12}$alkyl, unsubstituted or further substituted (hetero)aryl, (hetero)arylmethyl, (hetero)arylcarbonyl, (hetero)arylmethylcarbonyl or (hetero) aryloxycarbonyl by 1 to 5 R$_{11}$;

R$_{11}$ is selected from halogen, OH, amino, cyano, nitro, C$_1$-C$_{12}$alkyl, haloC$_1$-C$_{12}$alkyl, C$_1$-C$_{12}$alkoxy, haloC$_1$-C$_{12}$alkoxy, C$_3$-C$_{12}$cycloalkyl, C$_1$-C$_{12}$alkylamino, haloC$_1$-C$_{12}$alkylamino, di(C$_1$-C$_{12}$alkyl)amino, halodi(C$_1$-C$_{12}$alkyl)amino, C(=O)NR$_{12}$R$_{13}$, C$_1$-C$_{12}$alkylthio, haloC$_1$-C$_{12}$alkylthio, C$_2$-C$_{12}$alkenyl, C$_2$-C$_{12}$alkynyl, C$_2$-C$_{12}$alkenoxy, haloC$_2$-C$_{12}$alkenoxy, C$_2$-C$_{12}$alkynoxy, haloC$_2$-C$_{12}$alkynoxy, C$_1$-C$_{12}$alkylsulfonyl, haloC$_1$-C$_{12}$alkylsulfonyl, C$_1$-C$_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkoxycarbonylC$_1$-C$_{12}$alkyl, haloC$_1$-C$_{12}$alkoxycarbonylC$_1$-C$_{12}$alkyl, C$_1$-C$_{12}$alkylthiocarbonylC$_1$-C$_{12}$alkyl, haloC$_1$-C$_{12}$alkylthiocarbonylC$_1$-C$_{12}$alkyl, C$_1$-C$_{12}$alkylcarbonyloxy, haloC$_1$-C$_{12}$alkylcarbonyloxy, C$_1$-C$_{12}$alkoxycarbonyloxy, haloC$_1$-C$_{12}$alkoxycarbonyloxy, C$_1$-C$_{12}$alkylsulfonyloxy, haloC$_1$-C$_{12}$alkylsulfonyloxy, C$_1$-C$_{12}$alkoxyC$_1$-C$_{12}$alkoxy or haloC$_1$-C$_{12}$alkoxyC$_1$-C$_{12}$alkoxy;

R$_{12}$, R$_{13}$ may be the same or different, selected respectively from H, C$_1$-C$_{12}$alkyl or haloC$_1$-C$_{12}$alkyl;

W is selected from H, halogen, C$_1$-C$_{12}$alkyl, haloC$_1$-C$_{12}$alkyl, C$_3$-C$_8$cycloalkyl, C$_1$-C$_{12}$alkoxy, C$_1$-C$_{12}$alkylthio or C$_1$-C$_{12}$alkylsulfonyl;

The position of Y linked to pyrazole ring is from 3-position, 4-position or 5-position. When Y is linked to 3-position of pyrazole, R$_8$ is at the 4-position, R$_9$ is at the 5-position; When Y is linked to 4-position of pyrazole, R$_8$ is at the 3-position, R$_9$ is at the 5-position; When Y is linked to 5-position of pyrazole, R$_8$ is at the 3-position, R$_9$ is at the 4-position;

Or the salts formed from the compounds represented by general formula I.

In the substituted pyrazole compounds containing pyrimidinyl of this invention, the preferred compounds include: in general formula I:

R$_1$ is selected from H, halogen, cyano, nitro, amino, carboxyl, C$_1$-C$_6$alkyl, haloC$_1$-C$_6$alkyl, C$_3$-C$_6$cycloalkyl, C$_1$-C$_6$alkoxy, haloC$_1$-C$_6$alkoxy, C$_1$-C$_6$alkylthio, C$_1$-C$_6$alkylsulfinyl, C$_1$-C$_6$alkylsulfonyl, haloC$_1$-C$_6$alkylthio, C$_2$-C$_6$alkenyl, haloC$_2$-C$_6$alkenyl, C$_2$-C$_6$alkynyl, haloC$_2$-C$_6$alkynyl, C$_3$-C$_6$alkenoxy, haloC$_3$-C$_6$alkenoxy, C$_3$-C$_6$alkynoxy, haloC$_3$-C$_6$alkynoxy, C$_1$-C$_6$alkylamino, di(C$_1$-C$_6$alkyl)amino, C$_1$-C$_6$alkylaminocarbonyl, haloC$_1$-C$_6$alkylaminocarbonyl, C$_1$-C$_6$alkoxycarbonyl, haloC$_1$-C$_6$alkoxycarbonyl, C$_1$-C$_6$alkoxyC$_1$-C$_6$alkyl or C$_1$-C$_6$alkylthioC$_1$-C$_6$alkyl;

R$_2$ is selected from H, halogen, cyano, nitro, amino, carboxyl, CHO, C$_1$-C$_6$alkyl, haloC$_1$-C$_6$alkyl, C$_1$-C$_6$alkoxy or haloC$_1$-C$_6$alkoxy;

R$_1$, R$_2$ and their conjoint pyrimidine ring can also form a five-membered ring or six-membered ring which contains carbon atom, nitrogen atom, oxygen atom or sulphur atom;

X is selected from NR$_3$, O or S;

Y is selected from NR$_3$, O or S;

R$_3$ is selected from H, OH, CHO, C$_1$-C$_6$alkyl, haloC$_1$-C$_6$alkyl, C$_1$-C$_6$alkoxy, haloC$_1$-C$_6$alkoxy, C$_3$-C$_6$cycloalkyl, C$_1$-C$_6$alkylthio, C$_2$-C$_6$alkenylthio, C$_2$-C$_6$alkenyl, C$_2$-C$_6$alkynyl, haloC$_2$-C$_6$alkenyl, haloC$_2$-C$_6$alkynyl, C$_1$-C$_6$alkoxyC$_1$-C$_6$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkylsulfinyl, haloC$_1$-C$_6$alkylsulfinyl, C$_1$-C$_6$alkylsulfonyl, haloC$_1$-C$_6$alkylsulfonyl, C$_1$-C$_6$alkylaminosulfonyl, di(C$_1$-C$_6$alkyl)aminosulfonyl, C$_1$-C$_6$alkylsulfonylaminocarbonyl, C$_1$-C$_6$alkylcarbonylaminosulfonyl, C$_3$-C$_6$cycloalkyloxycarbonyl, C$_1$-C$_6$alkylcarbonyl, haloC$_1$-C$_6$alkylcarbonyl, C$_1$-C$_6$alkoxycarbonyl, haloC$_1$-C$_6$alkoxycarbonyl, C$_1$-C$_6$alkylcarbonylC$_1$-C$_6$alkyl, C$_1$-C$_6$alkoxycarbonylC$_1$-C$_6$alkyl, C$_1$-C$_6$alkylaminocarbonyl, di(C$_1$-C$_6$alkyl)aminocarbonyl, C$_2$-C$_6$alkenoxycarbonyl, C$_2$-C$_6$alkynoxycarbonyl, C$_1$-C$_6$alkoxyC$_1$-C$_6$alkoxycarbonyl, C$_1$-C$_6$alkylaminothio, di(C$_1$-C$_6$alkyl)aminothio, unsubstituted or further substituted (hetero)arylcarbonyl C$_1$-C$_6$alkyl, (hetero)arylcarbonyl, (hetero)aryloxycarbonyl, (hetero)arylC$_1$-C$_6$alkyloxycarbonyl or (hetero)arylC$_1$-C$_6$alkyl by 1 to 5 following groups: halogen, nitro, cyano, C$_1$-C$_6$alkyl, haloC$_1$-C$_6$alkyl, C$_1$-C$_6$alkoxy or haloC$_1$-C$_6$alkoxy;

R$_4$, R$_5$ may be the same or different, selected respectively from H, halogen, C$_1$-C$_6$alkyl, haloC$_1$-C$_6$alkyl, C$_1$-C$_6$alkoxy or haloC$_1$-C$_6$alkoxy; or R$_4$, R$_5$ and their conjoint carbon can also form a C$_3$-C$_6$ cycle;

$R_6$, $R_7$ may be the same or different, selected respectively from H, halogen, $C_1$-$C_6$alkyl, halo$C_1$-$C_6$alkyl, $C_1$-$C_6$alkoxy or halo$C_1$-$C_6$alkoxy; or $R_6$, $R_7$ and their conjoint carbon can also form a $C_3$-$C_6$ cycle;

The integer m is selected from 0 to 4;

$R_8$ is selected from H, cyano, halogen, $C_1$-$C_6$alkyl, halo$C_1$-$C_6$alkyl, $C_1$-$C_6$alkoxycarbonyl, halo$C_1$-$C_6$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_9$ is selected from H, cyano, halogen, $C_1$-$C_6$alkyl, halo$C_1$-$C_6$alkyl, $C_1$-$C_6$alkoxycarbonyl, halo$C_1$-$C_6$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{10}$ is selected from $C_1$-$C_6$alkyl, $C_3$-$C_6$cycloalkyl, halo$C_1$-$C_6$alkyl, $C_1$-$C_6$alkylcarbonyl, halo$C_1$-$C_6$alkylcarbonyl, $C_1$-$C_6$alkylsulfonyl, halo$C_1$-$C_6$alkylsulfonyl, $C_1$-$C_6$alkoxycarbonyl, $C_1$-$C_6$alkoxyC$_1$-$C_6$alkyl, $C_1$-$C_6$alkoxycarbonylC$_1$-$C_6$alkyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{11}$ is selected from halogen, OH, amino, cyano, nitro, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_1$-$C_6$alkylamino, halo$C_1$-$C_6$alkylamino, di($C_1$-$C_6$alkyl)amino, halodi($C_1$-$C_6$alkyl)amino, C(=O)NR$_{12}$R$_{13}$, $C_1$-$C_6$alkylthio, halo$C_1$-$C_6$alkylthio, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylsulfonyl, halo$C_1$-$C_6$alkylsulfonyl, $C_1$-$C_6$alkylcarbonyl, halo$C_1$-$C_6$alkylcarbonyl, $C_1$-$C_6$alkoxycarbonyl, halo$C_1$-$C_6$alkoxycarbonyl, $C_1$-$C_6$alkoxyC$_1$-$C_6$alkyl, halo$C_1$-$C_6$alkoxyC$_1$-$C_6$alkyl, $C_1$-$C_6$alkylthioC$_1$-$C_6$alkyl, halo$C_1$-$C_6$alkylthioC$_1$-$C_6$alkyl, $C_1$-$C_6$alkoxycarbonylC$_1$-$C_6$alkyl, halo$C_1$-$C_6$alkoxycarbonylC$_1$-$C_6$alkyl, $C_1$-$C_6$alkylthiocarbonylC$_1$-$C_6$alkyl, halo$C_1$-$C_6$alkylthiocarbonylC$_1$-$C_6$alkyl, $C_1$-$C_6$alkylcarbonyloxy, halo$C_1$-$C_6$alkylcarbonyloxy, $C_1$-$C_6$alkoxycarbonyloxy, halo$C_1$-$C_6$alkoxycarbonyloxy, $C_1$-$C_6$alkylsulfonyloxy, halo$C_1$-$C_6$alkylsulfonyloxy, $C_1$-$C_6$alkoxyC$_1$-$C_6$alkoxy or halo$C_1$-$C_6$alkoxyC$_1$-$C_6$alkoxy;

$R_{12}$, $R_{13}$ may be the same or different, selected respectively from H, $C_1$-$C_6$alkyl or halo$C_1$-$C_6$alkyl;

W is selected from H, halogen, $C_1$-$C_6$alkyl, halo$C_1$-$C_6$alkyl, $C_3$-$C_6$cycloalkyl, $C_1$-$C_6$alkoxy, $C_1$-$C_6$alkylthio or $C_1$-$C_6$alkylsulfonyl;

The position of Y linked to pyrazole ring is from 3-position, 4-position or 5-position. When Y is linked to 3-position of pyrazole, $R_8$ is at the 4-position, $R_9$ is at the 5-position; When Y is linked to 4-position of pyrazole, $R_8$ is at the 3-position, $R_9$ is at the 5-position; When Y is linked to 5-position of pyrazole, $R_8$ is at the 3-position, $R_9$ is at the 4-position;

Or the salts formed from the preferred compounds represented by general formula I above.

In the substituted pyrazole compounds containing pyrimidinyl of this invention, the more preferred compounds include: in general formula I:

$R_1$ is selected from H, halogen, cyano, nitro, amino, carboxyl, $C_1$-$C_4$alkyl, halo$C_1$-$C_4$alkyl, $C_3$-$C_4$cycloalkyl, $C_1$-$C_4$alkoxy, halo$C_1$-$C_4$alkoxy, $C_1$-$C_4$alkylthio, $C_1$-$C_4$alkylsulfinyl, $C_1$-$C_4$alkylsulfonyl, halo$C_1$-$C_4$alkylthio, $C_2$-$C_4$alkenyl, halo$C_2$-$C_4$alkenyl, $C_2$-$C_4$alkynyl, halo$C_2$-$C_4$alkynyl, $C_3$-$C_4$alkenoxy, halo$C_3$-$C_4$alkenoxy, $C_3$-$C_4$alkynoxy, halo$C_3$-$C_4$alkynoxy, $C_1$-$C_4$alkylamino, di($C_1$-$C_4$alkyl)amino, $C_1$-$C_4$alkylaminocarbonyl, halo$C_1$-$C_4$alkylaminocarbonyl, $C_1$-$C_4$alkoxycarbonyl, halo$C_1$-$C_4$alkoxycarbonyl, $C_1$-$C_4$alkoxyC$_1$-$C_4$alkyl or $C_1$-$C_4$alkylthioC$_1$-$C_4$alkyl;

$R_2$ is selected from H, halogen, cyano, nitro, amino, carboxyl, CHO, $C_1$-$C_4$alkyl, halo$C_1$-$C_4$alkyl, $C_1$-$C_4$alkoxy or halo$C_1$-$C_4$alkoxy;

$R_1$, $R_2$ and their conjoint pyrimidine ring can also form a five-membered ring or six-membered ring which contains carbon atom, nitrogen atom, oxygen atom or sulphur atom;

X is selected from NR$_3$, O or S;

$R_3$ is selected from H, OH, CHO, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylthio, $C_2$-$C_4$alkenylthio, $C_2$-$C_4$alkenyl, $C_2$-$C_4$alkynyl, halo$C_2$-$C_4$alkenyl, halo$C_2$-$C_4$alkynyl, $C_1$-$C_4$alkoxyC$_1$-$C_4$alkyl, halo$C_1$-$C_4$alkoxyC$_1$-$C_4$alkyl, $C_1$-$C_4$alkylthioC$_1$-$C_4$alkyl, halo$C_1$-$C_4$alkylthioC$_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, di($C_1$-$C_4$alkyl)aminosulfonyl, $C_1$-$C_4$alkylsulfonylaminocarbonyl, $C_1$-$C_4$alkylcarbonylaminosulfonyl, $C_3$-$C_4$cycloalkyloxycarbonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkylcarbonylC$_1$-$C_4$alkyl, $C_1$-$C_4$alkoxycarbonylC$_1$-$C_4$alkyl, $C_1$-$C_4$alkylaminocarbonyl, di($C_1$-$C_4$alkyl)aminocarbonyl, $C_2$-$C_4$alkenoxycarbonyl, $C_2$-$C_4$alkynoxycarbonyl, $C_1$-$C_4$alkoxyC$_1$-$C_4$alkoxycarbonyl, $C_1$-$C_4$alkylaminothio, di($C_1$-$C_4$alkyl)aminothio, unsubstituted or further substituted (hetero)arylcarbonyl C$_1$-$C_4$alkyl, (hetero)arylcarbonyl, (hetero)aryloxycarbonyl, (hetero)arylC$_1$-$C_4$alkyloxycarbonyl or (hetero)arylC$_1$-$C_4$alkyl by 1 to 5 following groups: halogen, nitro, cyano, $C_1$-$C_4$alkyl, halo$C_1$-$C_4$alkyl, $C_1$-$C_4$alkoxy or halo$C_1$-$C_4$alkoxy;

$R_4$, $R_5$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy; or $R_4$, $R_5$ and their conjoint carbon can also form a $C_3$-$C_4$ cycle;

$R_6$, $R_7$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy; or $R_6$, $R_7$ and their conjoint carbon can also form a $C_3$-$C_4$ cycle;

The integer m is selected from 0 to 3;

$R_8$ is selected from H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_9$ is selected from H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_{10}$ is selected from $C_1$-$C_4$alkyl, $C_3$-$C_4$cycloalkyl, halo$C_1$-$C_4$alkyl, $C_1$-$C_4$alkylcarbonyl, halo$C_1$-$C_4$alkylcarbonyl, $C_1$-$C_4$alkylsulfonyl, halo$C_1$-$C_4$alkylsulfonyl, $C_1$-$C_4$alkoxycarbonyl, $C_1$-$C_4$alkoxyC$_1$-$C_4$alkyl, $C_1$-$C_4$alkoxycarbonylC$_1$-$C_4$alkyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_{11}$ is selected from halogen, OH, amino, cyano, nitro, $C_1$-$C_4$alkyl, halo$C_1$-$C_4$alkyl, $C_1$-$C_4$alkoxy, halo$C_1$-

$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, C(=O)N$R_{12}R_{13}$, $C_1$-$C_4$alkylthio, halo$C_1$-$C_4$alkylthio, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkyl sulfonyl, halo$C_1$-$C_4$alkyl sulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkoxycarbonyl$C_1$-$C_4$alkyl, halo$C_1$-$C_4$alkoxycarbonyl$C_1$-$C_4$alkyl, $C_1$-$C_4$alkylthiocarbonyl$C_1$-$C_4$alkyl, halo$C_1$-$C_4$alkylthiocarbonyl$C_1$-$C_4$alkyl, $C_1$-$C_4$alkylcarbonyloxy, halo$C_1$-$C_4$alkylcarbonyloxy, $C_1$-$C_4$alkoxycarbonyloxy, halo$C_1$-$C_4$alkoxycarbonyloxy, $C_1$-$C_4$alkylsulfonyloxy, halo$C_1$-$C_4$alkylsulfonyloxy, $C_1$-$C_4$alkoxy$C_1$-$C_4$alkoxy or halo$C_1$-$C_4$alkoxy$C_1$-$C_4$alkoxy;

$R_{12}$, $R_{13}$ may be the same or different, selected respectively from H, $C_1$-$C_4$alkyl or halo$C_1$-$C_4$alkyl;

W is selected from H, halogen, $C_1$-$C_4$alkyl, halo$C_1$-$C_4$alkyl, $C_3$-$C_4$cycloalkyl, $C_1$-$C_4$alkoxy, $C_1$-$C_4$alkylthio or $C_1$-$C_4$alkylsulfonyl;

Y is O, the position of Y linked to pyrazole ring is from 3-position, 4-position or 5-position. When O is linked to 3-position of pyrazole, $R_8$ is at the 4-position, $R_9$ is at the 5-position, general formula I is represented by general formula I-1; When Y is linked to 4-position of pyrazole, $R_8$ is at the 3-position, $R_9$ is at the 5-position, general formula I is represented by general formula I-2; When Y is linked to 5-position of pyrazole, $R_8$ is at the 3-position, $R_9$ is at the 4-position, general formula I is represented by general formula I-3;

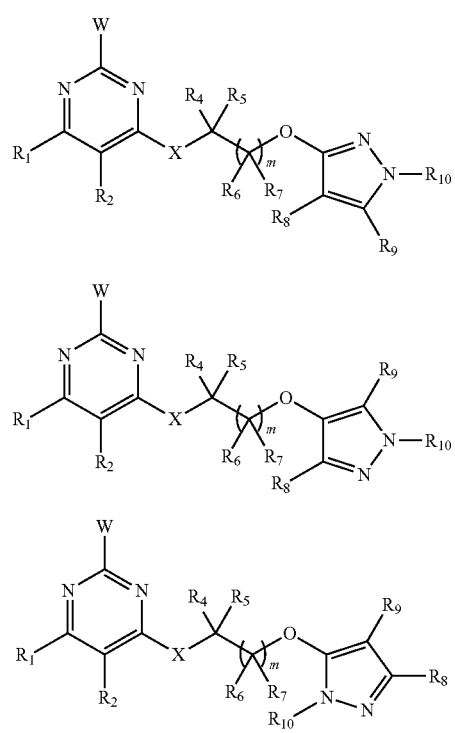

Or the salts formed from the more preferred compounds represented by general formula I above.

In the substituted pyrazole compounds containing pyrimidinyl of this invention, the more preferred compounds include: in general formula I:

the structures of compounds of general formula I-1 are represented by general formula I-1A, I-1B, I-1C, I-1D, I-1E, I-1F, I-1G, I-1H, I-1I, I-1J, I-1K, I-1L, I-1M, I-1N, I-4C, I-4F or I-4G;

the structures of compounds of general formula I-2 are represented by general formula I-2A, I-2B, I-2C, I-2D, I-2E, I-2F or I-2G;

the structures of compounds of general formula I-3 are represented by general formula I-3A, I-3B, I-3C, I-3D, I-3E, I-3F or I-3G:

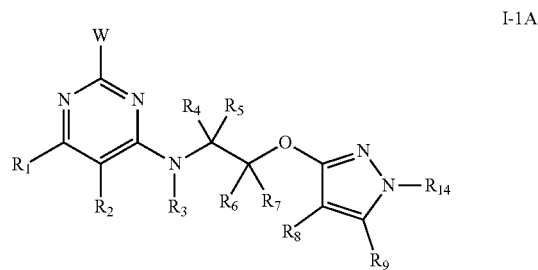

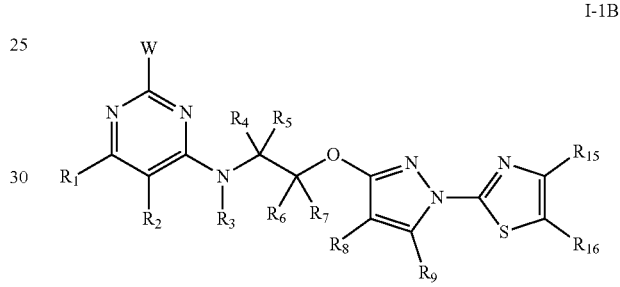

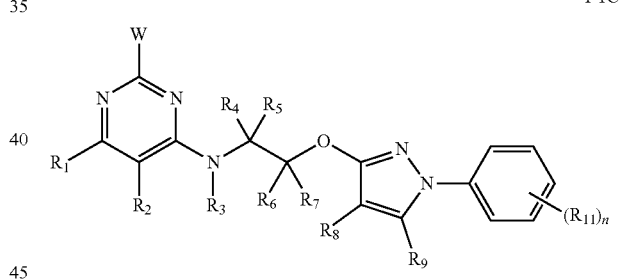

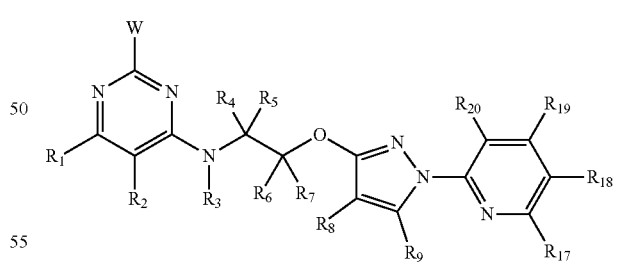

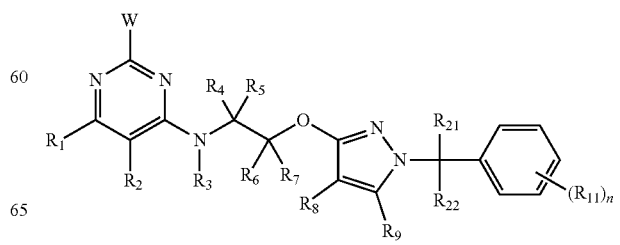

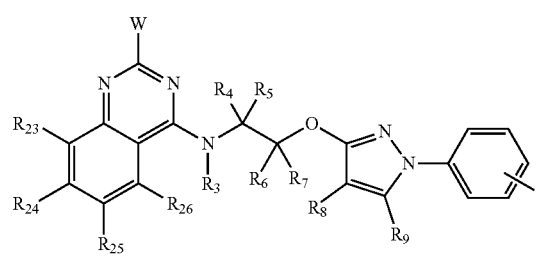
I-1F
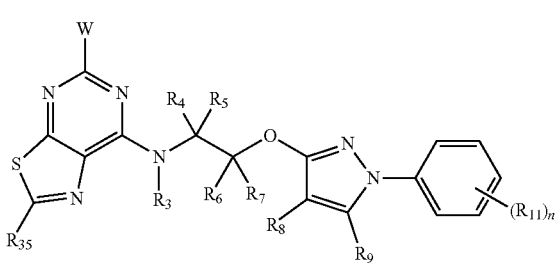
I-1L
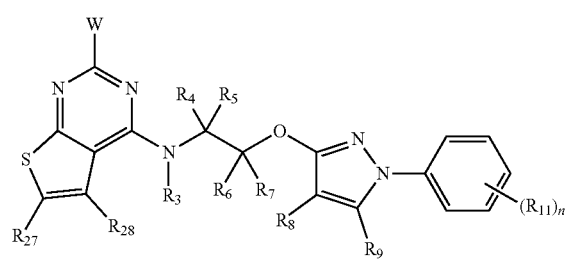
I-1G
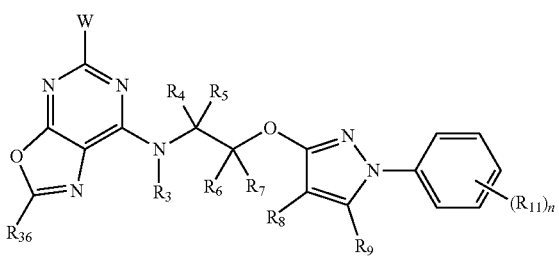
I-1M
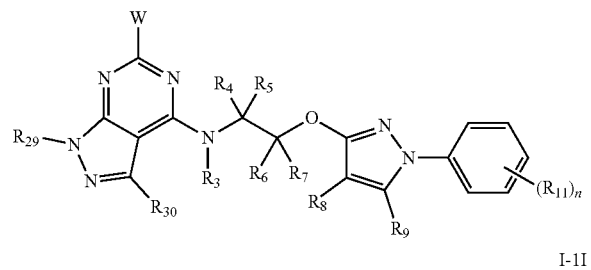
I-1H
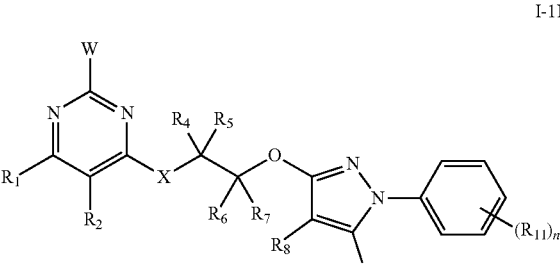
I-1N
(X = O or S)
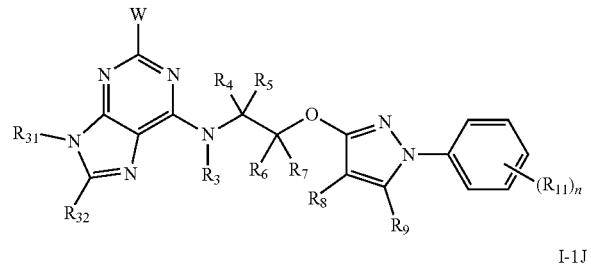
I-1I
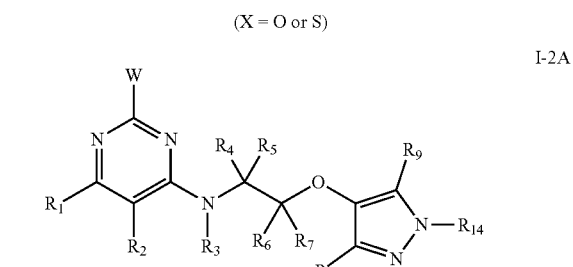
I-2A
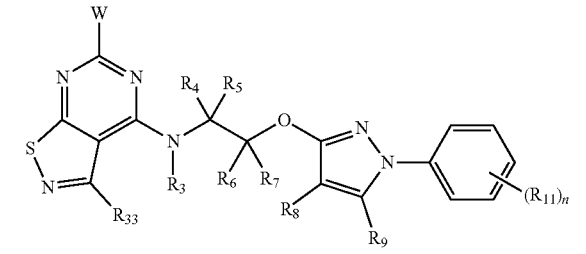
I-1J
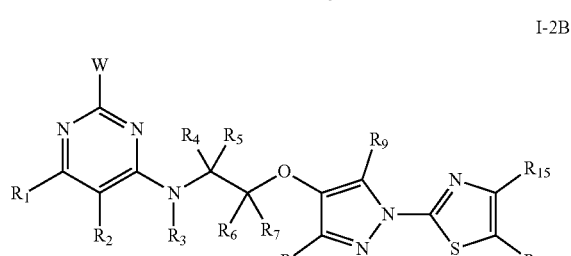
I-2B
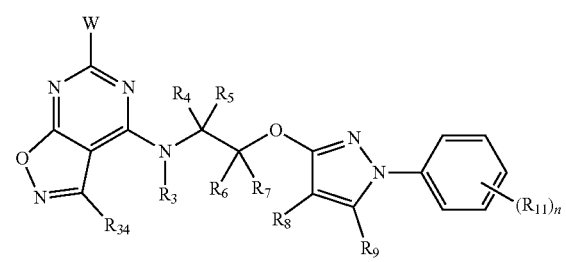
I-1K
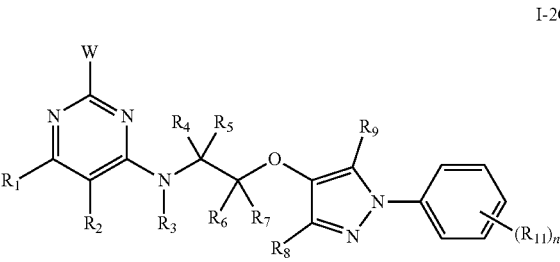
I-2C I-2D
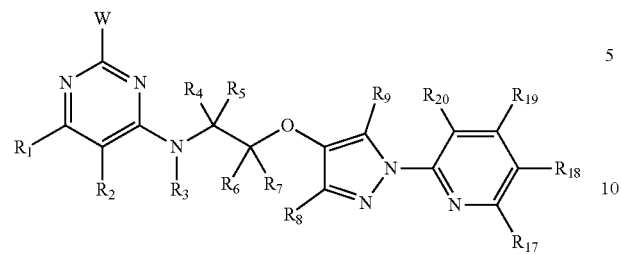
I-2E
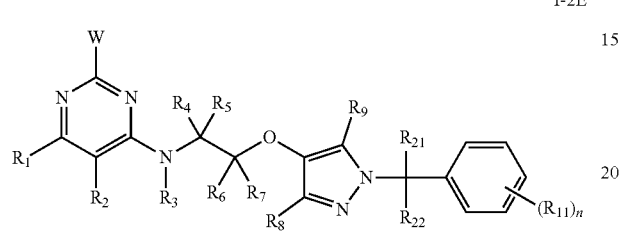
I-2F
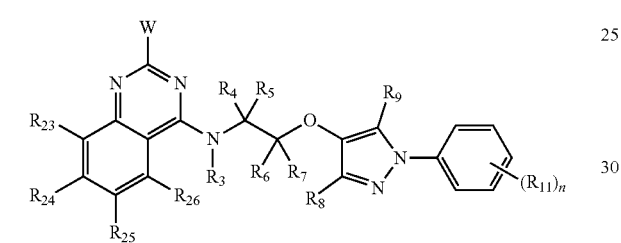
I-2G
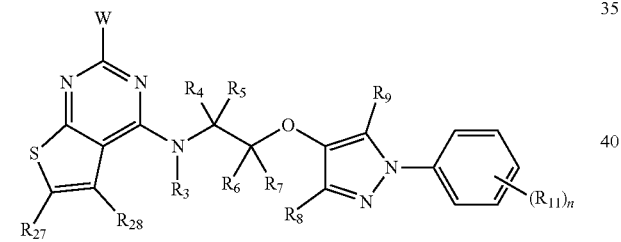
I-3A
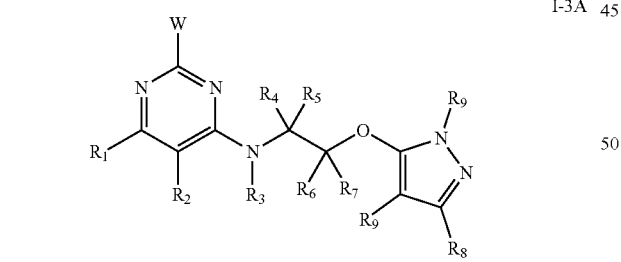
I-3B
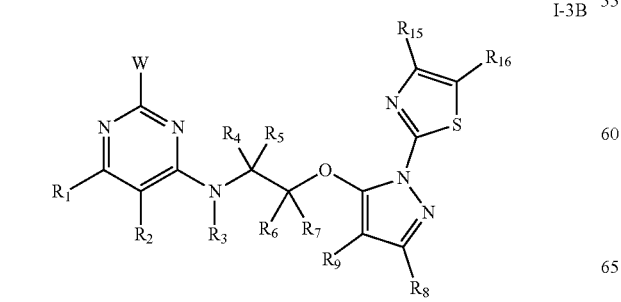
I-3C
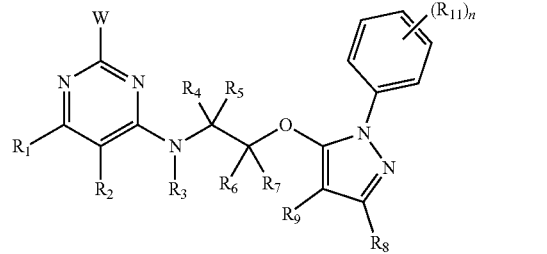
I-3D
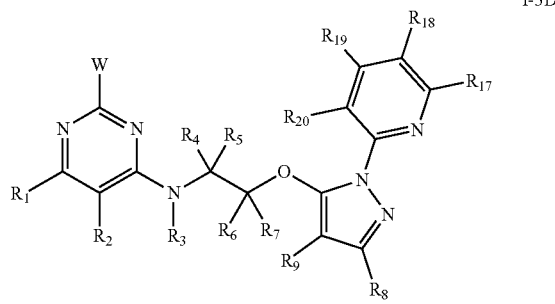
I-3E
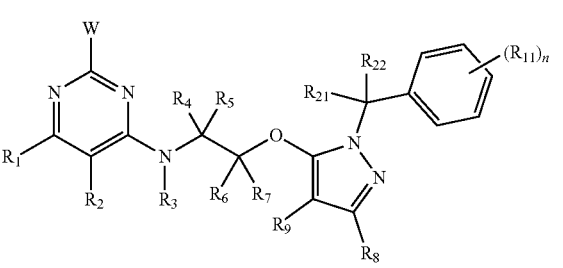
I-3F
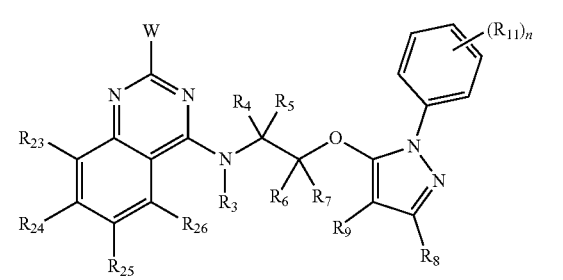
I-3G
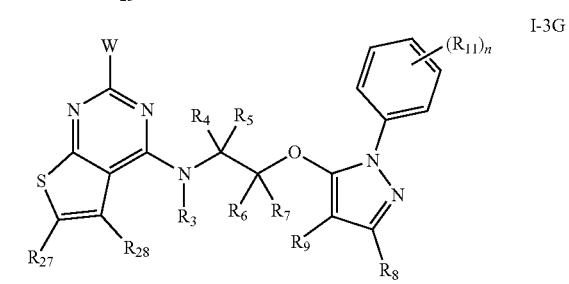
I-4C
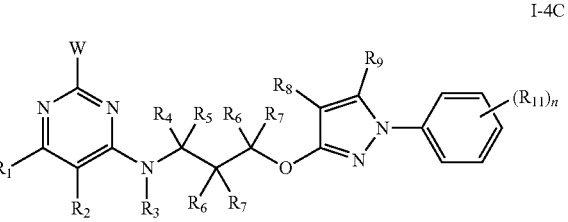

-continued

I-4F

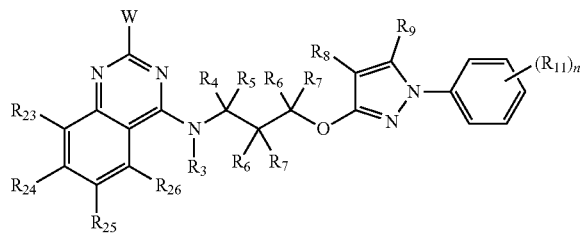

I-4G

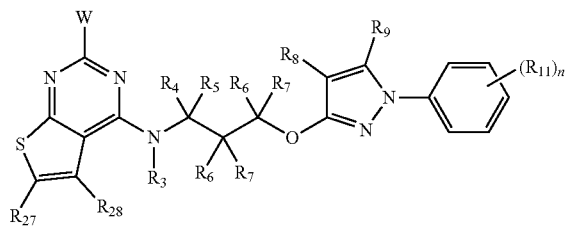

In general formula I-1A, I-1B, I-1C, I-1D, I-1E, I-1F, I-1G, I-1H, I-1I, I-1J, I-1K, I-1L, I-1M, I-1N, I-4C, I-4F, I-4G, I-2A, I-2B, I-2C, I-2D, I-2E, I-2F, I-2G, I-3A, I-3B, I-3C, I-3D, I-3E, I-3F and I-3G, Wherein:

$R_1$ is selected from H, halogen, cyano, nitro, amino, carboxyl, $C_1$-$C_4$alkyl, halo$C_1$-$C_4$alkyl, $C_3$-$C_4$cycloalkyl, $C_1$-$C_4$alkoxy, halo$C_1$-$C_4$alkoxy, $C_1$-$C_4$alkylthio, halo$C_1$-$C_4$alkylthio, $C_1$-$C_4$alkylsulfinyl, $C_1$-$C_4$alkylsulfonyl, $C_2$-$C_4$alkenyl, halo$C_2$-$C_4$alkenyl, $C_2$-$C_4$alkynyl, halo$C_2$-$C_4$alkynyl, $C_3$-$C_4$alkenoxy, halo$C_3$-$C_4$alkenoxy, $C_3$-$C_4$alkynoxy, halo$C_3$-$C_4$alkynoxy, $C_1$-$C_4$alkylamino, di($C_1$-$C_4$alkyl)amino, $C_1$-$C_4$alkylaminocarbonyl, halo$C_1$-$C_4$alkylaminocarbonyl, $C_1$-$C_4$alkoxycarbonyl, halo$C_1$-$C_4$alkoxycarbonyl, $C_1$-$C_4$alkoxy$C_1$-$C_4$alkyl or $C_1$-$C_4$alkylthio$C_1$-$C_4$alkyl;

$R_2$ is selected from H, halogen, cyano, nitro, amino, carboxyl, CHO, $C_1$-$C_4$alkyl, halo$C_1$-$C_4$alkyl, $C_1$-$C_4$alkoxy or halo$C_1$-$C_4$alkoxy;

$R_3$ is selected from H, OH, CHO, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylthio, $C_2$-$C_4$alkenylthio, $C_2$-$C_4$alkenyl, $C_2$-$C_4$alkynyl, halo$C_2$-$C_4$alkenyl, halo$C_2$-$C_4$alkynyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, di($C_1$-$C_4$alkyl)aminosulfonyl, $C_1$-$C_4$alkylsulfonylaminocarbonyl, $C_1$-$C_4$alkylcarbonylaminosulfonyl, $C_3$-$C_4$cycloalkyloxycarbonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkylcarbonyl$C_1$-$C_4$alkyl, $C_1$-$C_4$alkoxycarbonyl$C_1$-$C_4$alkyl, $C_1$-$C_4$alkylaminocarbonyl, di($C_1$-$C_4$alkyl)aminocarbonyl, $C_2$-$C_4$alkenoxycarbonyl, $C_2$-$C_4$alkynoxycarbonyl, $C_1$-$C_4$alkoxy$C_1$-$C_4$alkoxycarbonyl, $C_1$-$C_4$alkylaminothio, di($C_1$-$C_4$alkyl)aminothio, unsubstituted or further substituted (hetero)arylcarbonyl $C_1$-$C_4$alkyl, (hetero)arylcarbonyl, (hetero)aryloxycarbonyl, (hetero)aryl$C_1$-$C_4$alkyloxycarbonyl or (hetero)aryl$C_1$-$C_4$alkyl by 1 to 5 following groups: halogen, nitro, cyano, $C_1$-$C_4$alkyl, halo$C_1$-$C_4$alkyl, $C_1$-$C_4$alkoxy or halo$C_1$-$C_4$alkoxy;

$R_4$, $R_5$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy; or $R_4$, $R_5$ and their conjoint carbon can also form a $C_3$-$C_4$ cycle;

$R_6$, $R_7$ may be the same or different, selected respectively from H, halogen, $C_1$-$C_4$alkyl, halo$C_1$-$C_4$alkyl, $C_1$-$C_4$alkoxy or halo$C_1$-$C_4$alkoxy; or $R_6$, $R_7$ and their conjoint carbon can also form a $C_3$-$C_4$ cycle;

$R_8$ is selected from H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_9$ is selected from H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_{11}$ is selected from halogen, OH, amino, cyano, nitro, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, $C(=O)NR_{12}R_{13}$, $C_1$-$C_4$alkylthio, halo$C_1$-$C_4$alkylthio, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkoxycarbonyl$C_1$-$C_4$alkyl, halo$C_1$-$C_4$alkoxycarbonyl$C_1$-$C_4$alkyl, $C_1$-$C_4$alkylthiocarbonyl$C_1$-$C_4$alkyl, halo$C_1$-$C_4$alkylthiocarbonyl$C_1$-$C_4$alkyl, $C_1$-$C_4$alkylcarbonyloxy, halo$C_1$-$C_4$alkylcarbonyloxy, $C_1$-$C_4$alkoxycarbonyloxy, halo$C_1$-$C_4$alkoxycarbonyloxy, $C_1$-$C_4$alkylsulfonyloxy, halo$C_1$-$C_4$alkylsulfonyloxy, $C_1$-$C_4$alkoxy$C_1$-$C_4$alkoxy or halo$C_1$-$C_4$alkoxy$C_1$-$C_4$alkoxy;

The integer n is selected from 0 to 5, when n is 0, the benzene ring is unsubstituted phenyl; when n is more than 1, $R_{11}$ may be the same or different;

$R_{12}$, $R_{13}$ may be the same or different, selected respectively from H, $C_1$-$C_4$alkyl or halo$C_1$-$C_4$alkyl;

$R_{14}$ is selected from $C_1$-$C_4$alkyl, $C_3$-$C_4$cycloalkyl, halo$C_1$-$C_4$alkyl, $C_1$-$C_4$alkylcarbonyl, halo$C_1$-$C_4$alkylcarbonyl, $C_1$-$C_4$alkylsulfonyl, halo$C_1$-$C_4$alkylsulfonyl, $C_1$-$C_4$alkoxycarbonyl, $C_1$-$C_4$alkoxy$C_1$-$C_4$alkyl or $C_1$-$C_4$alkoxycarbonyl$C_1$-$C_4$alkyl;

$R_{15}$, $R_{16}$ may be the same or different, selected respectively from H, halogen, amino, cyano, nitro, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo $C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{17}$, $R_{18}$, $R_{19}$, $R_{20}$ may be the same or different, selected respectively from H, halogen, cyano, nitro, $C_1$-$C_4$alkyl, halo$C_1$-$C_4$alkyl, $C_1$-$C_4$alkoxy or halo$C_1$-$C_4$alkoxy;

$R_{21}$, $R_{22}$ may be the same or different, selected respectively from H, halogen, OH, cyano, nitro, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{23}$, $R_{24}$, $R_{25}$, $R_{26}$ may be the same or different, selected respectively from H, halogen, OH, amino, cyano, nitro, $C_1$-$C_4$alkyl, halo$C_1$-$C_4$alkyl, $C_1$-$C_4$alkoxy, halo$C_1$-$C_4$alkoxy or $C_3$-$C_4$cycloalkyl;

$R_{27}$, $R_{28}$ may be the same or different, selected respectively from H, halogen, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl or (hetero)aryloxycarbonyl by 1 to 5 $R_{11}$;

$R_{29}$ is selected from $C_1$-$C_4$alkyl, halo$C_1$-$C_4$alkyl, $C_3$-$C_4$cycloalkyl, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{30}$ is selected from H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero) arylmethylcarbonyl or (hetero) aryloxycarbonyl by 1 to 5 $R_{11}$;

$R_{31}$ is selected from $C_1$-$C_4$alkyl, halo$C_1$-$C_4$alkyl, $C_3$-$C_4$cycloalkyl, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{32}$ is selected from H, cyano, halogen, $C_1$-$C_4$alkyl, halo$C_1$-$C_4$alkyl, unsubstituted or further substituted (hetero) aryl, (hetero)arylmethyl, (hetero)arylcarbonyl, (hetero)arylmethylcarbonyl or (hetero) aryloxycarbonyl by 1 to 5 $R_{11}$;

$R_{33}$, $R_{34}$ may be selected respectively from $C_1$-$C_4$alkyl, halo$C_1$-$C_4$alkyl, $C_3$-$C_4$cycloalkyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero) arylmethylcarbonyl or (hetero) aryloxycarbonyl by 1 to 5 $R_{11}$;

$R_{35}$, $R_{36}$ may be selected respectively from H, cyano, halogen, $C_1$-$C_4$alkyl, halo$C_1$-$C_4$alkyl, unsubstituted or further substituted (hetero)aryl, (hetero)arylmethyl, (hetero) arylcarbonyl, (hetero)arylmethylcarbonyl or (hetero) aryloxycarbonyl by 1 to 5 $R_{11}$;

W is selected from H, halogen, $C_1$-$C_4$alkyl, halo$C_1$-$C_4$alkyl, $C_3$-$C_4$cycloalkyl, $C_1$-$C_4$alkoxy, halo$C_1$-$C_4$alkoxy or $C_1$-$C_4$alkylsulfonyl;

Or the salts formed from the more preferred compounds represented by general formula above, with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid or citric acid.

In the substituted pyrazole compounds containing pyrimidinyl of this invention, the more preferred compounds include: the compounds represented by general formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F, I-3G, I-4C, I-4F or I-4G:

wherein:

$R_1$ is selected from H, F, Cl, Br, I, CN, $NO_2$, $NH_2$, carboxyl, CHO, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $CH_2OCH_3$, $CH_2OCH_2CH_3$ or $CH_2OCH_2CF_3$;

$R_2$ is selected from H, F, Cl, Br, I, CN, $NO_2$, $NH_2$, carboxyl, CHO, $CH_3$, $C_2H_5$, $OCH_3$, $OC_2H_5$ or $OCH_2CF_3$;

$R_3$ is selected from H, OH, CHO, $COCH_3$, $COC_2H_5$, $COC_3H_7$, $COCF_3$, COPh, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CH_2CF_3$, $OCH_3$, $OC_2H_5$, $OCH_2CF_3$,

$SCH_3$, $SC_2H_5$, $CH_2CH=CH_2$, $CH_2C\equiv CH$, $SO_2CH_3$, $SO_2CH_2CH_3$, $SO_2CH_2CF_3$, $SO_2NHCH_3$, $SO_2NHC_2H_5$, $SO_2N(CH_3)_2$, $SO_2N(C_2H_5)_2$, $CONHSO_2CH_3$, $COOCH_3$, $COOC_2H_5$, $COOC_3H_7$-n, $COOC_3H_7$-i, $CONHCH_3$, $CON(CH_3)_2$, $COOCH=CH_2$, $COOC\equiv CH$, $SNHCH_3$, $SNHC_2H_5$ or $SN(CH_3)_2$;

$R_4$, $R_5$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, n-$C_3H_7O$, i-$C_3H_7O$, n-$C_4H_9O$, s-$C_4H_9O$, i-$C_4H_9O$ or t-$C_4H_9O$;

$R_6$, $R_7$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, n-$C_3H_7O$, i-$C_3H_7O$, n-$C_4H_9O$, s-$C_4H_9O$, i-$C_4H_9O$ or t-$C_4H_9O$;

$R_8$ is selected from H, CN, F, Cl, Br, I, $CH_3$, $C_2H_5$ or $CF_3$;

$R_9$ is selected from H, CN, F, Cl, Br, I, $CH_3$, $C_2H_5$ or $CF_3$;

$R_{11}$ is selected from F, Cl, Br, I, CN, $NH_2$, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, $COOCH_3$, $COOC_2H_5$, $CONH_2$, $CONHCH_3$, $CONHC_2H_5$ or $CON(CH_3)_2$;

The integer n is selected from 0 to 5, when n is 0, the benzene ring is unsubstituted phenyl; when n is more than 1, $R_{11}$ may be the same or different;

$R_{14}$ is selected from $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$ or $CH_2CF_3$;

$R_{15}$, $R_{16}$ may be the same or different, selected respectively from H, F, Cl, Br, I, $NH_2$, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{17}$, $R_{18}$, $R_{19}$, $R_{20}$ may be the same or different, selected respectively from H, F, Cl, Br, I, CN, $NO_2$, $CH_3$, $CF_3$, $OCH_3$ or $OCF_3$;

$R_{21}$, $R_{22}$ may be the same or different, selected respectively from H, F, Cl, Br, I, OH, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{23}$, $R_{24}$, $R_{25}$, $R_{26}$ may be the same or different, selected respectively from H, F, Cl, Br, I, $NH_2$, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$ or $OCH_2CF_3$;

$R_{27}$, $R_{28}$ may be the same or different, selected respectively from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{29}$ is selected from $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $SO_2CH_3$, $SO_2CH_2CH_3$, $COCH_3$, $COC_2H_5$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{30}$ is selected from H, CN, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{31}$ is selected from $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $SO_2CH_3$, $SO_2CH_2CH_3$, $COCH_3$, $COC_2H_5$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{32}$ is selected from H, CN, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

$R_{33}$, $R_{34}$ may be selected respectively from $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $COCH_3$, $COC_2H_5$, $COOCH_3$, $COOC_2H_5$, $COOCH_2CF_3$, unsubstituted or further substituted (hetero)aryl, (hetero)arylmethyl, (hetero) arylcarbonyl, (hetero)arylmethylcarbonyl or (hetero) aryloxycarbonyl by 1 to 5 $R_{11}$;

$R_{35}$, $R_{36}$ may be selected respectively from H, CN, F, Cl, Br, I, $CH_3$, $C_2H_5$, n-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl or (hetero) aryloxycarbonyl by 1 to 5 $R_{11}$;

W is selected from H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $OCH_3$, $OC_2H_5$, $SCH_3$, $SC_2H_5$, $SO_2CH_3$ or $SO_2CH_2CH_3$;

Or the salts formed from the more preferred compounds represented by general formula above, with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid or citric acid.

In the substituted pyrazole compounds containing pyrimidinyl of this invention, the more preferred compounds include: the compounds represented by general formula I-1C, I-1F, I-1G, I-2C, I-2F, I-2G, I-4C, I-4F or I-4G:
wherein:
$R_1$ is selected from H, F, Cl, Br, I, $CH_3$, $C_2H_5$ or $CHF_2$;
$R_2$ is selected from H, F, Cl, Br, I, $NO_2$, $NH_2$, CHO, $CH_3$, $C_2H_5$, $OCH_3$ or $OC_2H_5$;
$R_3$ is selected from H, $CH_3$, $COCH_3$, $COCF_3$, $OCH_3$, $SCH_3$, $CH_2CH=CH_2$, $SO_2CH_3$, $SO_2NHCH_3$, $SO_2N(CH_3)_2$, $COOCH_3$, $CONHCH_3$, $CON(CH_3)_2$, $SNHCH_3$ or $SN(CH_3)_2$;
$R_4$, $R_5$ may be the same or different, selected respectively from H, F, Cl, Br or $CH_3$;

$R_6$, $R_7$ are H;
$R_8$ is H;
$R_9$ is H;
$R_{11}$ is selected from F, Cl, Br, I, CN, $NO_2$, $CH_3$, $CF_3$, $OCH_3$ or $OCF_3$;
The integer n is selected from 0 to 5, when n is 0, the benzene ring is unsubstituted phenyl; when n is more than 1, $R_{11}$ may be the same or different;
$R_{23}$, $R_{24}$, $R_{25}$, $R_{26}$ may be the same or different, selected respectively from H, F, Cl, Br, I or $CH_3$;
$R_{27}$, $R_{28}$ may be the same or different, selected respectively from H, F, Cl, Br or I;
W is selected from H, F, Cl, Br, I or $CH_3$;
Or the salts formed from the more preferred compounds represented by general formula above, with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid or citric acid.

In the substituted pyrazole compounds containing pyrimidinyl of this invention, the most preferred compounds include: the compounds represented by general formula I-1C, I-1F, I-1G, I-2C, I-2G, I-4C, I-4F or I-4G:
wherein
$R_1$ is selected from F, Cl, Br, I, $CH_3$, $C_2H_5$ or $CHF_2$;
$R_2$ is selected from F, Cl, Br, I, $NO_2$, $NH_2$, CHO, $CH_3$ or $OCH_3$;
$R_3$ is selected from H, $CH_3$, $COCH_3$, $OCH_3$, $CH_2CH=CH_2$, $SO_2CH_3$, $COOCH_3$, $CONHCH_3$, $CON(CH_3)_2$ or $SN(CH_3)_2$;
$R_4$, $R_5$ may be the same or different, selected respectively from H or $CH_3$;
$R_6$, $R_7$ are H;
$R_8$ is H;
$R_9$ is H;
$R_{11}$ is selected from F, Cl, Br, I, CN, $NO_2$, $CH_3$, $CF_3$, $OCH_3$ or $OCF_3$;
The integer n is selected from 1 to 5, when n is more than 1, $R_{11}$ may be the same or different;
$R_{23}$, $R_{24}$, $R_{25}$, $R_{26}$ are H;
$R_{27}$ is H;
$R_{28}$ is H;
W is selected from H, F, Cl, Br or I;
Or the salts formed from the most preferred compounds represented by general formula above, with hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid or citric acid.

The terms used above to definite the compounds of general formula I are as follows:

The "halogen" or "halo" is fluorine, chlorine, bromine or iodine. The "alkyl" stands for straight or branched chain alkyl, such as methyl, ethyl, propyl, isopropyl or tert-butyl. The "cycloalkyl" is substituted or unsubstituted cyclic alkyl, such as cyclopropyl, cyclopentyl or cyclohexyl. The substitute (s) is(are) methyl, halogen, etc. The "haloalkyl" stands for straight or branched chain alkyl, in which hydrogen atoms can be all or partly substituted with halogen, such as chloromethyl, dichloromethyl, trichloromethyl, fluoromethyl, difluoromethyl, trifluoromethyl, etc. The "alkylsulfinyl" means a straight-chain or branched alkyl is linked to the structure by (—SO—), such as methylsulfinyl. The "haloalkylsulfinyl" stands for a straight-chain or branched alkylsulfinyl, in which hydrogen atoms may be all or partly substituted with halogen. The "haloalkylsulfonyl" stands for a straight-chain or branched alkylsulfonyl, in which hydrogen atoms may be all or partly substituted with halogen. The "alkylaminothio" refers to —SNHCH₃, —SNHC₂H₅. The "dialkylaminothio" refers to —SN(CH₃)₂, —SN(C₂H₅)₂. The "alkylaminosulfonyl" refers to alkyl-NH—SO₂—. The "dialkylaminosulfonyl" refers to (alkyl)₂-N—SO₂—. The "alkylsulfonylaminocarbonyl" refers to alkyl-SO₂—NH—CO—. The "alkylcarbonylaminosulfonyl" refers to alkyl-CO—NH—SO₂—. The "alkylcarbonylalkyl" refers to alkyl-CO-alkyl-. The "alkylsulfonyloxy" such as alkyl-S(O)₂—O—. The "haloalkylsulfonyloxy" stands for in which hydrogen atoms may be all or partly substituted with halogen, such as CF₃—SO₂—O—. The "cycloalkyloxycarbonyl" means cyclopropyloxycarbonyl, cyclohexyloxycarbonyl, etc. The "alkoxy" refers to straight or branched chain alkyl, which is linked to the structure by oxygen atom. The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc. The "haloalkoxycarbonyl" refers to straight or branched chain alkoxycarbonyl, in which hydrogen atoms can be all or partly substituted with halogen, such as ClCH₂CH₂OCO—, CF₃CH₂OCO—, etc. The "alkoxyalkyl" means alkyl-O-alkyl-, such as —CH₂OCH₃. The "haloalkoxyalkyl" refers to alkoxyalkyl, in which hydrogen atom may be all or partial substituted with halogen, such as —CH₂OCH₂CH₂Cl, —CH₂OCH₂CF₃, etc. The "alkoxycarbonylalkyl" refers to alkoxycarbonyl-alkyl-, such as —CH₂COOCH₃. The "haloalkoxycarbonylalkyl" refers to alkoxycarbonylalkyl, in alkoxycarbonyl hydrogen atom may be all or partyl substituted with halogen, such as —CH₂COOCH₂CF₃. The "alkylcarbonyloxy": such as —OCOCH₃, etc. The "haloalkylcarbonyloxy" refers to alkylcarbonyloxy, in which hydrogen atom may be all or partyl substituted with halogen, such as —OCOCF₃, etc. The "alkoxycarbonyloxy" refers to alkoxycarbonyl-oxy, such as —OCOOCH₃. The "haloalkoxycarbonyloxy" refers to alkoxycarbonyloxy, in which hydrogen atom may be all or partyl substituted with halogen, such as —OCOOCF₃. The "alkylthiocarbonylalkyl" refers to alkylthiocarbonyl-alkyl-, such as —CH₂COSCH₃. The "haloalkylthiocarbonylalkyl" refers to alkylthiocarbonylalkyl, in which hydrogen atoms may be all or partly substituted with halogen, such as —CH₂COSCH₂CF₃. The "alkoxyalkoxy" stands for —OCH₂OCH₃, etc. The "haloalkoxyalkoxy" refers to alkoxyalkoxy, in which hydrogen atoms may be all or partly substituted with halogen, such as —OCH₂OCF₃. The "alkoxyalkoxycarbonyl": such as —COOCH₂CH₂OCH₃, etc. The "alkylthio" refers to straight or branched chain alkyl, which is linked to the structure by sulfur atom. The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc. The "alkylthioalkyl" means alkyl-S-alkyl-, such as —CH₂SCH₃. The "haloalkylthioalkyl" refers to alkylthioalkyl, in which hydrogen atoms may be all or partyl substituted with halogen, such as —CH₂SCH₂CH₂Cl, —CH₂SCH₂CF₃. The "alkylamino" refers to straight or branched chain alkyl, which is linked to the structure by nitrogen atom. The "haloalkylamino" refers to straight or branched chain alkylamino, in which hydrogen atoms may be all or partly substituted with halogen. The "dialkylamino": such as —N(CH₃)₂, —N(CH₃CH₂)₂. The "dihaloalkylamino" refers to dialkylamino, in which hydrogen atoms may be all or partyl substituted with halogen, such as —N(CF₃)₂, —N(CH₂CF₃)₂. The "alkenyl" refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The "haloalkenyl" stands for straight or branched chain alkenyl, in which hydrogen atoms can be all or partly substituted with halogen. The "alkenoxyl" refers to straight or branched chain alkenyl which is linked to the structure by oxygen. The "haloalkenoxyl" stands for a straight-chain or branched alkenoxyl, in which hydrogen atoms may be all or partly substituted with halogen. The "alkenylthio" refers to straight or branched chain alkenyl, which is linked to the structure by sulfur atom. Such as —SCH₂CH=CH₂. The "alkenoxylcarbonyl" means CH₂=CHCH₂OCO—, etc. The "alkynyl" refers to straight or branched chain alkynyl, such as ethynyl, 1-propynyl, 2-propynyl and different isomer of butynyl, pentynyl and hexynyl. Alkynyl also includes groups including more than one triple bonds, such as hexa-2,5-diynyl. The "haloalkynyl" stands for straight or branched chain alkynyl, in which hydrogen atoms can be all or partly substituted with halogen. The "alkynoxyl" refers to straight or branched chain alkynes which is linked to the structure by oxygen. The "haloalkynoxyl" stands for a straight-chain or branched alkynoxyl, in which hydrogen atoms may be all or partly substituted with halogen. The "alkynoxylcarbonyl" means —COOCH₂C≡CH, etc. The "alkylsulfonyl" means a straight-chain or branched alkyl which is linked to the structure by (—SO₂—), such as methylsulfonyl. The "haloalkylsulfonyl" stands for a straight-chain or branched alkylsulfonyl, in which hydrogen atoms may be all or partly substituted with halogen. The "alkylcarbonyl" means alkyl is linked to the structure by carbonyl, such as —COCH₃, —COCH₂CH₃. The "haloalkylcarbonyl" stands for a straight-chain or branched alkylcarbonyl, in which hydrogen atoms may be all or partly substituted with halogen, such as —COCF₃. The "alkoxycarbonyl" means alkoxy is linked to the structure by carbonyl. such as —COOCH₃, —COOCH₂CH₃. The "aminocarbonyl": such as NH₂CO—. The "alkylaminocarbonyl" means alkyl-NH—CO—, such as —CONHCH₃, —CONHCH₂CH₃. The "dialkylaminocarbonyl": such as —CON(CH₃)₂, —CON(CH₂CH₃)₂. The "aryl" in (hetero)aryl, (hetero)arylalkyl, (hetero)arylcarbonyl, (Hetero) arylmethylcarbonyl, (hetero)arylcarbonylalkyl, (hetero)aryloxycarbonyl, (Hetero)arylalkyloxycarbonyl includes phenyl or naphthyl etc. The "heteroaryl" stands for five member ring or six member ring containing one or more N, O, S hetero atoms, such as furyl, pyrazolyl, thiazolyl, pyridinyl, pyrimidinyl, pyrazinyl, pyridazinyl, triazinyl, quinolinyl, etc. "(Hetero)aryl" refers to phenyl, etc. "(Hetero)arylalkyl" means benzyl, phenylethyl, 4-chlorobenzyl, 2-chloro-pyridin-5-ylmethyl, 2-chloro-thiazol-5-ylmethyl, etc. "(Hetero)arylcarbonyl" refers to benzoyl, 4-Cl-benzoyl, etc. "(Hetero) arylmethylcarbonyl" refers to PhCH₂CO—. "(Hetero)arylcarbonylalkyl" refers to PhCOCH₂—. "(Hetero)aryloxycarbonyl": such as phenoxycarbonyl, p-chlorophenoxycarbonyl, p-nitrophenoxycarbonyl, naphthyloxycarbonyl, etc. Arylalkyloxycarbonyl means benzyloxycarbonyl, p-chlorobenzyloxycarbonyl, p-trifluoromethylbenzyloxycarbonyl, etc. "(Hetero)arylalkyloxycarbonyl" refers to —COOCH₂Ph, —COOCH₂-4-Cl-Ph, etc.

In the general formula I, some of preferred substituents of $R_1$, $R_2$, $R_3(X=NR_3)$, $R_4(R_5)$, $R_6(R_7)$, $R_8$, $R_9$, $R_{10}$ and w are separately listed in table1, table2, table3, table4, table5, table6, table7, table8 and table9, but without being restricted thereby.

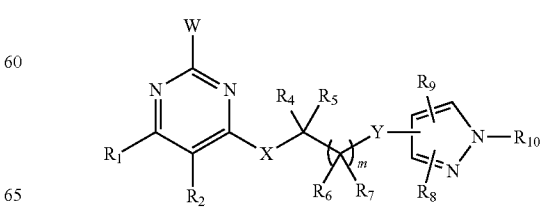

I

TABLE 1

R₁ substituents

| $R_1$ | $R_1$ | $R_1$ | $R_1$ |
|---|---|---|---|
| H | F | Cl | Br |
| I | $CH_3$ | $C_2H_5$ | n-$C_3H_7$ |
| i-$C_3H_7$ | n-$C_4H_9$ | s-$C_4H_9$ | i-$C_4H_9$ |
| t-$C_4H_9$ | $CF_3$ | $CCl_3$ | $CHF_2$ |
| $CH_2Cl$ | $CHBr_2$ | $CF_3CH_2$ | $CH(CH_3)F$ |
| $CH(CH_3)Cl$ | $CH(CH_3)Br$ | $C(CH_3)_2F$ | $CH=CH_2$ |
| $C\equiv CH$ | $SCH_3$ | $SOCH_3$ | $SO_2CH_3$ |
| CN | $NO_2$ | $NH_2$ | COOH |
| $COOCH_3$ | $COOC_2H_5$ | $CH_3NH$ | $C_2H_5NH$ |
| $OCH_3$ | $OC_2H_5$ | $OCF_3$ | $OCH_2CH=CH_2$ |
| $OCH_2CH=CHCl$ | $OCH_2C\equiv CH$ | $OCH_2C\equiv C-I$ | $OCH_2C\equiv CCH_3$ |
| $CONH_2$ | $CONHCH_3$ | $CON(CH_3)_2$ | $NHCH_3$ |
| $NHC_2H_5$ | $N(CH_3)_2$ | $N(C_2H_5)_2$ | $CH_2OCH_3$ |
| $CH_2OCH_2CH_3$ | $CH_2CH_2OCH_3$ | $CH_2CH_2OCH_2CH_3$ | $CH_2CH_2CH_2OCH_3$ |
| $CH_2CH_2CH_2OCH_2CH_3$ | | | |

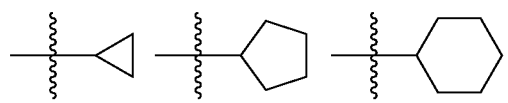

TABLE 2

R₂ substituents

| $R_2$ | $R_2$ | $R_2$ | $R_2$ |
|---|---|---|---|
| H | F | Cl | Br |
| I | CN | $NO_2$ | $NH_2$ |
| CHO | $CH_3$ | $C_2H_5$ | n-$C_3H_7$ |
| i-$C_3H_7$ | n-$C_4H_9$ | s-$C_4H_9$ | i-$C_4H_9$ |
| t-$C_4H_9$ | $OCH_3$ | $OC_2H_5$ | $OC_3H_7$-n |
| $OC_3H_7$-i | $OC_4H_9$-n | $OC_4H_9$-i | $OC_4H_9$-t |
| $OCH_2F$ | $OCHF_2$ | $OCF_3$ | $OCH_2CF_3$ |

TABLE 3

R₃ substituents

| $R_3$ | $R_3$ | $R_3$ | $R_3$ |
|---|---|---|---|
| H | OH | —C(=O)H | $CBr_3$ |
| $CH_3$ | $C_2H_5$ | n-$C_3H_7$ | i-$C_3H_7$ |
| n-$C_4H_9$ | i-$C_4H_9$ | t-$C_4H_9$ | $CCl_3$ |
| $CH_2Br$ | $CHF_2$ | $CHBr_2$ | $CF_3$ |
| $CH_2Cl$ | $CHCl_2$ | $CCl_3$ | $CH_2F$ |
| $OCH_3$ | $OC_2H_5$ | $OCH(CH_3)_2$ | $OC(CH_3)_3$ |
| $OCF_3$ | $OCH_2CF_3$ | $OCH_2F$ | $OCHF_2$ |
| $SCH_3$ | $SC_2H_5$ | $SCH_2CH=CH_2$ | $CH=CH_2$ |
| $CH_2CH=CH_2$ | $CH_2CH=CCl_2$ | $C\equiv CH$ | $CH_2C\equiv CH$ |
| $CH_2C\equiv C-I$ | $CH_2OCH_3$ | $CH_2OCH_2CH_3$ | $CH_2CH_2OCH_3$ |
| $CH_2CH_2OCH_2CH_3$ | $CH_2OCH_2Cl$ | $CH_2OCH_2CH_2Cl$ | $CH_2CH_2OCH_2Cl$ |
| $CH_2SCH_3$ | $CH_2SCH_2CH_3$ | $CH_2CH_2SCH_3$ | $CH_2CH_2SCH_2CH_3$ |
| $CH_2SCH_2Cl$ | $CH_2SCH_2CH_2Cl$ | $CH_2CH_2SCH_2Cl$ | $SOCH_3$ |
| $SOC_2H_5$ | $SOCF_3$ | $SOCH_2CF_3$ | $SO_2CH_3$ |
| $SO_2C_2H_5$ | $SO_2CF_3$ | $SO_2CH_2CF_3$ | $SO_2NHCOCH_3$ |
| $SO_2NHCH_3$ | $SO_2N(CH_3)_3$ | $CONHSO_2CH_3$ | $COCH_3$ |
| $COC_2H_5$ | CO-n-$C_3H_7$ | CO-i-$C_3H_7$ | CO-n-$C_4H_9$ |
| CO-i-$C_4H_9$ | CO-t-$C_4H_9$ | $COCF_3$ | $COCH_2Cl$ |
| $COOCH_3$ | $COOC_2H_5$ | COO-n-$C_3H_7$ | COO-t-$C_4H_9$ |
| $COOCF_3$ | $COOCH_2Cl$ | $COOCH_2CF_3$ | $CH_2COOCH_3$ |
| $CH_2COOC_2H_5$ | $CH_2COCH_3$ | $CH_2COOC_2H_5$ | $CONHCH_3$ |
| $CONHC_2H_5$ | $CONH$-t-$C_4H_9$ | $CON(CH_3)_2$ | $CON(C_2H_5)_2$ |
| $COOCH_2CH=CH_2$ | $COOCH_2C\equiv CH$ | $COOCH_2OCH_3$ | $COOCH_2CH_2OCH_3$ |
| $SNHCH_3$ | $SNHC_2H_5$ | $SN(CH_3)_2$ | $SN(C_2H_5)_2$ |

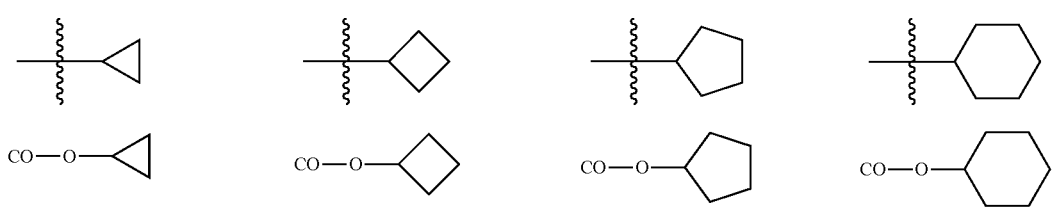

TABLE 3-continued
R₃ substituents
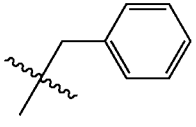 [SMILES: *Cc1ccccc1] 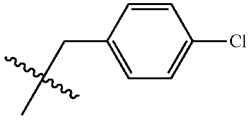 [SMILES: *Cc1ccc(Cl)cc1] 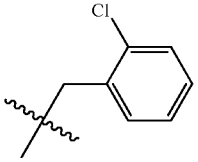 [SMILES: *Cc1ccccc1Cl] 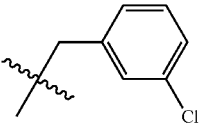
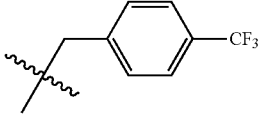 [SMILES: *Cc1ccc(C(F)(F)F)cc1] 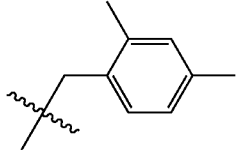 [SMILES: *Cc1ccc(C)cc1C] 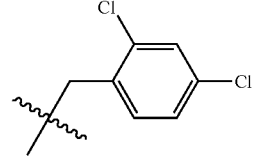 [SMILES: *Cc1ccc(Cl)cc1Cl] 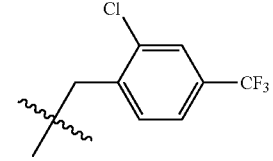 [SMILES: *Cc1ccc(C(F)(F)F)cc1Cl]
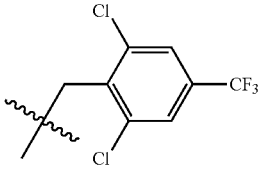 [SMILES: *Cc1c(Cl)cc(C(F)(F)F)cc1Cl] 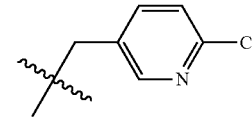 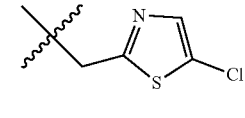 [SMILES: *Cc1ncc(Cl)s1] 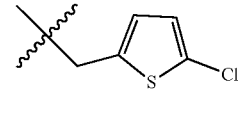 [SMILES: *Cc1ccc(Cl)s1]
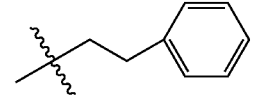 [SMILES: *CCc1ccccc1] 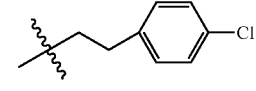 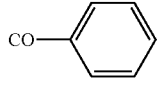 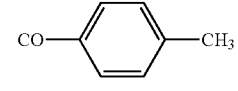
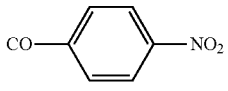 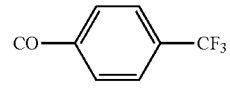 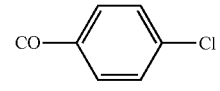 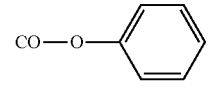
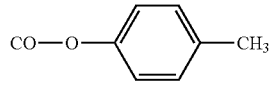 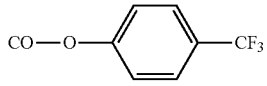 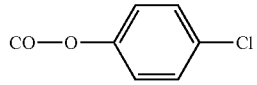 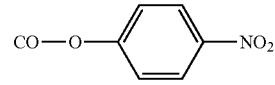
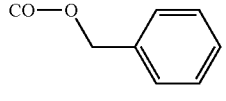 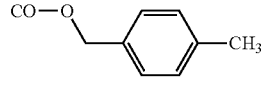 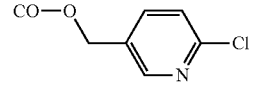 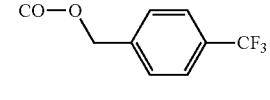
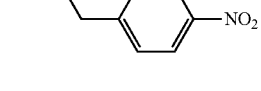 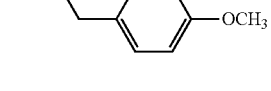 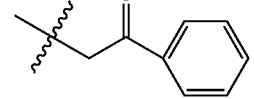 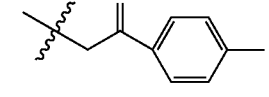
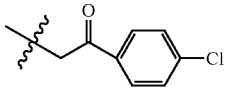 [SMILES: *CC(=O)c1ccc(Cl)cc1] 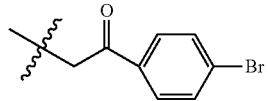 [SMILES: *CC(=O)c1ccc(Br)cc1] 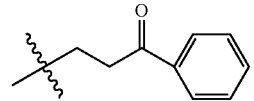 [SMILES: *CCC(=O)c1ccccc1] 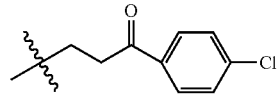 [SMILES: *CCC(=O)c1ccc(Cl)cc1]
TABLE 4
R₄(R₅) substituents
| $R_4(R_5)$ | $R_4(R_5)$ | $R_4(R_5)$ | $R_4(R_5)$ |
|---|---|---|---|
| H | F | Cl | Br |
| I | $CH_3$ | $C_2H_5$ | $n\text{-}C_3H_7$ |
| $i\text{-}C_3H_7$ | $n\text{-}C_4H_9$ | $s\text{-}C_4H_9$ | $i\text{-}C_4H_9$ |
| $t\text{-}C_4H_9$ | $CF_3$ | $CCl_3$ | $CHF_2$ |
| $CH_2Cl$ | $CHBr_2$ | $CF_3CH_2$ | $CH(CH_3)F$ |
| $CH(CH_3)Cl$ | $CH(CH_3)Br$ | $C(CH_3)_2F$ | $OCH_3$ |

TABLE 4-continued

| R4(R5) substituents | | | |
|---|---|---|---|
| R4(R5) | R4(R5) | R4(R5) | R4(R5) |
| OC2H5 | n-C3H7O | i-C3H7O | n-C4H9O |
| s-C4H9O | i-C4H9O | t-C4H9O | OCF3 |
| OCH2CF3 | cyclopropyl | cyclopentyl | cyclohexyl |

| CR4R5 | | |
|---|---|---|
| cyclopropyl | cyclopentyl | cyclohexyl |

TABLE 5

| R6(R7) substituents | | | |
|---|---|---|---|
| R6(R7) | R6(R7) | R6(R7) | R6(R7) |
| H | F | Cl | Br |
| I | CH3 | C2H5 | n-C3H7 |
| i-C3H7 | n-C4H9 | s-C4H9 | i-C4H9 |
| t-C4H9 | CF3 | CCl3 | CHF2 |
| CH2Cl | CHBr2 | CF3CH2 | CH(CH3)F |
| CH(CH3)Cl | CH(CH3)Br | C(CH3)2F | OCH3 |
| OC2H5 | n-C3H7O | i-C3H7O | n-C4H9O |
| s-C4H9O | i-C4H9O | t-C4H9O | OCF3 |
| OCH2CF3 | cyclopropyl | cyclopentyl | cyclohexyl |

| CR6R7 | | |
|---|---|---|
| cyclopropyl | cyclopentyl | cyclohexyl |

TABLE 6

| R8 substituents | | | |
|---|---|---|---|
| R8 | R8 | R8 | R8 |
| H | CN | CH3 | C2H5 |
| n-C3H7 | i-C3H7 | n-C4H9 | s-C4H9 |
| i-C4H9 | t-C4H9 | CF3 | CCl3 |
| CHF2 | CH2F | CH2Cl | CH2CF3 |
| CF2CF3 | COOCH3 | Ph | Ph-4-Cl |

TABLE 7

| R9 substituents | | | |
|---|---|---|---|
| R9 | R9 | R9 | R9 |
| H | CN | CH3 | C2H5 |
| n-C3H7 | i-C3H7 | n-C4H9 | s-C4H9 |
| i-C4H9 | t-C4H9 | CF3 | CCl3 |
| CHF2 | CH2F | CH2Cl | CH2CF3 |
| CF2CF3 | COOCH3 | Ph | Ph-4-Cl |

TABLE 8

| $R_{10}$ substituents | | | | |
|---|---|---|---|---|
| $R_{10}$ | $R_{10}$ | $R_{10}$ | $R_{10}$ | $R_{10}$ |
| $CH_3$ | Et | n-Pr | i-Pr | n-Bu |
| i-Bu | s-Bu | t-Bu | $CH_2F$ | $CHF_2$ |
| $CF_3$ | $CH_2CF_3$ | $COCH_3$ | COEt | CO-n-Pr |
| CO-n-Bu | CO-t-Bu | $COCF_3$ | $CO_2CH_3$ | $CO_2Et$ |
| $CO_2$-n-Pr | $CO_2$-i-Pr | $CO_2$-t-Bu | $CO_2CH_2CF_3$ | $CH_2OCH_3$ |

TABLE 8-continued

R₁₀ substituents (structures omitted)

TABLE 9

W substituents

| W | W | W | W | W |
|---|---|---|---|---|
| H | i-C₃H₇ | CHF₂ | OCH₃ | SCH₃ |
| F | n-C₄H₉ | CHBr₂ | OC₂H₅ | SC₂H₅ |
| Cl | i-C₄H₉ | CF₃ | OC₃H₇-n | SC₃H₇-n |
| Br | CH₃ | CH(CH₃)F | OC₃H₇-i | SC₃H₇-i |
| I | C₂H₅ | CH(CH₃)Cl | OC₄H₉-n | SC₄H₉-n |
| (cyclopropyl) | | CHCl₂ | OC₄H₉-i | SC₄H₉-i |
| | | CCl₃ | OC₄H₉-t | SC₄H₉-t |
| (cyclopentyl) | (cyclohexyl) | CH(n-C₄H₉)F | | |
| | | C(CH₃)₂F | OCF₃ | SO₂CH₃ |
| | | n-C₃H₇ | OCH₂CF₃ | t-C₄H₉ |

In the general formula I, some of the present invention compounds are also explained by the following compounds listed in Table10 to Table128, but without being restricted thereby. In the general formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F or I-3G, W═R₆═R₇═R₈═R₉═R₂₃═R₂₄═R₂₅═R₂₆═R₂₇═H.

In general formula I-1A,

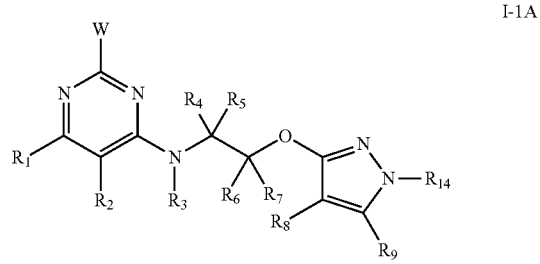

I-1A $R_1$=Cl, $R_2$=Cl, $R_3$=$R_4$=$R_5$=H, the substituents $R_{14}$ refer to Table 10, the representative compounds are coded as 10-1-10-15.

TABLE 10

| No. | $R_{14}$ |
|---|---|
| 10-1 | $CH_3$ |
| 10-2 | $C_2H_5$ |
| 10-3 | $n-C_3H_7$ |
| 10-4 | $i-C_3H_7$ |
| 10-5 | $n-C_4H_9$ |
| 10-6 | $s-C_4H_9$ |
| 10-7 | $i-C_4H_9$ |
| 10-8 | $t-C_4H_9$ |
| 10-9 | $CF_3$ |
| 10-10 | $CH_2CF_3$ |
| 10-11 | $CF_2CF_3$ |
| 10-12 | 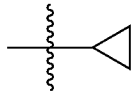 [SMILES: *C1CC1] |
| 10-13 | 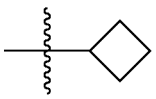 [SMILES: *C1CCC1] |
| 10-14 | 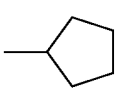 |
| 10-15 | 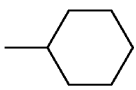 |

Table 11: in general formula I-IA, $R_1$=$CH_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 11-1-11-15.

Table 12: in general formula I-IA, $R_1$=$C_2H_5$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 12-1-12-15.

Table 13: in general formula I-IA, $R_1$=$CHF_2$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 13-1-13-15.

Table 14: in general formula I-IA, $R_1$=$CF_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 14-1-14-15.

Table 15: in general formula I-IA, $R_1$=Cl, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 15-1-15-15.

Table 16: in general formula I-IA, $R_1$=$CH_3$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 16-1-16-15.

Table 17: in general formula I-IA, $R_1$=$C_2H_5$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 17-1-17-15.

Table 18: in general formula I-IA, $R_1$=$CHF_2$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 18-1-18-15.

Table 19: in general formula I-IA, $R_1$=$CF_3$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 19-1-19-15.

In general formula I-IB,

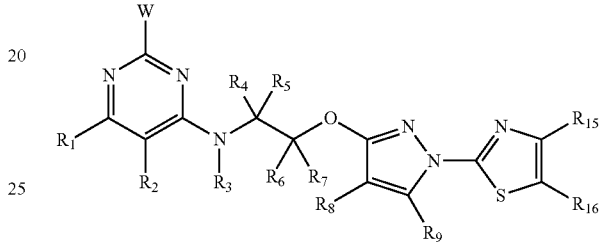

I-1B $R_1$=Cl, $R_2$=Cl, $R_3$=$R_4$=$R_5$=H, the substituents $R_{15}$ and $R_{16}$ refer to Table 20, the representative compounds are coded as 20-1-20-10.

TABLE 20

| No. | $R_{15}$ | $R_{16}$ |
|---|---|---|
| 20-1 | H | H |
| 20-2 | H | Br |
| 20-3 | H | $CH_3$ |
| 20-4 | H | $NO_2$ |
| 20-5 | H | CN |
| 20-6 | H | $CF_3$ |
| 20-7 | Cl | H |
| 20-8 | $CH_3$ | H |
| 20-9 | $CF_3$ | H |
| 20-10 | $CF_3$ | $CO_2CH_3$ |

Table 21: in general formula I-IB, $R_1$=$CH_3$, $R_2$=Cl, $R_3$=$R_4$=$R_5$=H, the substituents $R_{15}$ and $R_{16}$ are consistent with those in Table 20 and corresponding to 20-1-20-10 in table 20 in turn, the representative compounds are coded as 21-1-21-10.

Table 22: in general formula I-IB, $R_1$=$C_2H_5$, $R_2$=Cl, $R_3$=$R_4$=$R_5$=H, the substituents $R_{15}$ and $R_{16}$ are consistent with those in Table 20 and corresponding to 20-1-20-10 in table 20 in turn, the representative compounds are coded as 22-1-22-10.

Table 23: in general formula I-IB, $R_1$=$CHF_2$, $R_2$=Cl, $R_3$=$R_4$=$R_5$=H, the substituents $R_{15}$ and $R_{16}$ are consistent with those in Table 20 and corresponding to 20-1-20-10 in table 20 in turn, the representative compounds are coded as 23-1-23-10.

Table 24: in general formula I-IB, $R_1$=$CF_3$, $R_2$=Cl, $R_3$=$R_4$=$R_5$=H, the substituents $R_{15}$ and $R_{16}$ are consistent with those in Table 20 and corresponding to 20-1-20-10 in table 20 in turn, the representative compounds are coded as 24-1-24-10.

Table 25: in general formula I-IB, $R_1$=Cl, $R_2$=Cl, $R_3$=$R_4$=H, $R_5$=$CH_3$, the substituents $R_{15}$ and $R_{16}$ are consistent with those in Table 20 and corresponding to 20-1-20-10 in table 20 in turn, the representative compounds are coded as 25-1-25-10.

Table 26: in general formula I-IB, $R_1$=$CH_3$, $R_2$=Cl, $R_3$=$R_4$=H, $R_5$=$CH_3$, the substituents $R_{15}$ and $R_{16}$ are consistent with those in Table 20 and corresponding to 20-1-20-10 in table 20 in turn, the representative compounds are coded as 26-1-26-10.

Table 27: in general formula I-IB, $R_1$=$C_2H_5$, $R_2$=Cl, $R_3$=$R_4$=H, $R_5$=$CH_3$, the substituents $R_{15}$ and $R_{16}$ are consistent with those in Table 20 and corresponding to 20-1-20-10 in table 20 in turn, the representative compounds are coded as 27-1-27-10.

Table 28: in general formula I-IB, $R_1$=$CHF_2$, $R_2$=Cl, $R_3$=$R_4$=H, $R_5$=$CH_3$, the substituents $R_{15}$ and $R_{16}$ are consistent with those in Table 20 and corresponding to 20-1-20-10 in table 20 in turn, the representative compounds are coded as 28-1-28-10.

Table 29: in general formula I-IB, $R_1$=$CF_3$, $R_2$=Cl, $R_3$=$R_4$=H, $R_5$=$CH_3$, the substituents $R_{15}$ and $R_{16}$ are consistent with those in Table 20 and corresponding to 20-1-20-10 in table 20 in turn, the representative compounds are coded as 29-1-29-10.

In general formula I-IC,

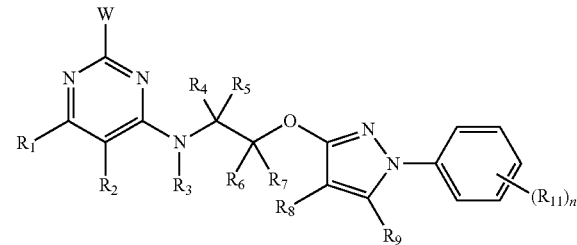

I-1C $R_1$=Cl, $R_2$=Cl, $R_3$=$R_4$=$R_5$=H, the substituents $(R_{11})n$ refer to Table 30, the representative compounds are coded as 30-1-30-279.

TABLE 30

| No. | $(R_{11})n$ | No. | $(R_{11})n$ | No. | $(R_{11})n$ |
|---|---|---|---|---|---|
| 30-1 | H | 30-2 | 2-F | 30-3 | 3-F |
| 30-4 | 4-F | 30-5 | 2,3-2F | 30-6 | 2,4-2F |
| 30-7 | 2,5-2F | 30-8 | 2,6-2F | 30-9 | 3,4-2F |
| 30-10 | 3,5-2F | 30-11 | 2,3,4-3F | 30-12 | 2,3,5-3F |
| 30-13 | 2,4,5-3F | 30-14 | 2,3,6-3F | 30-15 | 2,4,6-3F |
| 30-16 | 3,4,5-3F | 30-17 | 2-Cl | 30-18 | 3-Cl |
| 30-19 | 4-Cl | 30-20 | 2,3-2Cl | 30-21 | 2,4-2Cl |
| 30-22 | 2,5-2Cl | 30-23 | 2,6-2Cl | 30-24 | 3,4-2Cl |
| 30-25 | 3,5-2Cl | 30-26 | 2,3,4-3Cl | 30-27 | 2,3,5-3Cl |
| 30-28 | 2,4,5-3Cl | 30-29 | 2,3,6-3Cl | 30-30 | 2,4,6-3Cl |
| 30-31 | 3,4,5-3Cl | 30-32 | 2-Br | 30-33 | 3-Br |
| 30-34 | 4-Br | 30-35 | 2,3-2Br | 30-36 | 2,4-2Br |
| 30-37 | 2,5-2Br | 30-38 | 2,6-2Br | 30-39 | 3,4-2Br |
| 30-40 | 3,5-2Br | 30-41 | 2,3,4-3Br | 30-42 | 2,3,5-3Br |
| 30-43 | 2,4,5-3Br | 30-44 | 2,3,6-3Br | 30-45 | 2,4,6-3Br |
| 30-46 | 3,4,5-3Br | 30-47 | 2-CN | 30-48 | 3-CN |
| 30-49 | 4-CN | 30-50 | 2-$NO_2$ | 30-51 | 3-$NO_2$ |
| 30-52 | 4-$NO_2$ | 30-53 | 2,4-2$NO_2$ | 30-54 | 2,4,6-3$NO_2$ |
| 30-55 | 2-$CH_3$ | 30-56 | 3-$CH_3$ | 30-57 | 4-$CH_3$ |
| 30-58 | 2,3-2$CH_3$ | 30-59 | 2,4-2$CH_3$ | 30-60 | 2,5-2$CH_3$ |
| 30-61 | 2,6-2$CH_3$ | 30-62 | 3,4-2$CH_3$ | 30-63 | 3,5-2$CH_3$ |
| 30-64 | 2-$C_2H_5$ | 30-65 | 3-$C_2H_5$ | 30-66 | 4-$C_2H_5$ |
| 30-67 | 2-$CF_3$ | 30-68 | 3-$CF_3$ | 30-69 | 4-$CF_3$ |
| 30-70 | 2-$OCH_3$ | 30-71 | 3-$OCH_3$ | 30-72 | 4-$OCH_3$ |
| 30-73 | 2-$SCH_3$ | 30-74 | 3-$SCH_3$ | 30-75 | 4-$SCH_3$ |
| 30-76 | 2-$OCF_3$ | 30-77 | 3-$OCF_3$ | 30-78 | 4-$OCF_3$ |
| 30-79 | 2-$SCF_3$ | 30-80 | 3-$SCF_3$ | 30-81 | 4-$SCF_3$ |
| 30-82 | 2-$OC_2H_5$ | 30-83 | 3-$OC_2H_5$ | 30-84 | 4-$OC_2H_5$ |
| 30-85 | 2-$NHCH_3$ | 30-86 | 3-$NHCH_3$ | 30-87 | 4-$NHCH_3$ |
| 30-88 | 2-$N(CH_3)_2$ | 30-89 | 3-$N(CH_3)_2$ | 30-90 | 4-$N(CH_3)_2$ |
| 30-91 | 2-$COCH_3$ | 30-92 | 3-$COCH_3$ | 30-93 | 4-$COCH_3$ |
| 30-94 | 2-$COC_2H_5$ | 30-95 | 3-$COC_2H_5$ | 30-96 | 4-$COC_2H_5$ |
| 30-97 | 2-$SO_2CH_3$ | 30-98 | 3-$SO_2CH_3$ | 30-99 | 4-$SO_2CH_3$ |
| 30-100 | 2-$OCHF_2$ | 30-101 | 3-$OCHF_2$ | 30-102 | 4-$OCHF_2$ |
| 30-103 | 2-$SO_2C_2H_5$ | 30-104 | 3-$SO_2C_2H_5$ | 30-105 | 4-$SO_2C_2H_5$ |
| 30-106 | 2-$CO_2CH_3$ | 30-107 | 3-$CO_2CH_3$ | 30-108 | 4-$CO_2CH_3$ |
| 30-109 | 2-$CO_2C_2H_5$ | 30-110 | 3-$CO_2C_2H_5$ | 30-111 | 4-$CO_2C_2H_5$ |
| 30-112 | 2-$CH_2OCH_3$ | 30-113 | 3-$CH_2OCH_3$ | 30-114 | 4-$CH_2OCH_3$ |
| 30-115 | 2-$OCOCH_3$ | 30-116 | 3-$OCOCH_3$ | 30-117 | 4-$OCOCH_3$ |
| 30-118 | 2-$OCOCH_2CH_3$ | 30-119 | 3-$OCOCH_2CH_3$ | 30-120 | 4-$OCOCH_2CH_3$ |
| 30-121 | 2-$OCO_2CH_3$ | 30-122 | 3-$OCO_2CH_3$ | 30-123 | 4-$OCO_2CH_3$ |
| 30-124 | 2-$OCH_2OCH_3$ | 30-125 | 3-$OCH_2OCH_3$ | 30-126 | 4-$OCH_2OCH_3$ |
| 30-127 | 2-$OCF_2OCF_3$ | 30-128 | 3-$OCF_2OCF_3$ | 30-129 | 4-$OCF_2OCF_3$ |
| 30-130 | 2-COPh | 30-131 | 3-COPh | 30-132 | 4-COPh |
| 30-133 | 2-$COCH_2$Ph | 30-134 | 3-$COCH_2$Ph | 30-135 | 4-$COCH_2$Ph |
| 30-136 | 2-NHPh | 30-137 | 3-NHPh | 30-138 | 4-NHPh |
| 30-139 | 2-OPh | 30-140 | 3-OPh | 30-141 | 4-OPh |
| 30-142 | 2-CONHPh | 30-143 | 3-CONHPh | 30-144 | 4-CONHPh |
| 30-145 | 2-$CO_2$Ph | 30-146 | 3-$CO_2$Ph | 30-147 | 4-$CO_2$Ph |
| 30-148 | 2-$CONH_2$ | 30-149 | 3-$CONH_2$ | 30-150 | 4-$CONH_2$ |
| 30-151 | 2-Cl-4-F | 30-152 | 2-Cl-4-Br | 30-153 | 2-Cl-4-$CH_3$ |

TABLE 30-continued

| No. | (R$_{11}$)n | No. | (R$_{11}$)n | No. | (R$_{11}$)n |
|---|---|---|---|---|---|
| 30-154 | 2-Cl-4-CF$_3$ | 30-155 | 2-Cl-4-NO$_2$ | 30-156 | 2-Cl-4-CN |
| 30-157 | 2-Cl-4-OCF$_3$ | 30-158 | 2-F-4-Cl | 30-159 | 2-Br-4-Cl |
| 30-160 | 2-CH$_3$-4-Cl | 30-161 | 2-CF$_3$-4-Cl | 30-162 | 2-NO$_2$-4-Cl |
| 30-163 | 2-CN-4-Cl | 30-164 | 2-OCF$_3$-4-Cl | 30-165 | 2,6-2Cl-4-NO$_2$ |
| 30-166 | 2,6-2Cl-4-CF$_3$ | 30-167 | 2,6-2Cl-4-CN | 30-168 | 2,6-2Cl-4-COCH$_3$ |
| 30-169 | 2,6-2Cl-4-CONH$_2$ | 30-170 | 2,4-2Cl-6-NO$_2$ | 30-171 | 2,4-2Cl-6-CN |
| 30-172 | 2,4-2Cl-6-CF$_3$ | 30-173 | 2,4-2F-6-NO$_2$ | 30-174 | 2,6-2F-4-NO$_2$ |
| 30-175 | 2-NO$_2$-4-F | 30-176 | 2-NO$_2$-4-Br | 30-177 | 2-NO$_2$-4-CF$_3$ |
| 30-178 | 2-NO$_2$-4-CN | 30-179 | 2-NO$_2$-4-COCH$_3$ | 30-180 | 2-NO$_2$-4-CONH$_2$ |
| 30-181 | 2-NO$_2$-4-CH$_3$ | 30-182 | 2-NO$_2$-4-OCH$_3$ | 30-183 | 2-NO$_2$-4-SCH$_3$ |
| 30-184 | 2-NO$_2$-4-NCH$_3$ | 30-185 | 2-F-4-NO$_2$ | 30-186 | 2-Br-4-NO$_2$ |
| 30-187 | 2-CF$_3$-4-NO$_2$ | 30-188 | 2-CN-4-NO$_2$ | 30-189 | 2-COCH$_3$-4-NO$_2$ |
| 30-190 | 2-CONH$_2$-4-NO$_2$ | 30-191 | 2-CH$_3$-4-NO$_2$ | 30-192 | 2-Cl-4-F-6-NO$_2$ |
| 30-193 | 2-Cl-4-Br-6-NO$_2$ | 30-194 | 2-Cl-4-CH$_3$-6-NO$_2$ | 30-195 | 2-Cl-4-CF$_3$-6-NO$_2$ |
| 30-196 | 2-Cl-4,6-2NO$_2$ | 30-197 | 2-Cl-4-CN-6-NO$_2$ | 30-198 | 2-Cl-4-OCF$_3$-6-NO$_2$ |
| 30-199 | 2-F-4-Cl-6-NO$_2$ | 30-200 | 2-Br-4-Cl-6-NO$_2$ | 30-201 | 2-CH$_3$-4-Cl-6-NO$_2$ |
| 30-202 | 2-CF$_3$-4-Cl-6-NO$_2$ | 30-203 | 4-Cl-2,6-2NO$_2$ | 30-204 | 2-CF$_3$-4-CN |
| 30-205 | 2-CN-4-CF$_3$ | 30-206 | 4-CF$_3$-2,6-2NO$_2$ | 30-207 | 4-CN-2,6-2NO$_2$ |
| 30-208 | 4-CH$_3$-2,6-2NO$_2$ | 30-209 | 4-OCF$_3$-2,6-2NO$_2$ | 30-210 | 4-OCH$_3$-2,6-2NO$_2$ |
| 30-211 | 4-SCH$_3$-2,6-2NO$_2$ | 30-212 | 4-NHCH$_3$-2,6-2NO$_2$ | 30-213 | 4-F-2,6-2NO$_2$ |
| 30-214 | 2-CF$_3$-4,6-2NO$_2$ | 30-215 | 2-CN-4,6-2NO$_2$ | 30-216 | 2-CH$_3$-4,6-2NO$_2$ |
| 30-217 | 2-F-4,6-2NO$_2$ | 30-218 | 2-OCF$_3$-4,6-2NO$_2$ | 30-219 | 2-CF$_3$-4-Br |
| 30-220 | 3-CF$_3$-4-NO$_2$ | 30-221 | 2-CN-4-Cl-6-NO$_2$ | 30-222 | 2-OCF$_3$-4-Cl-6-NO$_2$ |
| 30-223 | 3-CF$_3$-4-CN | 30-224 | 3-CN-4-CF$_3$ | 30-225 | 2-CF$_3$-4-Br-6-NO$_2$ |
| 30-226 | 3-NO$_2$-4-CF$_3$ | 30-227 | 2-NO$_2$-4-CN-5-CF$_3$ | 30-228 | 2-NO$_2$-4-CF$_3$-5-CN |
| 30-229 | 4-OCF$_3$-2,6-2Br | 30-230 | 2-CH$_3$-4-Cl-5-CH$_2$CO$_2$C$_2$H$_5$ | 30-231 | 2,4-2Cl-3-CH$_3$ |
| 30-232 | 2,4-2Cl-3-CH$_3$-6-NO$_2$ | 30-233 | 2-Cl-3-CH$_3$ | 30-234 | 2-CH$_3$-3-Cl |
| 30-235 | 2-CH$_3$-3-Cl-4,6-2NO$_2$ | 30-236 | 2-CH$_3$-3-Cl-4-NO$_2$ | 30-237 | 2-CH$_3$-3-Cl-6-NO$_2$ |
| 30-238 | 2-Cl-3-CH$_3$-4,6-2NO$_2$ | 30-239 | 2-Cl-3-CH$_3$-4-NO$_2$ | 30-240 | 2-Cl-3-CH$_3$-6-NO$_2$ |
| 30-241 | 2-Br-4-NO$_2$-6-CN | 30-242 | 3-Cl-4-CF$_3$-2,6-2NO$_2$ | 30-243 | 2NO$_2$-4,5-2Cl |
| 30-244 | 2-NO$_2$-3,5-2Cl | 30-245 | 2,5-2Cl-4-NO$_2$ | 30-246 | 2,5-2Cl-6-NO$_2$ |
| 30-247 | 2,3-2Cl-4-NO$_2$ | 30-248 | 2,3-2Cl-6-NO$_2$ | 30-249 | 3,4-2Cl-2,6-2NO$_2$ |
| 30-250 | 2,5-2Cl-4,6-2NO$_2$ | 30-251 | 2,4,5-3Cl-6-NO$_2$ | 30-252 | 2,3,4-3Cl-5-NO$_2$ |
| 30-253 | 2,3,4-3Cl-6-NO$_2$ | 30-254 | 2,3,5-3Cl-4,6-2CN | 30-255 | 2,5-2Cl-4-OCF$_2$OCF$_3$ |
| 30-256 | 2,6-2Br-4-NO$_2$ | 30-257 | 2-F-4-NO$_2$-6-Cl | 30-258 | 2-Cl-4-NO$_2$-6-SCN |
| 30-259 | 2-Br-4-NO$_2$-6-Cl | 30-260 | 2-Cl-4-NO$_2$-6-OCH$_3$ | 30-261 | 2-Cl-4-NO$_2$-6-SCH$_3$ |
| 30-262 | 2-Cl-4-NO$_2$-6-NHCH$_3$ | 30-263 | 2-Cl-4-NO$_2$-6-SO$_2$CH$_3$ | 30-264 | 2-Cl-4-SO$_2$CH$_3$ |
| 30-265 | 2,6-2Cl-4-SO$_2$CH$_3$ | 30-266 | 2,6-2Cl-4-CH$_3$ | 30-267 | 2,6-2Cl-4-CO$_2$CH$_3$ |
| 30-268 | 2,6-2Cl-4-CONHCH$_3$ | 30-269 | 2,6-2Cl-4-CON(CH$_3$)$_2$ | 30-270 | 2,6-2Cl-4-CF(CF$_3$)$_2$ |
| 30-271 | 2-Cl-4-CF(CF$_3$)$_2$-6-Br | 30-272 | 2-F-4-CF(CF$_3$)$_2$-6-Br | 30-273 | 2-F-4-CF(CF$_3$)$_2$-6-Cl |
| 30-274 | 2,6-2F-4-CF(CF$_3$)$_2$-6-Cl | 30-275 | 2,4,5-3Cl-3,6-2CN | 30-276 | 2,3,5-3F-4,6-2CN |
| 30-277 | 2-SO$_2$NH$_2$ | 30-278 | 3-SO$_2$NH$_2$ | 30-279 | 4-SO$_2$NH$_2$ |

Table 30-1: in general formula I-IC, $R_1$=Cl, $R_2$=CH$_3$, $R_3$=$R_4$=$R_5$=H, the substituents (R$_{11}$)n are consistent with those in Table 30 and corresponding to 30-1-30-279 in table 30 in turn, the representative compounds are coded as 30-1-1-30-1-279.

Table 30-2: in general formula I-IC, $R_1$=Cl, $R_2$=OCH$_3$, $R_3$=$R_4$=$R_5$=H, the substituents (R$_{11}$)n are consistent with those in Table 30 and corresponding to 30-1-30-279 in table 30 in turn, the representative compounds are coded as 30-2-1-30-2-279.

Table 30-3: in general formula I-IC, $R_1$=Cl, $R_2$=CHO, $R_3$=$R_4$=$R_5$=H, the substituents (R$_{11}$)n are consistent with those in Table 30 and corresponding to 30-1-30-279 in table 30 in turn, the representative compounds are coded as 30-3-1-30-3-279.

Table 30-4: in general formula I-IC, $R_1$=Cl, $R_2$=Br, $R_3$=$R_4$=$R_5$=H, the substituents (R$_{11}$)n are consistent with those in Table 30 and corresponding to 30-1-30-279 in table 30 in turn, the representative compounds are coded as 30-4-1-30-4-279.

Table 31: in general formula I-IC, $R_1$=CH$_3$, $R_2$=Cl, $R_3$=$R_4$=$R_5$=H, the substituents (R$_{11}$)n are consistent with those in Table 30 and corresponding to 30-1-30-279 in table 30 in turn, the representative compounds are coded as 31-1-31-279.

Table 32: in general formula I-IC, $R_1$=C$_2$H$_5$, $R_2$=Cl, $R_3$=$R_4$=$R_5$=H, the substituents (R$_{11}$)n are consistent with those in Table 30 and corresponding to 30-1-30-279 in table 30 in turn, the representative compounds are coded as 32-1-32-279.

Table 33: in general formula I-IC, $R_1$=CHF$_2$, $R_2$=Cl, $R_3$=$R_4$=$R_5$=H, the substituents (R$_{11}$)n are consistent with those in Table 30 and corresponding to 30-1-30-279 in table 30 in turn, the representative compounds are coded as 33-1-33-279.

Table 34: in general formula I-IC, $R_1$=CF$_3$, $R_2$=Cl, $R_3$=$R_4$=$R_5$=H, the substituents (R$_{11}$)n are consistent with those in Table 30 and corresponding to 30-1-30-279 in table 30 in turn, the representative compounds are coded as 34-1-34-279.

Table 35: in general formula I-IC, $R_1$=Cl, $R_2$=Cl, $R_3$=$R_4$=H, $R_5$=CH$_3$, the substituents (R$_{11}$)n are consistent with those in Table 30 and corresponding to 30-1-30-279 in table 30 in turn, the representative compounds are coded as 35-1-35-279.

Table 36: in general formula I-IC, $R_1$=CH$_3$, $R_2$=Cl, $R_3$=$R_4$=H, $R_5$=CH$_3$, the substituents (R$_{11}$)n are consistent with those in Table 30 and corresponding to 30-1-30-279 in table 30 in turn, the representative compounds are coded as 36-1-36-279.

Table 37: in general formula I-IC, $R_1$=C$_2$H$_5$, $R_2$=Cl, $R_3$=$R_4$=H, $R_5$=CH$_3$, the substituents (R$_{11}$)n are consistent with those in Table 30 and corresponding to 30-1-30-279 in table 30 in turn, the representative compounds are coded as 37-1-37-279.

Table 38: in general formula I-IC, $R_1$=CHF$_2$, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 38-1-38-279.

Table 39: in general formula I-IC, $R_1$=CF$_3$, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 39-1-39-279.

Table 40: in general formula I-IF, $R_3$=$R_4$=$R_5$=H, the substituents $(R_{11})$n are consistent with those in Table 30 and corresponding to 30-1-30-279 in table 30 in turn, the representative compounds are coded as 40-1-40-279.

Table 41: in general formula I-IF, $R_3$=$R_4$=H, $R_5$=CH$_3$, the substituents $(R_{11})$n are consistent with those in Table 30 and corresponding to 30-1-30-279 in table 30 in turn, the representative compounds are coded as 41-1-41-279.

Table 42: in general formula I-IG, $R_3$=$R_4$=$R_5$=H, $R_{28}$=Cl, the substituents $(R_{11})$n are consistent with those in Table 30 and corresponding to 30-1-30-279 in table 30 in turn, the representative compounds are coded as 42-1-42-279.

Table 43: in general formula I-IG, $R_3$=$R_4$=$R_5$=H, $R_{28}$=CH$_3$, the substituents $(R_{11})$n are consistent with those in Table 30 and corresponding to 30-1-30-279 in table 30 in turn, the representative compounds are coded as 43-1-43-279.

Table 44: in general formula I-IG, $R_3$=$R_4$=H, $R_5$=CH$_3$, $R_{28}$=Cl, the substituents $(R_{11})$n are consistent with those in Table 30 and corresponding to 30-1-30-279 in table 30 in turn, the representative compounds are coded as 44-1-44-279.

Table 45: in general formula I-IG, $R_3$=$R_4$=H, $R_5$=CH$_3$, $R_{28}$=CH$_3$, the substituents $(R_{11})$n are consistent with those in Table 30 and corresponding to 30-1-30-279 in table 30 in turn, the representative compounds are coded as 45-1-45-279.

Table 46: in general formula I-2A, $R_1$=Cl, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 46-1-46-15.

Table 47: in general formula I-2A, $R_1$=CH$_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 47-1-47-15.

Table 48: in general formula I-2A, $R_1$=C$_2$H$_5$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 48-1-48-15.

Table 49: in general formula I-2A, $R_1$=CHF$_2$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 49-1-49-15.

Table 50: in general formula I-2A, $R_1$=CF$_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 50-1-50-15.

Table 51: in general formula I-2A, $R_1$=Cl, $R_2$=Cl, $R_3$=$R_4$=H, $R_5$=CH$_3$, the substituents $R_{14}$ are consistent with those in Table 10 and corresponding to 10-1-10-15 in table 10 in turn, the representative compounds are coded as 51-1-51-15.

Table 52: in general formula I-2A, $R_1$=CH$_3$, $R_2$=Cl, $R_3$=$R_4$=H, $R_5$=CH$_3$, the substituents $R_{14}$ are consistent with those in Table 10 and corresponding to 10-1-10-15 in table 10 in turn, the representative compounds are coded as 52-1-52-15.

Table 53: in general formula I-2A, $R_1$=C$_2$H$_5$, $R_2$=Cl, $R_3$=$R_4$=H, $R_5$=CH$_3$, the substituents $R_{14}$ are consistent with those in Table 10 and corresponding to 10-1-10-15 in table 10 in turn, the representative compounds are coded as 53-1-53-15.

Table 54: in general formula I-2A, $R_1$=CHF$_2$, $R_2$=Cl, $R_3$=$R_4$=H, $R_5$=CH$_3$, the substituents $R_{14}$ are consistent with those in Table 10 and corresponding to 10-1-10-15 in table 10 in turn, the representative compounds are coded as 54-1-54-15.

Table 55: in general formula I-2A, $R_1$=CF$_3$, $R_2$=Cl, $R_3$=$R_4$=H, $R_5$=CH$_3$, the substituents $R_{14}$ are consistent with those in Table 10 and corresponding to 10-1-10-15 in table 10 in turn, the representative compounds are coded as 55-1-55-15.

Table 56: in general formula I-2C, $R_1$=Cl, $R_2$=Cl, $R_3$=$R_4$=$R_5$=H, the substituents $(R_{11})$n are consistent with those in Table 30 and corresponding to 30-1-30-279 in table 30 in turn, the representative compounds are coded as 56-1-56-279.

Table 57: in general formula I-2C, $R_1$=CH$_3$, $R_2$=Cl, $R_3$=$R_4$=$R_5$=H, the substituents $(R_{11})$n are consistent with those in Table 30 and corresponding to 30-1-30-279 in table 30 in turn, the representative compounds are coded as 57-1-57-279.

Table 58: in general formula I-2C, $R_1$=C$_2$H$_5$, $R_2$=Cl, $R_3$=$R_4$=$R_5$=H, the substituents $(R_{11})$n are consistent with those in Table 30 and corresponding to 30-1-30-279 in table 30 in turn, the representative compounds are coded as 58-1-58-279.

Table 59: in general formula I-2C, $R_1$=CHF$_2$, $R_2$=Cl, $R_3$=$R_4$=$R_5$=H, the substituents $(R_{11})$n are consistent with those in Table 30 and corresponding to 30-1-30-279 in table 30 in turn, the representative compounds are coded as 59-1-59-279.

Table 60: in general formula I-2C, $R_1$=CF$_3$, $R_2$=Cl, $R_3$=$R_4$=$R_5$=H, the substituents $(R_{11})$n are consistent with those in Table 30 and corresponding to 30-1-30-279 in table 30 in turn, the representative compounds are coded as 60-1-60-279.

Table 61: in general formula I-2C, $R_1$=Cl, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 61-1-61-279.

Table 62: in general formula I-2C, $R_1$=CH$_3$, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 62-1-62-279.

Table 63: in general formula I-2C, $R_1$=C$_2$H$_5$, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 63-1-63-279.

Table 64: in general formula I-2C, $R_1$=CHF$_2$, $R_2$=Cl, $R_3$=$R_4$=H, $R_5$=CH$_3$, the substituents $(R_{11})$n are consistent with those in Table 30 and corresponding to 30-1-30-279 in table 30 in turn, the representative compounds are coded as 64-1-64-279.

Table 65: in general formula I-2C, $R_1$=$CF_3$, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 65-1-65-279.

Table 66: in general formula I-2F, $R_3$=$R_4$=$R_5$=H, the substituents $(R_{11})n$ are consistent with those in Table 30 and corresponding to 30-1-30-279 in table 30 in turn, the representative compounds are coded as 66-1-66-279.

Table 67: in general formula I-2F, $R_3$=$R_4$=H, $R_5$=$CH_3$, the substituents $(R_{11})n$ are consistent with those in Table 30 and corresponding to 30-1-30-279 in table 30 in turn, the representative compounds are coded as 67-1-67-279.

Table 68: in general formula I-2G, $R_3$=$R_4$=$R_5$=H, $R_{28}$=Cl, the substituents $(R_{11})n$ are consistent with those in Table 30 and corresponding to 30-1-30-279 in table 30 in turn, the representative compounds are coded as 68-1-68-279.

Table 69: in general formula I-2G, $R_3$=$R_4$=$R_5$=H, $R_{28}$=$CH_3$, the substituents $(R_{11})n$ are consistent with those in Table 30 and corresponding to 30-1-30-279 in table 30 in turn, the representative compounds are coded as 69-1-69-279.

Table 70: in general formula I-2G, $R_3$=$R_4$=H, $R_5$=$CH_3$, $R_{28}$=Cl, the substituents $(R_{11})n$ are consistent with those in Table 30 and corresponding to 30-1-30-279 in table 30 in turn, the representative compounds are coded as 70-1-70-279.

Table 71: in general formula I-2G, $R_3$=$R_4$=H, $R_5$=$CH_3$, $R_{28}$=$CH_3$, the substituents $(R_{11})n$ are consistent with those in Table 30 and corresponding to 30-1-30-279 in table 30 in turn, the representative compounds are coded as 71-1-71-279.

Table 72: in general formula I-3A, $R_1$=Cl, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 72-1-72-15.

Table 73: in general formula I-3A, $R_1$=$CH_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 73-1-73-15.

Table 74: in general formula I-3A, $R_1$=$C_2H_5$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 74-1-74-15.

Table 75: in general formula I-3A, $R_1$=$CHF_2$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 75-1-75-15.

Table 76: in general formula I-3A, $R_1$=$CF_3$, $R_2$=Cl, $R_3$=$R_4$=$R_5$=H, the substituents $R_{14}$ are consistent with those in Table 10 and corresponding to 10-1-10-15 in table 10 in turn, the representative compounds are coded as 76-1-76-15.

Table 77: in general formula I-3A, $R_1$=Cl, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 77-1-77-15.

Table 78: in general formula I-3A, $R_1$=$CH_3$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 78-1-78-15.

Table 79: in general formula I-3A, $R_1$=$C_2H_5$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 79-1-79-15.

Table 80: in general formula I-3A, $R_1$=$CHF_2$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 80-1-80-15.

Table 81: in general formula I-3A, $R_1$=$CF_3$, $R_2$=Cl, $R_3$=$R_4$=H, $R_5$=$CH_3$, the substituents $R_{14}$ are consistent with those in Table 10 and corresponding to 10-1-10-15 in table 10 in turn, the representative compounds are coded as 81-1-81-15.

Table 82: in general formula I-3C, $R_1$=Cl, $R_2$=Cl, $R_3$=$R_4$=$R_5$=H, the substituents $(R_{11})n$ are consistent with those in Table 30 and corresponding to 30-1-30-279 in table 30 in turn, the representative compounds are coded as 82-1-82-279.

Table 83: in general formula I-3C, $R_1$=$CH_3$, $R_2$=Cl, $R_3$=$R_4$=$R_5$=H, the substituents $(R_{11})n$ are consistent with those in Table 30 and corresponding to 30-1-30-279 in table 30 in turn, the representative compounds are coded as 83-1-83-279.

Table 84: in general formula I-3C, $R_1$=$C_2H_5$, $R_2$=Cl, $R_3$=$R_4$=$R_5$=H, the substituents $(R_{11})n$ are consistent with those in Table 30 and corresponding to 30-1-30-279 in table 30 in turn, the representative compounds are coded as 84-1-84-279.

Table 85: in general formula I-3C, $R_1$=$CHF_2$, $R_2$=Cl, $R_3$=$R_4$=$R_5$=H, the substituents $(R_{11})n$ are consistent with those in Table 30 and corresponding to 30-1-30-279 in table 30 in turn, the representative compounds are coded as 85-1-85-279.

Table 86: in general formula I-3C, $R_1$=$CF_3$, $R_2$=Cl, $R_3$=$R_4$=$R_5$=H, the substituents $(R_{11})n$ are consistent with those in Table 30 and corresponding to 30-1-30-279 in table 30 in turn, the representative compounds are coded as 86-1-86-279.

Table 87: in general formula I-3C, $R_1$=Cl, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 87-1-87-279.

Table 88: in general formula I-3C, $R_1$=$CH_3$, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 88-1-88-279.

Table 89: in general formula I-3C, $R_1$=$C_2H_5$, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 89-1-89-279.

Table 90: in general formula I-3C, $R_1$=$CHF_2$, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 90-1-90-279.

Table 91: in general formula I-3C, $R_1$=$CF_3$, $R_2$=Cl, $R_3$=$R_4$=H, $R_5$=$CH_3$, the substituents $(R_{11})n$ are consistent with those in Table 30 and corresponding to 30-1-30-279 in table 30 in turn, the representative compounds are coded as 91-1-91-279.

Table 92: in general formula I-3F, $R_3=R_4=R_5=H$, the substituents $(R_{11})n$ are consistent with those in Table 30 and corresponding to 30-1-30-279 in table 30 in turn, the representative compounds are coded as 92-1-92-279.

Table 93: in general formula I-3F, $R_3=R_4=H$, $R_5=CH_3$, the substituents $(R_{11})n$ are consistent with those in Table 30 and corresponding to 30-1-30-279 in table 30 in turn, the representative compounds are coded as 93-1-93-279.

Table 94: in general formula I-3G, $R_3=R_4=R_5=H$, $R_{28}=Cl$, the substituents $(R_{11})n$ are consistent with those in Table 30 and corresponding to 30-1-30-279 in table 30 in turn, the representative compounds are coded as 94-1-94-279.

Table 95: in general formula I-3G, $R_3=R_4=R_5=H$, $R_{28}=CH_3$, the substituents $(R_{11})n$ are consistent with those in Table 30 and corresponding to 30-1-30-279 in table 30 in turn, the representative compounds are coded as 95-1-95-279.

Table 96: in general formula I-3G, $R_3=R_4=H$, $R_5=CH_3$, $R_{28}=Cl$, the substituents $(R_{11})n$ are consistent with those in Table 30 and corresponding to 30-1-30-279 in table 30 in turn, the representative compounds are coded as 96-1-96-279.

Table 97: in general formula I-3G, $R_3=R_4=H$, $R_5=CH_3$, $R_{28}=CH_3$, the substituents $(R_{11})n$ are consistent with those in Table 30 and corresponding to 30-1-30-279 in table 30 in turn, the representative compounds are coded as 97-1-97-279.

Table 98: in general formula I-1C, $R_1=CH_3$, $R_2=Cl$, $R_3=R_4=H$, $R_5=F$, the substituents $(R_{11})n$ are consistent with those in Table 30 and corresponding to 30-1-30-279 in table 30 in turn, the representative compounds are coded as 98-1-98-279.

Table 99: in general formula I-1C, $R_1=C_2H_5$, $R_2=Cl$, $R_3=R_4=H$, $R_5=F$, the substituents $(R_{11})n$ are consistent with those in Table 30 and corresponding to 30-1-30-279 in table 30 in turn, the representative compounds are coded as 99-1-99-279.

Table 100: in general formula I-1C, $R_1=CHF_2$, $R_2=Cl$, $R_3=R_4=H$, $R_5=F$, the substituents $(R_{11})n$ are consistent with those in Table 30 and corresponding to 30-1-30-279 in table 30 in turn, the representative compounds are coded as 100-1-100-279.

Table 101: in general formula I-1C, $R_1=CH_3$, $R_2=Cl$, $R_3=R_4=R_5=F$, the substituents $(R_{11})n$ are consistent with those in Table 30 and corresponding to 30-1-30-279 in table 30 in turn, the representative compounds are coded as 101-1-101-279.

Table 102: in general formula I-1C, $R_1=C_2H_5$, $R_2=Cl$, $R_3=R_4=R_5=F$, the substituents $(R_{11})n$ are consistent with those in Table 30 and corresponding to 30-1-30-279 in table 30 in turn, the representative compounds are coded as 102-1-102-279.

Table 103: in general formula I-1C, $R_1=CHF_2$, $R_2=Cl$, $R_3=R_4=R_5=F$, the substituents $(R_{11})n$ are consistent with those in Table 30 and corresponding to 30-1-30-279 in table 30 in turn, the representative compounds are coded as 103-1-103-279.

Table 104: in general formula I-1H, $R_3=R_4=R_5=H$, $R_{29}=CH_3$, $R_{30}=H$, the substituents $(R_{11})n$ are consistent with those in Table 30 and corresponding to 30-1-30-279 in table 30 in turn, the representative compounds are coded as 104-1-104-279.

Table 105: in general formula I-1I, $R_3=R_4=R_5=H$, $R_{31}=CH_3$, $R_{32}=H$, the substituents $(R_{11})n$ are consistent with those in Table 30 and corresponding to 30-1-30-279 in table 30 in turn, the representative compounds are coded as 105-1-105-279.

Table 106: in general formula I-1J, $R_3=R_4=R_5=H$, $R_{33}=H$, the substituents $(R_{11})n$ are consistent with those in Table 30 and corresponding to 30-1-30-279 in table 30 in turn, the representative compounds are coded as 106-1-106-279.

Table 107: in general formula I-1K, $R_3=R_4=R_5=H$, $R_{34}=H$, the substituents $(R_{11})n$ are consistent with those in Table 30 and corresponding to 30-1-30-279 in table 30 in turn, the representative compounds are coded as 107-1-107-279.

Table 108: in general formula I-1L, $R_3=R_4=R_5=H$, $R_{35}=H$, the substituents $(R_{11})n$ are consistent with those in Table 30 and corresponding to 30-1-30-279 in table 30 in turn, the representative compounds are coded as 108-1-108-279.

Table 109: in general formula I-1M, $R_3=R_4=R_5=H$, $R_{36}=H$, the substituents $(R_{11})n$ are consistent with those in Table 30 and corresponding to 30-1-30-279 in table 30 in turn, the representative compounds are coded as 109-1-109-279.

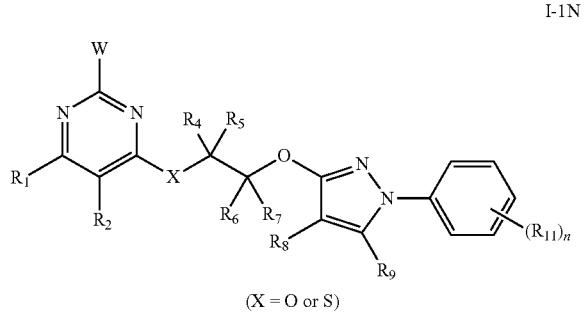

I-1N (X = O or S)

Table 110: in general formula I-1N, $R_1=CH_3$, $R_2=Cl$, $R_3=R_4=R_5=H$, X=O, the substituents $(R_{11})n$ are consistent with those in Table 30 and corresponding to 30-1-30-279 in table 30 in turn, the representative compounds are coded as 110-1-110-279.

Table 111: in general formula I-1N, $R_1=C_2H_5$, $R_2=Cl$, $R_3=R_4=R_5=H$, X=O, the substituents $(R_{11})n$ are consistent with those in Table 30 and corresponding to 30-1-30-279 in table 30 in turn, the representative compounds are coded as 111-1-111-279.

Table 112: in general formula I-1N, $R_1=CHF_2$, $R_2=Cl$, $R_3=R_4=R_5=H$, X=O, the substituents $(R_{11})n$ are consistent with those in Table 30 and corresponding to 30-1-30-279 in table 30 in turn, the representative compounds are coded as 112-1-112-279.

Table 113: in general formula I-1N, $R_1=CH_3$, $R_2=Cl$, $R_3=R_4=R_5=H$, X=S, the substituents $(R_{11})n$ are consistent with those in Table 30 and corresponding to 30-1-30-279 in table 30 in turn, the representative compounds are coded as 113-1-113-279.

Table 114: in general formula I-1N, $R_1=C_2H_5$, $R_2=Cl$, $R_3=R_4=R_5=H$, X=S, the substituents $(R_{11})n$ are consistent with those in Table 30 and corresponding to 30-1-30-279 in table 30 in turn, the representative compounds are coded as 114-1-114-279.

Table 115: in general formula I-1N, $R_1$=CHF$_2$, $R_2$=Cl, $R_3$=$R_4$=$R_5$=H, X=S, the substituents $(R_{11})n$ are consistent with those in Table 30 and corresponding to 30-1-30-279 in table 30 in turn, the representative compounds are coded as 115-1-115-279.

In general formula I-1C, $R_1$=CH$_3$, $R_2$=Cl, $R_4$=$R_5$=H, $(R_{11})n$=4-CH$_3$, the substituents $R_3$ (except H) refer to Table 116, the representative compounds are coded as 116-1-116-140.

TABLE 116

| No. | $R_3$ |
|---|---|
| 116-1 | S-i-C$_3$H$_7$ |
| 116-2 | OH |
| 116-3 | —C(=O)H |
| 116-4 | CBr$_3$ |
| 116-5 | CH$_3$ |
| 116-6 | C$_2$H$_5$ |
| 116-7 | n-C$_3$H$_7$ |
| 116-8 | i-C$_3$H$_7$ |
| 116-9 | n-C$_4$H$_9$ |
| 116-10 | i-C$_4$H$_9$ |
| 116-11 | t-C$_4$H$_9$ |
| 116-12 | CI$_3$ |
| 116-13 | CH$_2$Br |
| 116-14 | CHF$_2$ |
| 116-15 | CHBr$_2$ |
| 116-16 | CF$_3$ |
| 116-17 | CH$_2$Cl |
| 116-18 | CHCl$_2$ |
| 116-19 | CCl$_3$ |
| 116-20 | CH$_2$F |
| 116-21 | OCH$_3$ |
| 116-22 | OC$_2$H$_5$ |
| 116-23 | OCH(CH$_3$)$_2$ |
| 116-24 | OC(CH$_3$)$_3$ |
| 116-25 | OCF$_3$ |
| 116-26 | OCH$_2$CF$_3$ |
| 116-27 | OCH$_2$F |
| 116-28 | OCHF$_2$ |
| 116-29 | SCH$_3$ |
| 116-30 | SC$_2$H$_5$ |
| 116-31 | SCH$_2$CH=CH$_2$ |
| 116-32 | CH=CH$_2$ |
| 116-33 | CH$_2$CH=CH$_2$ |
| 116-34 | CH$_2$CH=CCl$_2$ |
| 116-35 | C≡CH |
| 116-36 | CH$_2$C≡CH |
| 116-37 | CH$_2$C≡C—I |
| 116-38 | CH$_2$OCH$_3$ |
| 116-39 | CH$_2$OCH$_2$CH$_3$ |
| 116-40 | CH$_2$CH$_2$OCH$_3$ |
| 116-41 | CH$_2$CH$_2$OCH$_2$CH$_3$ |
| 116-42 | CH$_2$OCH$_2$Cl |
| 116-43 | CH$_2$OCH$_2$CH$_2$Cl |
| 116-44 | CH$_2$CH$_2$OCH$_2$Cl |
| 116-45 | CH$_2$SCH$_3$ |
| 116-46 | CH$_2$SCH$_2$CH$_3$ |
| 116-47 | CH$_2$CH$_2$SCH$_3$ |
| 116-48 | CH$_2$CH$_2$SCH$_2$CH$_3$ |
| 116-49 | CH$_2$SCH$_2$Cl |
| 116-50 | CH$_2$SCH$_2$CH$_2$Cl |
| 116-51 | CH$_2$CH$_2$SCH$_2$Cl |
| 116-52 | SOCH$_3$ |
| 116-53 | SOC$_2$H$_5$ |
| 116-54 | SOCF$_3$ |
| 116-55 | SOCH$_2$CF$_3$ |
| 116-56 | SO$_2$CH$_3$ |
| 116-57 | SO$_2$C$_2$H$_5$ |
| 116-58 | SO$_2$CF$_3$ |
| 116-59 | SO$_2$CH$_2$CF$_3$ |
| 116-60 | SO$_2$NHCOCH$_3$ |
| 116-61 | SO$_2$NHCH$_3$ |
| 116-62 | SO$_2$N(CH$_3$)$_3$ |
| 116-63 | CONHSO$_2$CH$_3$ |
| 116-64 | COCH$_3$ |
| 116-65 | COC$_2$H$_5$ |
| 116-66 | CO-n-C$_3$H$_7$ |

TABLE 116-continued

| No. | $R_3$ |
|---|---|
| 116-67 | CO-i-C$_3$H$_7$ |
| 116-68 | CO-n-C$_4$H$_9$ |
| 116-69 | CO-i-C$_4$H$_9$ |
| 116-70 | CO-t-C$_4$H$_9$ |
| 116-71 | COCF$_3$ |
| 116-72 | COCH$_2$Cl |
| 116-73 | COOCH$_3$ |
| 116-74 | COOC$_2$H$_5$ |
| 116-75 | COO-n-C$_3$H$_7$ |
| 116-76 | COO-t-C$_4$H$_9$ |
| 116-77 | COOCF$_3$ |
| 116-78 | COOCH$_2$CH$_2$Cl |
| 116-79 | COOCH$_2$CF$_3$ |
| 116-80 | CH$_2$COOCH$_3$ |
| 116-81 | CH$_2$COOC$_2$H$_5$ |
| 116-82 | CH$_2$COCH$_3$ |
| 116-83 | CH$_2$COC$_2$H$_5$ |
| 116-84 | CONHCH$_3$ |
| 116-85 | CONHC$_2$H$_5$ |
| 116-86 | CONH-t-C$_4$H$_9$ |
| 116-87 | CON(CH$_3$)$_2$ |
| 116-88 | CON(C$_2$H$_5$)$_2$ |
| 116-89 | COOCH$_2$CH=CH$_2$ |
| 116-90 | COOCH$_2$C≡CH |
| 116-91 | COOCH$_2$OCH$_3$ |
| 116-92 | COOCH$_2$CH$_2$OCH$_3$ |
| 116-93 | SNHCH$_3$ |
| 116-94 | SNHC$_2$H$_5$ |
| 116-95 | SN(CH$_3$)$_2$ |
| 116-96 | SN(C$_2$H$_5$)$_2$ |
| 116-97 | 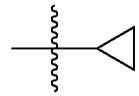 [SMILES: *C1CC1] |
| 116-98 | 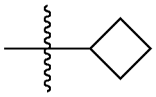 |
| 116-99 | 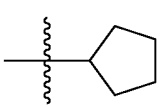 |
| 116-100 | 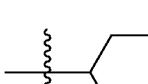 |
| 116-101 | 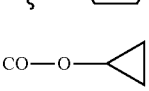 |
| 116-102 | 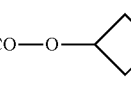 |
| 116-103 | 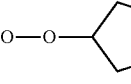 |
| 116-104 | 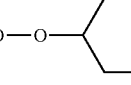 |
| 116-105 | 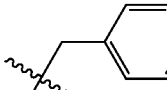 |

TABLE 116-continued

| No. | R₃ |
|---|---|
| 116-106 | 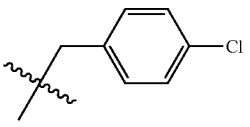 [SMILES: *Cc1ccc(Cl)cc1] 4-Cl-benzyl |
| 116-107 | 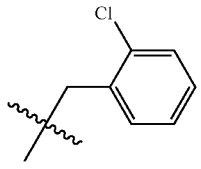 [SMILES: *Cc1ccccc1Cl] 2-Cl-benzyl |
| 116-108 | 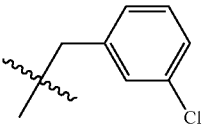 [SMILES: *Cc1cccc(Cl)c1] 3-Cl-benzyl |
| 116-109 | 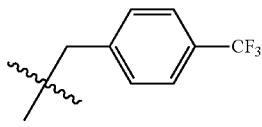 [SMILES: *Cc1ccc(C(F)(F)F)cc1] 4-CF₃-benzyl |
| 116-110 | 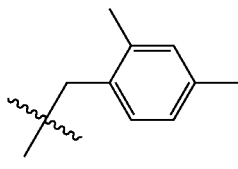 [SMILES: *Cc1ccc(C)cc1C] 2,4-dimethyl-benzyl |
| 116-111 | 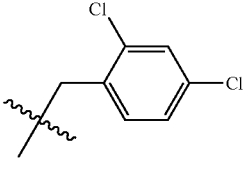 [SMILES: *Cc1ccc(Cl)cc1Cl] 2,4-diCl-benzyl |
| 116-112 | 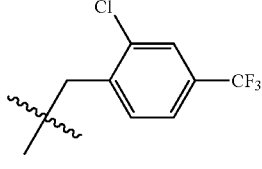 [SMILES: *Cc1ccc(C(F)(F)F)cc1Cl] 2-Cl-4-CF₃-benzyl |
| 116-113 | 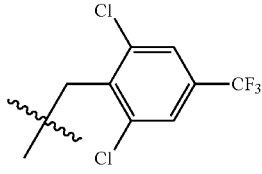 2,6-diCl-4-CF₃-benzyl |
| 116-114 | 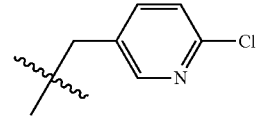 [SMILES: *Cc1ccc(Cl)nc1] (6-chloropyridin-3-yl)methyl |
| 116-115 | 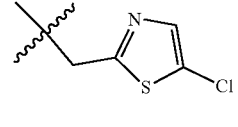 [SMILES: *Cc1ncc(Cl)s1] (5-chlorothiazol-2-yl)methyl |
| 116-116 | 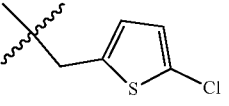 [SMILES: *Cc1ccc(Cl)s1] (5-chlorothiophen-2-yl)methyl |
| 116-117 | 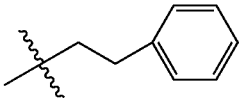 phenethyl |
| 116-118 | 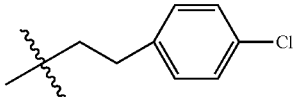 [SMILES: *CCc1ccc(Cl)cc1] 4-Cl-phenethyl |
| 116-119 | 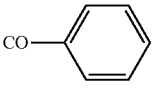 CO-phenyl |
| 116-120 |  CO-4-CH₃-phenyl |
| 116-121 |  CO-4-NO₂-phenyl |
| 116-122 | 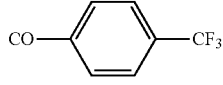 CO-4-CF₃-phenyl |
| 116-123 | 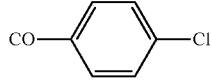 CO-4-Cl-phenyl |
| 116-124 | 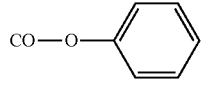 CO-O-phenyl |
| 116-125 | 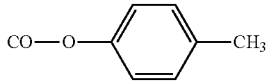 CO-O-4-CH₃-phenyl |
| 116-126 | 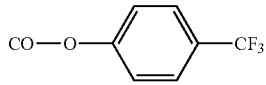 CO-O-4-CF₃-phenyl |
| 116-127 | 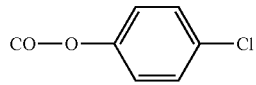 CO-O-4-Cl-phenyl |
| 116-128 | 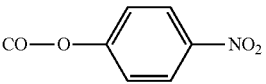 CO-O-4-NO₂-phenyl |
| 116-129 | 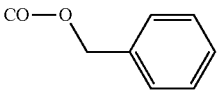 CO-O-benzyl |
| 116-130 | 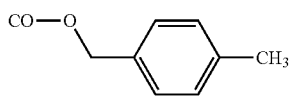 CO-O-4-CH₃-benzyl |

TABLE 116-continued
| No. | R₃ |
|---|---|
| 116-131 | 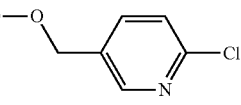 |
| 116-132 | 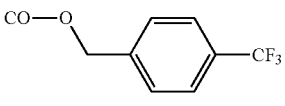 |
| 116-133 | 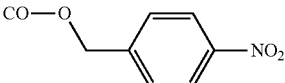 |
| 116-134 | 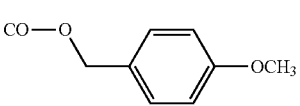 |
| 116-135 | 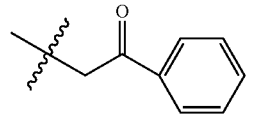 [SMILES: *CC(=O)c1ccccc1] |
| 116-136 | 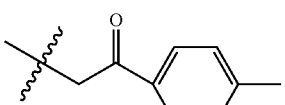 |
| 116-137 | 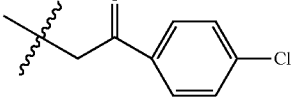 |
| 116-138 | 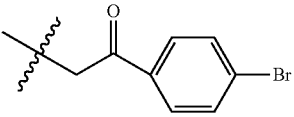 [SMILES: *CC(=O)c1ccc(Br)cc1] |
| 116-139 | 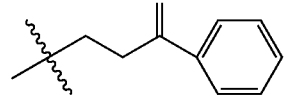 |
| 116-140 | 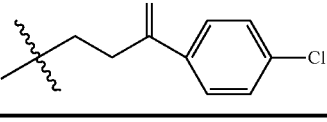 |
The salts of some compounds having a structure as represented by formula I of the present invention are listed in Table 117, but without being restricted thereby.
TABLE 117
the salts of some compounds
| No. | structure |
|---|---|
| 117-1 | 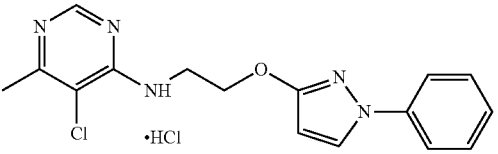 [SMILES: Cc1ncnc(NCCOc2ccn(-c3ccccc3)n2)c1Cl ; Cl] |
| 117-2 | 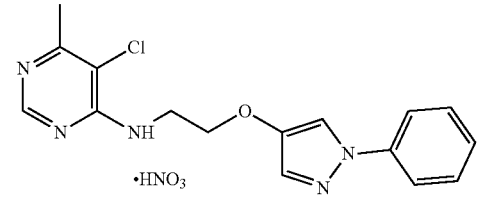 |
| 117-3 | 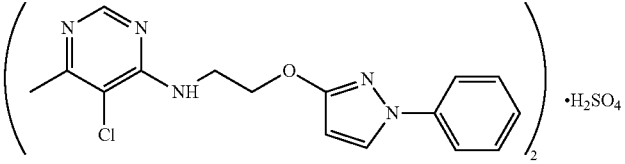 |
| 117-4 | 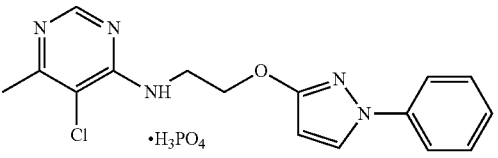 |

TABLE 117-continued
the salts of some compounds
| No. | structure |
|---|---|
| 117-5 | 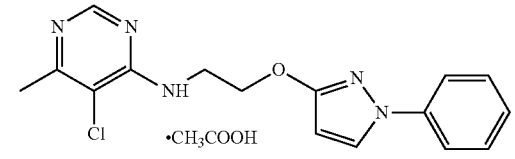 |
| 117-6 | 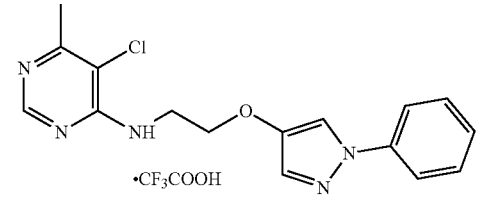 [SMILES: Cc1ncnc(NCCOc2cnn(-c3ccccc3)c2)c1Cl ; "·CF3COOH"] |
| 117-7 | 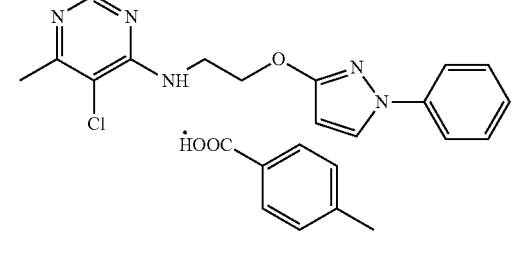 |
| 117-8 | 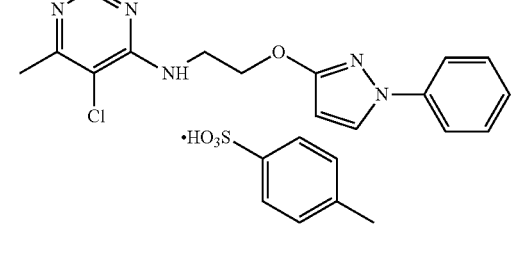 |
| 117-9 | 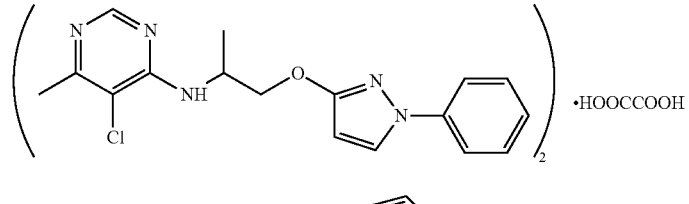 |
| 117-10 | 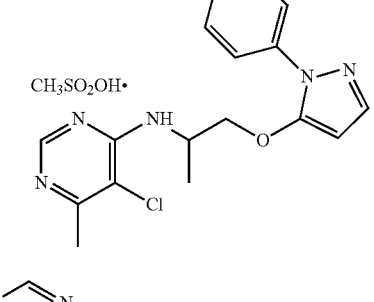 |
| 117-11 | 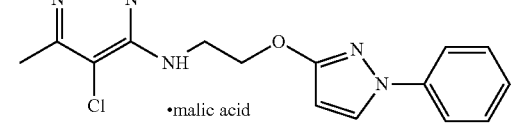 |

TABLE 117-continued
the salts of some compounds
| No. | structure |
|---|---|
| 117-12 | 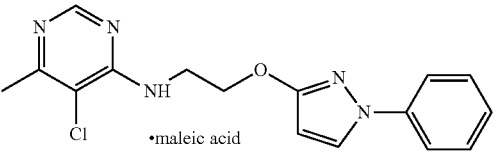 [SMILES: Cc1ncnc(NCCOc2ccn(-c3ccccc3)n2)c1Cl] •maleic acid |
| 117-13 | 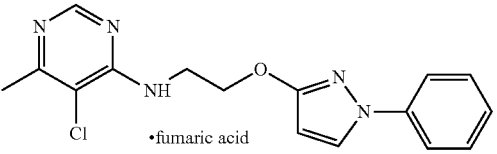 [SMILES: Cc1ncnc(NCCOc2ccn(-c3ccccc3)n2)c1Cl] •fumaric acid |
| 117-14 | 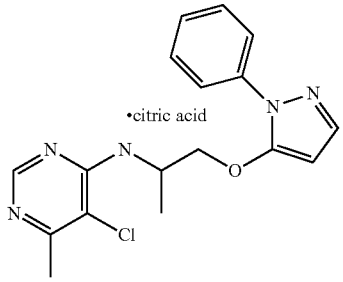 [SMILES: Cc1ncnc(NC(C)COc2ccnn2-c2ccccc2)c1Cl] •citric acid |
| 117-15 | 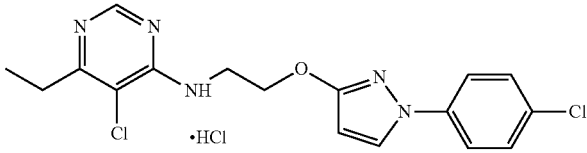 [SMILES: CCc1ncnc(NCCOc2ccn(-c3ccc(Cl)cc3)n2)c1Cl ; Cl] •HCl |
| 117-16 | 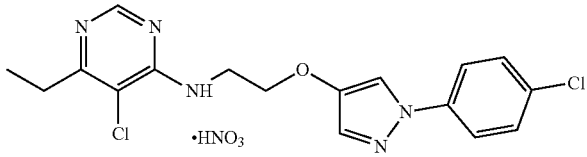 •HNO$_3$ |
| 117-17 | 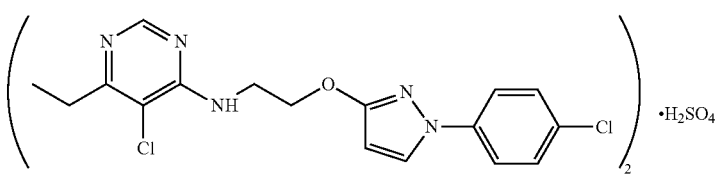 •H$_2$SO$_4$ |
| 117-18 | 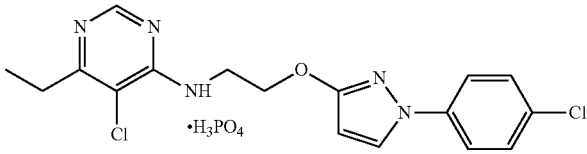 •H$_3$PO$_4$ |
| 117-19 | 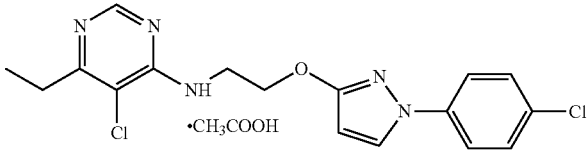 •CH$_3$COOH |

TABLE 117-continued the salts of some compounds

| No. | structure |
|---|---|
| 117-20 | Ethyl-chloro-pyrimidine-NH-CH₂CH₂-O-pyrazole(4-position)-N-(4-chlorophenyl) · CF₃COOH |
| 117-21 | Ethyl-chloro-pyrimidine-NH-CH₂CH₂-O-pyrazole(3-position)-N-(4-chlorophenyl) · HOOC-(4-methylphenyl) |
| 117-22 | Ethyl-chloro-pyrimidine-NH-CH₂CH₂-O-pyrazole(3-position)-N-(4-chlorophenyl) · HO₃S-(4-methylphenyl) |
| 117-23 | (Ethyl-chloro-pyrimidine-NH-CH₂CH₂-O-pyrazole(3-position)-N-(4-chlorophenyl))₂ · HOOCCOOH |
| 117-24 | Ethyl-chloro-pyrimidine-N-CH₂CH₂-O-pyrazole(5-position)-N-(4-chlorophenyl) · CH₃SO₂OH |
| 117-25 | Ethyl-chloro-pyrimidine-NH-CH₂CH₂-O-pyrazole(3-position)-N-(4-chlorophenyl) · malic acid |
| 117-26 | Ethyl-chloro-pyrimidine-NH-CH₂CH₂-O-pyrazole(3-position)-N-(4-chlorophenyl) · maleic acid |

TABLE 117-continued
the salts of some compounds
| No. | structure |
|---|---|
| 117-27 | 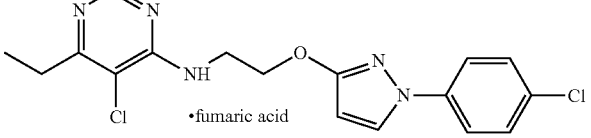 •fumaric acid |
| 117-28 | 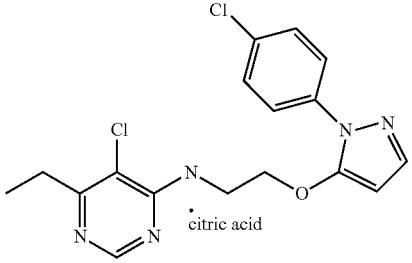 [SMILES: CCc1ncnc(NCCOc2ccnn2-c2ccc(Cl)cc2)c1Cl] •citric acid |
| 117-29 | 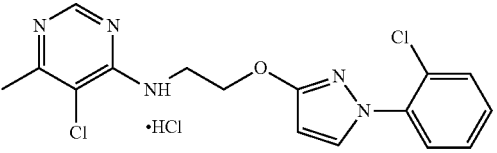 [SMILES: Cc1ncnc(NCCOc2ccn(-c3ccccc3Cl)n2)c1Cl ; Cl] •HCl |
| 117-30 | 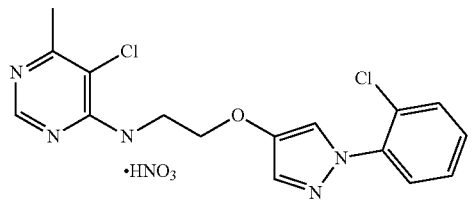 •HNO$_3$ |
| 117-31 | 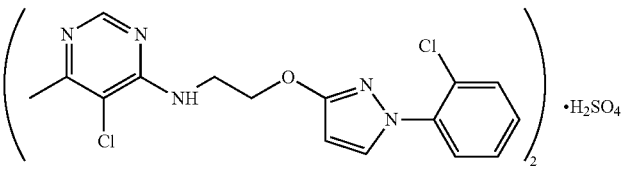 •H$_2$SO$_4$ |
| 117-32 | 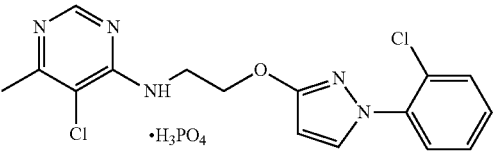 •H$_3$PO$_4$ |
| 117-33 | 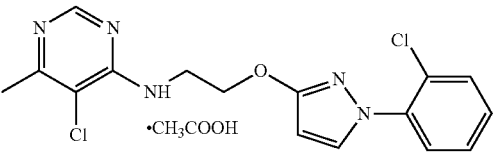 •CH$_3$COOH |
| 117-34 | 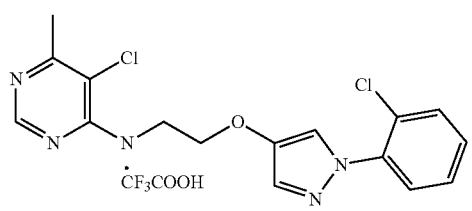 •CF$_3$COOH |

TABLE 117-continued the salts of some compounds

| No. | structure |
|---|---|
| 117-35 | Structure: 6-methyl-5-chloro-pyrimidin-4-yl–NH–CH₂CH₂–O–(3-pyrazolyl with N1-(2-chlorophenyl)) · HOOC-(4-methylphenyl) |
| 117-36 | Structure: 6-methyl-5-chloro-pyrimidin-4-yl–NH–CH₂CH₂–O–(3-pyrazolyl with N1-(2-chlorophenyl)) · HO₃S-(4-methylphenyl) |
| 117-37 | (6-methyl-5-chloro-pyrimidin-4-yl–NH–CH₂CH₂–O–(3-pyrazolyl with N1-(2-chlorophenyl)))₂ · HOOCCOOH |
| 117-38 | 6-methyl-5-chloro-pyrimidin-4-yl–N(CH₂CH₂–O–(5-pyrazolyl with N1-(2-chlorophenyl))) · CH₃SO₂OH |
| 117-39 | 6-methyl-5-chloro-pyrimidin-4-yl–NH–CH₂CH₂–O–(3-pyrazolyl with N1-(2-chlorophenyl)) · malic acid |
| 117-40 | 6-methyl-5-chloro-pyrimidin-4-yl–NH–CH₂CH₂–O–(3-pyrazolyl with N1-(2-chlorophenyl)) · maleic acid |
| 117-41 | 6-methyl-5-chloro-pyrimidin-4-yl–NH–CH₂CH₂–O–(3-pyrazolyl with N1-(2-chlorophenyl)) · fumaric acid |

TABLE 117-continued the salts of some compounds

| No. | structure |
|---|---|
| 117-42 | 5-chloro-6-methyl-N-(2-((1-(2-chlorophenyl)-1H-pyrazol-5-yl)oxy)ethyl)pyrimidin-4-amine · citric acid |
| 117-43 | 5-chloro-6-ethyl-N-(2-((1-(p-tolyl)-1H-pyrazol-3-yl)oxy)ethyl)pyrimidin-4-amine · HCl |
| 117-44 | 5-chloro-6-ethyl-N-(2-((1-(p-tolyl)-1H-pyrazol-3-yl)oxy)ethyl)pyrimidin-4-amine · HNO₃ |
| 117-45 | (5-chloro-6-ethyl-N-(2-((1-(p-tolyl)-1H-pyrazol-3-yl)oxy)ethyl)pyrimidin-4-amine)₂ · H₂SO₄ |
| 117-46 | 5-chloro-6-ethyl-N-(2-((1-(p-tolyl)-1H-pyrazol-4-yl)oxy)ethyl)pyrimidin-4-amine · H₃PO₄ |
| 117-47 | 5-chloro-6-ethyl-N-(2-((1-(p-tolyl)-1H-pyrazol-3-yl)oxy)ethyl)pyrimidin-4-amine · CH₃COOH |
| 117-48 | 5-chloro-6-ethyl-N-(2-((1-(p-tolyl)-1H-pyrazol-3-yl)oxy)ethyl)pyrimidin-4-amine · CF₃COOH |
| 117-49 | 5-chloro-6-ethyl-N-(2-((1-(p-tolyl)-1H-pyrazol-3-yl)oxy)ethyl)pyrimidin-4-amine · 4-methylbenzoic acid |

TABLE 117-continued the salts of some compounds

| No. | structure |
|---|---|
| 117-50 | [structure: 6-ethyl-5-chloro-pyrimidin-4-yl-N(ethyl)-2-ethoxy-4-(1-(p-tolyl)pyrazolyl), ·HO₃S-C₆H₄-CH₃ (p-toluenesulfonic acid)] |
| 117-51 | ([structure: 6-ethyl-5-chloro-pyrimidin-4-yl-NH-ethyl-O-3-(1-(p-tolyl)pyrazolyl)])₂ ·HOOCCOOH |
| 117-52 | [structure: 6-ethyl-5-chloro-pyrimidin-4-yl-N(ethyl)-2-ethoxy-3-(1-(p-tolyl)pyrazolyl), ·CH₃SO₂OH] |
| 117-53 | [structure: 6-ethyl-5-chloro-pyrimidin-4-yl-NH-ethyl-O-3-(1-(p-tolyl)pyrazolyl) ·malic acid] |
| 117-54 | [structure: 5-chloro-6-methyl-pyrimidin-4-yl-NH-ethyl-O-5-(1-(p-tolyl)pyrazolyl) ·maleic acid] |
| 117-55 | [structure: 5-chloro-6-methyl-pyrimidin-4-yl-NH-ethyl-O-5-(1-(p-tolyl)pyrazolyl) ·fumaric acid] |
| 117-56 | [structure: 6-ethyl-5-chloro-pyrimidin-4-yl-NH-ethyl-O-3-(1-(p-tolyl)pyrazolyl) ·citric acid] |

TABLE 117-continued
the salts of some compounds
| No. | structure |
|---|---|
| 117-57 | 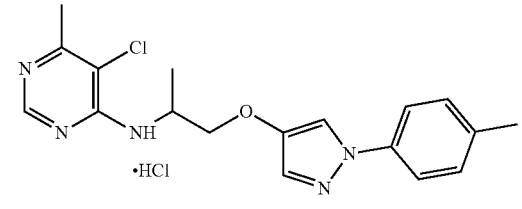 [SMILES: Cc1ccc(-n2cc(OCC(C)Nc3ncnc(C)c3Cl)cn2)cc1 ; Cl] |
| 117-58 | 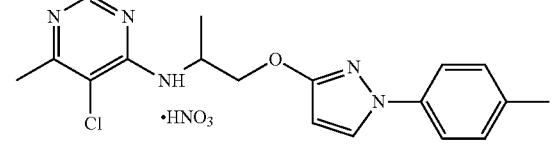 |
| 117-59 | 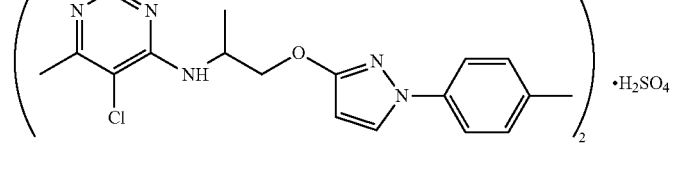 |
| 117-60 | 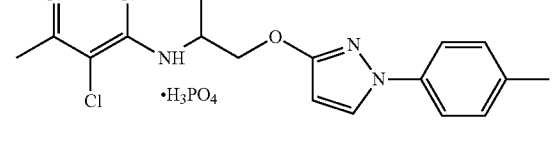 |
| 117-61 | 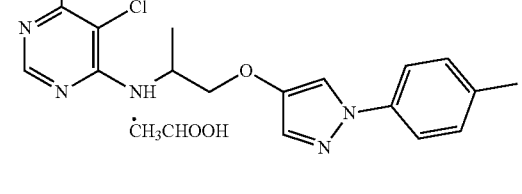 |
| 117-62 | 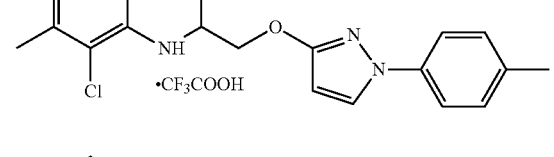 |
| 117-63 | 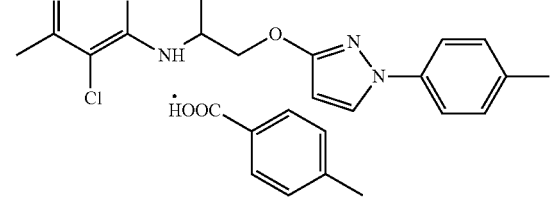 |

TABLE 117-continued the salts of some compounds

| No. | structure |
|---|---|
| 117-64 | (structure: 6-methyl-5-chloro-pyrimidin-4-yl-NH-CH(CH₃)-CH₂-O-pyrazole-N-(p-tolyl)) · HO₃S-C₆H₄-CH₃ |
| 117-65 | (6-methyl-5-chloro-pyrimidin-4-yl-NH-CH(CH₃)-CH₂-O-pyrazole-N-(p-tolyl))₂ · HOOCCOOH |
| 117-66 | (6-methyl-5-chloro-pyrimidin-4-yl-N-CH(CH₃)-CH₂-O-pyrazole-N-(p-tolyl)) · CH₃SO₂OH |
| 117-67 | (6-methyl-5-chloro-pyrimidin-4-yl-NH-CH(CH₃)-CH₂-O-pyrazole-N-(p-tolyl)) · malic acid |
| 117-68 | (6-methyl-5-chloro-pyrimidin-4-yl-NH-CH(CH₃)-CH₂-O-pyrazole-N-(p-tolyl)) · maleic acid |
| 117-69 | fumaric acid · (6-methyl-5-chloro-pyrimidin-4-yl-N-CH(CH₃)-CH₂-O-pyrazole-N-(p-tolyl)) |
| 117-70 | (6-methyl-5-chloro-pyrimidin-4-yl-NH-CH(CH₃)-CH₂-O-pyrazole-N-(p-tolyl)) · citric acid |

TABLE 117-continued the salts of some compounds

| No. | structure |
|---|---|
| 117-71 | 4,5-dichloro-pyrimidine-NH-CH₂CH₂-O-pyrazole-N-C₆H₄-OCF₃ · HCl |
| 117-72 | 4,5-dichloro-pyrimidine-NH-CH₂CH₂-O-pyrazole-N-C₆H₄-OCF₃ · HNO₃ |
| 117-73 | (4,5-dichloro-pyrimidine-NH-CH₂CH₂-O-pyrazole-N-C₆H₄-OCF₃)₂ · H₂SO₄ |
| 117-74 | 4,5-dichloro-pyrimidine-NH-CH₂CH₂-O-pyrazole-N-C₆H₄-OCF₃ · H₃PO₄ |
| 117-75 | 4,5-dichloro-pyrimidine-NH-CH₂CH₂-O-pyrazole-N-C₆H₄-OCF₃ · CH₃COOH |
| 117-76 | 4,5-dichloro-pyrimidine-NH-CH₂CH₂-O-pyrazole-N-C₆H₄-OCF₃ · CF₃COOH |
| 117-77 | 4,5-dichloro-pyrimidine-NH-CH₂CH₂-O-pyrazole-N-C₆H₄-OCF₃ · HOOC-C₆H₄-CH₃ |
| 117-78 | 4-methyl-5-chloro-pyrimidine-NH-CH₂CH₂CH₂-O-pyrazole-N-C₆H₅ · HO₃S-C₆H₄-CH₃ |

TABLE 117-continued the salts of some compounds

| No. | structure |
|---|---|
| 117-79 | 4,5-dichloropyrimidin-6-yl-NH-CH₂CH₂-O-[pyrazole]-N-phenyl-OCF₃ · malic acid |
| 117-80 | F₃CO-phenyl-[pyrazole]-O-CH₂CH₂-N(pyrimidinyl-5,6-diCl) · maleic acid |
| 117-81 | (6-methyl-5-chloropyrimidin-4-yl-NH-CH₂CH₂CH₂-O-[pyrazole]-N-phenyl)₂ · HOOCCOOH |
| 117-82 | 6-methyl-5-chloropyrimidin-4-yl-N(CH(CH₃)CH₂CH₂-O-[pyrazole]-N-phenyl) · CH₃SO₂OH |
| 117-83 | 6-CF₃-5-Cl-pyrimidin-4-yl-N-CH₂CH₂-O-[pyrazole]-N-(3-chlorophenyl) · fumaric acid |
| 117-84 | 5-Cl-6-CF₃-pyrimidin-4-yl-N-CH₂CH₂-O-[pyrazole]-N-(3-chlorophenyl) · citric acid |

Table 118: in general formula I-4C, R₁=Cl, R₂=Br, R₃=R₄=R₅=H, the substituents (R₁₁)n are consistent with those in Table 30 and corresponding to 30-1-30-279 in table 30 in turn, the representative compounds are coded as 118-1-118-279.

Table 119: in general formula I-4C, R₁=Cl, R₂=NH₂, R₃=R₄=R₅=H, the substituents (R₁₁)n are consistent with those in Table 30 and corresponding to 30-1-30-279 in table 30 in turn, the representative compounds are coded as 119-1-119-279.

Table 120: in general formula I-4C, $R_1=Cl$, $R_2=NO_2$, $R_3=R_4=R_5=H$, the substituents $(R_{11})n$ are consistent with those in Table 30 and corresponding to 30-1-30-279 in table 30 in turn, the representative compounds are coded as 120-1-120-279.

Table 121: in general formula I-4C, $R_1=Cl$, $R_2=CHO$, $R_3=R_4=R_5=H$, the substituents $(R_{11})n$ are consistent with those in Table 30 and corresponding to 30-1-30-279 in table 30 in turn, the representative compounds are coded as 121-1-121-279.

Table 122: in general formula I-4C, $R_1=Cl$, $R_2=CH_3$, $R_3=R_4=R_5=H$, the substituents $(R_{11})n$ are consistent with those in Table 30 and corresponding to 30-1-30-279 in table 30 in turn, the representative compounds are coded as 122-1-122-279.

Table 123: in general formula I-4C, $R_1=Cl$, $R_2=OCH_3$, $R_3=R_4=R_5=H$, the substituents $(R_{11})n$ are consistent with those in Table 30 and corresponding to 30-1-30-279 in table 30 in turn, the representative compounds are coded as 123-1-123-279.

Table 124: in general formula I-4C, $R_1=CH_3$, $R_2=Cl$, $R_3=R_4=R_5=H$, the substituents $(R_{11})n$ are consistent with those in Table 30 and corresponding to 30-1-30-279 in table 30 in turn, the representative compounds are coded as 124-1-124-279.

Table 125: in general formula I-4C, $R_1=C_2H_5$, $R_2=Cl$, $R_3=R_4=R_5=H$, the substituents $(R_{11})n$ are consistent with those in Table 30 and corresponding to 30-1-30-279 in table 30 in turn, the representative compounds are coded as 125-1-125-279.

Table 126: in general formula I-4C, $R_1=CHF_2$, $R_2=Cl$, $R_3=R_4=R_5=H$, the substituents $(R_{11})n$ are consistent with those in Table 30 and corresponding to 30-1-30-279 in table 30 in turn, the representative compounds are coded as 126-1-126-279.

Table 127: in general formula I-4F, $R_3=R_4=R_5=H$, the substituents $(R_{11})n$ are consistent with those in Table 30 and corresponding to 30-1-30-279 in table 30 in turn, the representative compounds are coded as 127-1-127-279.

Table128: in general formula I-4G, $R_3=R_4=R_5=H$, $R_{28}=Cl$, the substituents $(R_{11})n$ are consistent with those in Table 30 and corresponding to 30-1-30-279 in table 30 in turn, the representative compounds are coded as 128-1-128-279.

The compounds of the present invention can be prepared according to the following methods. the definition of each substituent is as defined above unless otherwise stated:

The compounds represented by general formula I can be prepared by the following two methods according to the different definition of Y:

(1) When Y is O, according to the conjoint position of oxygen atom and pyrazole ring, the methods to prepare the compounds represented by general formula I-1, I-2 and I-3 are as follows:

The method to prepare the compounds represented by general formula I-1 is as follows:

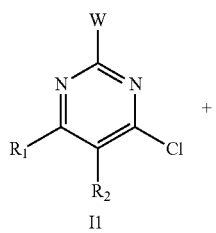

II

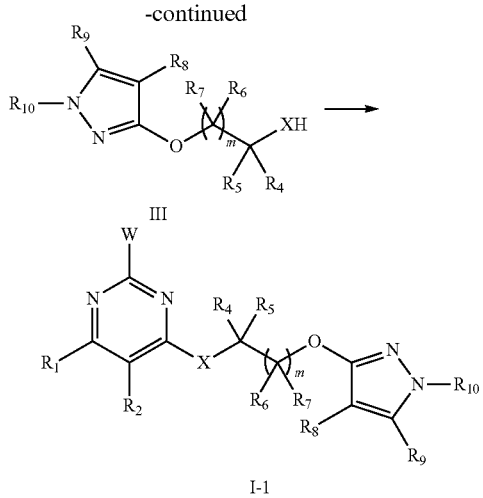

The compounds represented by general formula I-1 can be prepared by reaction of intermediates II and III in the presence of proper base and solvent.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

Intermediates II are commercially available, or are prepared according to the methods described in JP2000007662, U.S. Pat. No. 4,977,264, U.S. Pat. No. 6,090,815, US20040092402, JP09124613, U.S. Pat. No. 5,468,751, U.S. Pat. No. 4,985,426, U.S. Pat. No. 4,845,097, Journal of the American Chemical Society (1957), 79, 1455 or Journal of Chemical Society (1955), p.3478-3481.

The intermediate represented by general formula III is the key intermediate which is used to prepare the the compounds represented by general formula I-1. The preparation method is as follows:

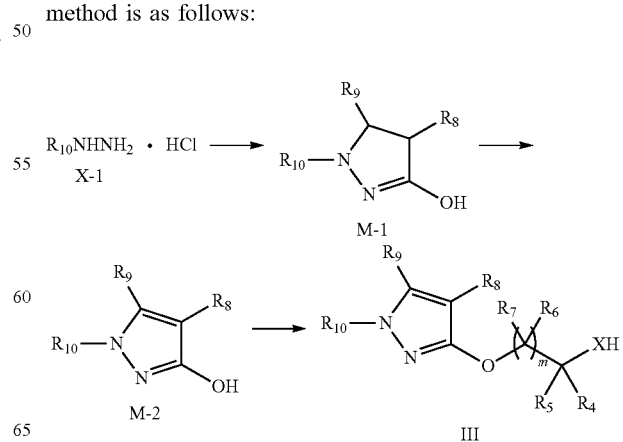

The intermediates represented by general formula M-1 can be prepared by reaction of intermediates represented by general formula X-1 with (un)substituted ethyl acrylate at proper temperature and in proper solvent. The reaction time is in the range of 30 minutes to 20 hours, generally being 1-10 hours, the detailed operation procedures refer to the methods described in CN103588708, WO9703969 and Organic & Biomolecular Chemistry (2011), 9(5), 1443-1453; M-2can be prepared from intermediates represented by general formula M-1 by oxidation reaction, the detailed operation refers to the methods described in DE19652516, WO9703969 and Bulletin of the Korean Chemical Society (2010), 31(11), 3341-3347; The intermediates represented by general formula III can be prepared by reaction of intermediates represented by general formula M-2 and the corresponding halide, the detailed operation refers to the methods described in US20100158860, WO2011133444 and Bioorganic & Medicinal Chemistry (2012), 20(20), 6109-6122.

The sources of intermediates are as follows: the intermediate represented by general formula X-1 are commercially available, or can be prepared according to the conventional method.

The proper reaction temperature is from 0 to 50° C.; The reaction time is in the range of 30 minutes to 20 hours, generally being 0.5-10 hours.

The proper solvent mentioned may be selected from methyl acetate, ethyl acetate, benzene, toluene, xylene, chloroform, dichloromethane, water, tetrahydrofuran, acetonitrile, 1,4-dioxane, DMF, N-methyl pyrrolidone or DMSO and so on.

The proper acid mentioned may be selected from hydrochloric acid, trifluoroacetic acid, sulphuric acid, acetic acid, propionic acid, butyric acid, oxalic acid, adipic acid, 1,10-decanedicarboxylic acid, lauric acid, stearic Acid, fumaric acid, maleic acid, benzoic acid or alizaric acid.

The method to prepare the compounds represented by general formula I-2 is as follows:

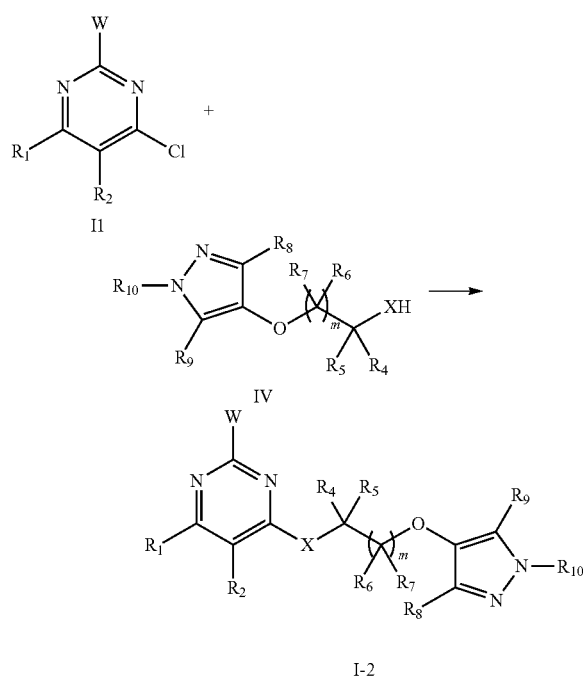

The compounds represented by general formula I-2 can be prepared by reaction of intermediates II and IV in the presence of proper base and solvent.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

The intermediate represented by general formula IV is the key intermediate which is used to prepare the the compounds represented by general formula I-2. The preparation method is as follows:

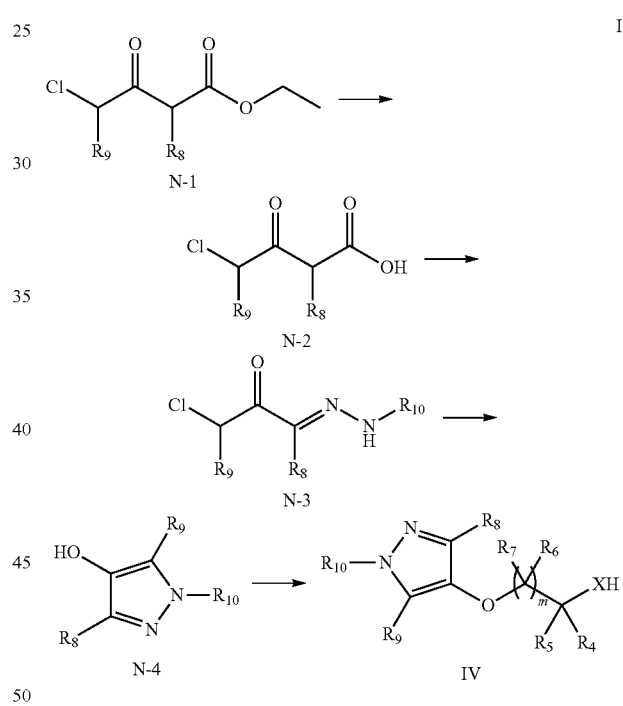

The intermediate N-4 can be prepared from starting material N-1 refer to the methods described in DE3012193, WO2010076553, Organic Preparations and Procedures International (2002), 34(1), 98-102 and Science of Synthesis (2002), 12, 15-225; Journal of Medicinal Chemistry (2016), 59(4), 1370-1387; The preparation method of N-4 to IV is the same as M-2 to III.

The proper solvent mentioned may be selected from methanol, ethanol, tetrahydrofuran, 1,4-dioxane, acetonitrile, toluene, xylene, benzene, DMF, DMSO, acetone or butanone.

The proper solvent may be selected from hydrochloric acid, sulphuric acid or nitric acid.

The proper base mentioned may be selected from sodium hydroxide, potassium hydroxide, sodium methoxide, sodium ethoxide, sodium tert-butoxide or potassium tert-butoxide and so on.

The method to prepare the compounds represented by general formula I-3 is as follows:

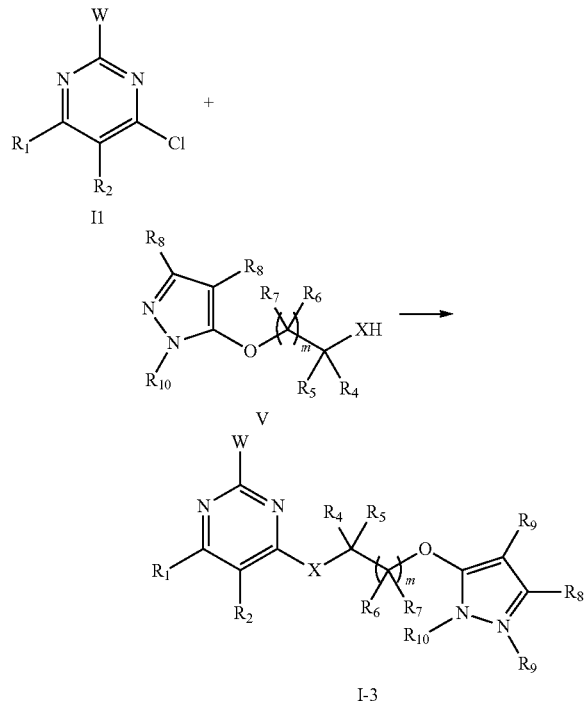

The compounds represented by general formula I-3 can be prepared by reaction of intermediates II and V in the presence of proper base and solvent.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The reaction was carried out in proper solvent and the proper solvent mentioned may be selected from tetrahydrofuran, 1,4-dioxane, acetonitrile, toluene, xylene, benzene, DMF, N-methyl pyrrolidone, DMSO, acetone or butanone and so on.

The proper temperature mentioned is from room temperature to boiling point of the solvent, normal temperature is from 20 to 100° C.

The reaction time is in the range of 30 minutes to 20 hours, generally being 1-10 hours.

The intermediate represented by general formula V is the key intermediate which is used to prepare the the compounds represented by general formula I-3, the preparation method is as follows:

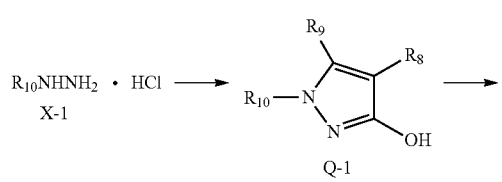

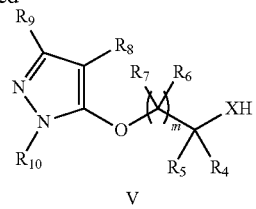

The intermediates Q-1 can be prepared from starting material X-1 refer to the methods described in WO2009069044, WO2000031042, WO2008059370, Bioorganic & Medicinal Chemistry (2006), 14(14), 5061-5071 and so on; The preparation method of Q-1 to V is the same as M-2 to III.

(2) The preparation of the compounds represented by general formula I is as follows when Y is NR3 or S. the detailed operation procedures of the intermediate T refer to the methods described in WO2003049739, WO2000031072 and so on;

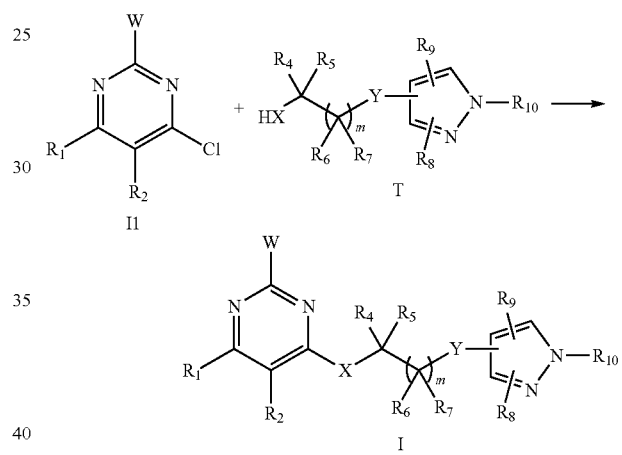

Although the compounds represented by general formula I and some compounds reported in prior art both belong to substituted pyrazole compounds with pyrimidinyl, there are still some obvious differences in structure between them. It is due to these differences in structure that lead to compounds of present invention with better fungicidal and/or insecticidal/acaricidal activities.

The compounds represented by general formula I show excellent activity against both many plant pathogens/diseases in agricultural and other fields and insects/mites. Therefore the technical scheme of the present invention also includes the uses of the compounds represented by general formula I to prepare fungicides, insecticides/acaricides in agricultural or other fields.

The present invention is explained by the following examples of plant diseases, but without being restricted thereby.

The compounds represented by general formula I can be used to control these plant diseases: Oomycete diseases, such as downy mildew (cucumber downy mildew, rape downy mildew, soybean downy mildew, downy mildew of beet, downy mildew of sugarcane, tobacco downy mildew, pea downy mildew, vegetable sponge downy mildew, chinese wax gourd downy mildew, muskmelon downy mildew, chinese cabbage downy mildew, spinach downy mildew, radish downy mildew, grape downy mildew, onion downy mildew), white rust (rape white rust, chinese cabbage white rust), damping-off disease (rape damping-off, tobacco damping-off, tomato damping-off, pepper damping-off, eggplant damping-off, cucumber damping-off, cotton damping-off), pythium rot (pepper soft stale disease, vegetable sponge cottony leak, chinese wax gourd cottony leak), blight (broad bean phytophthora blight, cucumber phytophthora blight, pumpkin phytophthora rot, chinese wax gourd phytophthora blight, watermelon phytophthora blight, muskmelon phytophthora blight, pepper phytophthora blight, chinese chives phytophthora blight, carlic phytophthora blight, cotton phytophthora blight), late blight (potato late blight, tomato late blight) and so on; diseases caused by Deuteromycotina, such as wilt disease (sweet potato fusarium wilt, cotton fusarium wilt disease, sesame wilt disease, fusarium wilt disease of costarbean, tomato fusarium wilt, bean fusarium wilt, cucumber fusarium wilt, vegetable sponge fusarium wilt, pumpkin fusarium wilt, chinese wax gourd fusarium wilt, watermelon fusarium wilt, muskmelon fusarium wilt, pepper fusarium wilt, broad bean fusarium wilt, fusarium wilt disease of rape, fusarium wilt disease of soybean), root rot (pepper root rot, eggplant root rot, bean fusarium root-rot, cucumber fusarium root rot, balsam pear fusarium root rot, cotton black root rot, broad bean thielaviopsis root rot), drooping disease (cotton soreshin, sesame soreshin, pepper rhizoctonia rot, cucumber rhizoctonia rot, chinese cabbage rhizoctonia rot), anthracnose (sorghum anthracnose, cotton anthracnose, kenaf anthracnose, jute anthracnose, flax anthracnose, tobacco anthracnose, mulberry anthracnose, pepper anthracnose, eggplant anthracnose, bean anthracnose, cucumber anthracnose, balsam pear anthracnose, summer squash anthracnose, chinese wax gourd anthracnose, watermelon anthracnose, muskmelon anthracnose, litchi anthracnose), verticillium wilt (cotton verticillium wilt, verticillium wilt of sunflower, tomato verticillium wilt, pepper verticillium wilt, eggplant verticillium wilt), scab (summer squash scab, chinese wax gourd scab, muskmelon scab), gray mold (cotton boll gray mold, kenaf gray mold, tomato gray mold, pepper gray mold, bean gray mold, celery gray mold, spinach gray mold, kiwi fruit gray mold rot), brown spot (cotton brown spot, jute brown spot, beet sercospora leaf spot, peanut brown spot, pepper brown leaf spot, chinese wax gourd corynespora leaf spot, soybean brown spot, sunflower brown spot, pea ascochyta blight, broad bean brown spot), black spot (flax black spot, rape alternaria leaf spot, sesame black spot, sunflower alternaria leaf spot, costarbean alternaria leaf spot, tomato nail head spot, pepper black fruit spot, eggplant black spot, bean leaf spot, cucumber alternaria blight, celery alternaria black leaf spot, carrot alternaria black rot, carrot leaf blight, apple alternaria rot, peanut brown spot), spot blight (tomato septoria leaf spot, pepper septoria leaf spot, celery late blight), early blight (tomato early blight, pepper early blight, eggplant early blight, potato early blight, celery early blight), ring spot (soybean zonate spot, sesame ring spot, bean zonate spot), leaf blight (sesame leaf blight, sunflower leaf blight, watermelon alternaria blight, muskmelon alternaria spot), basal stem rot (tomato basal stem rot, bean rhizoctonia rot), and others (corn northern leaf spot, kenaf damping-off, rice blast, millet black sheath, sugarcane eye spot, cotton aspergillus boll rot, peanut crown rot, soybean stem blight, soybean black spot, muskmelon alternaria leaf blight, peanut web blotch, tea red leaf spot, pepper phyllosticta blight, chinese wax gourd phyllosticta leaf spot, celery black rot, spinach heart rot, kenaf leaf mold, kenaf brown leaf spot, Jute stem blight, soybean cercospora spot, sesame leaf spot, costarbean gray leaf spot, tea brown leaf spot, eggplant cercospora leaf spot, bean cercospora leaf spot, balsam pear cercospora leaf spot, watermelon cercospora leaf spot, jute dry rot, sunflower root and stem rot, bean charcoal rot, soybean target spot, eggplant corynespora leaf spot, cucumber corynespora target leaf spot, tomato leaf mold, eggplant fulvia leaf mold, broad bean chocolate spot) and so on; diseases caused by Basidiomycete, such as rust (wheat stripe rust, wheat stem rust, wheat leaf rust, peanut rust, sunflower rust, sugarcane rust, chinese chives rust, onion rust, millet rust, soybean rust), smut (corn head smut, corn smut, sorghum silk smut, sorghum loose kernel smut, sorghum hard smut, sorghum smut, millet kernel smut, sugarcane smut, bean rust), and others (for example, wheat sheath blight and rice sheath blight) and so on; diseases caused by Ascomycete, such as powdery mildew (wheat powdery mildew, rape powdery mildew, powdery mildew of sesame, powdery mildew of sunflower, beet powdery mildew, eggplant powdery mildew, pea powdery mildew, vegetable sponge powdery mildew, pumpkin powdery mildew, summer squash powdery mildew, chinese wax gourd, muskmelon powdery mildew, grape powdery mildew, broad bean powdery mildew), sclerotinia rot (flax sclertiniose, rape sclertiniose, soybean sclertiniose, peanut sclertiniose, tobacco sclerotinia rot, pepper sclerotinia rot, eggplant sclerotinia rot, bean sclerotinia rot, pea sclerotinia rot, cucumber sclerotinia rot, balsam pear sclerotinia rot, chinese wax gourd sclerotinia rot, watermelon sclerotinia disease, celery stem rot), scab (apple scab, pear scab) and so on.

The compounds represented by general formula I can be used to control these insects: Coleoptera, such as Acanthoscelides spp., Acanthoscelides obtectus, Agrilus planipennis, Agriotes spp., Anoplophora glabripennis, Anthonomus spp., Anthonomus grandis, Aphidius spp., Apion spp., Apogonia spp., Atacnius spretulus, Atomaria linearis, pygmy mangold beetle, Aulacophore spp., Bothynoderes punctiventris, Bruchus spp., Bruchus pisorum, Cacoesia, Cacoesia spp., Callosobruchus maculatus, Carpophilus hemipteras, Cassida vittata, Cerosterna spp., Cerotoma, Cerotoma spp., Cerotoma trifur cata, Ceutorhynchus spp., Ceutorhynchus assimilis, cabbage seedpod weevil, Ceutorhynchus napi, cabbage curculio, Chaetocnema spp., Colaspis spp., Conoderus scalaris, Conoderus stigmosus, Conotrachelus nenuphar, Cotinus nitidis, Green June beetle, Crioceris asparagi, Cryptolestes ferrugincus, rusty grainbeetle, Cryptolestes pusillus, Cryptolestes turcicus Turkish grain beetle, Ctenicera spp., Curculio spp., Cyclocephala spp., Cylindrocpturus adspersus, sunflower stem weevil, Deporaus marginatus, mango leaf-cutting weevil, Dermestes lardarius, Dermestes maculates, Diabrotica spp., Epilachna varivcstis, raustinus cubae, Hylobius pales, pales weevil, Hypera spp., Hypera postica, Hyperdoes spp., Hyperodes weevil, Hypothenemus hampei, Ips spp., engravers, Lasioderma serricorne, Leptinotarsa decemlineata, Liogenys fuscus, Liogenyssuturalis, Lissorhoptrus oryzophilus, Lyctus spp., powder post beetles, Maecolaspis joliveti, Megascelis spp., Melanotus communis, Meligethes spp., Meligethes aeneus, blossom beetle, Melolontha melolontha, Oberea brevis, Oberea linearis, Oryctes rhinoceros, date palm beetle, Oryzaephilus mercator, merchant grain beetle, Oryzaephilus surinamensis, sawtoothed grain beetle, Otiorhynchus spp., Oulema melanopus, cereal leafbeetle, Oulema oryzae, Pantomorus spp., Phyllophaga spp., Phvllophaga cuyabana, Phyllotreta spp., Phynchites spp., Popillia japonica, Prostephanus truncates, larger grain borer, Rhizopertha dominica, lesser grain borer, Rhizotrogus spp., Eurpoean chafer, Rhynchophorus spp., Scolytus spp., Shenophorus spp.

Sitona lincatus, pea leaf weevil, Sitophilus spp., Sitophilus granaries, granary weevil, Sitophilus oryzae, rice weevil, Stegobium paniceum, drugstore beetle, Tribolium spp., Tribolium castaneum, red flour beetle, Tribolium confusum, confused flour beetle, Trogoderma variabile, warehouse beetle and Zabrus tenebioides.

Dermaptera.

Dictyoptera, such as Blattella germanica, German cockroach, Blatta orientalis, Parcoblatta pennylvanica, Periplaneta americana, American cockroach, Periplaneta australoasiae, Australian cockroach, Periplaneta brunnca, brown cockroach, Periplaneta fuliginosa, smokybrown cockroach, Pyncoselus suninamensis, Surinam cockroach and Supella longipalpa, brownbanded cockroach.

Diptera, such as Aedes spp., Agromyza frontella, alfalfa blotch leafminer, Agromyza spp., Anastrepha spp., Anastrepha suspensa, Caribbean fruit fly, Anopheles spp., Batrocera spp., Bactrocera cucurbitae, Bactrocera dorsalis, Ceratitis spp., Ceratitis capitata, Chrysops spp., Cochliomyia spp., Contarinia spp., Culex spp., Dasineura spp., Dasineura brassicae, Delia spp., Delia platura, seedcorn maggot, Drosophila spp., Fannia spp., Fannia canicularis, little house fly, Fannia scalaris, Gasterophilus intestinalis, Gracillia perseae, Haematobia irritans, Hylemyia spp., root maggot, Hypoderma lineatum, common cattle grub, Liriomyza spp., Liriomyza brassica, serpentine leafminer, Melophagus ovinus, Musca spp., muscid fly, Musca autumnalis, face fly, Vusca domestica, house fly, Oestrus ovis, sheep bot fly, Oscinella frit, Pegomyia betae, beet leafminer, Phorbia spp., Psila rosae, carrotrust fly, Rhagoletis cerasi, cherry fruit fly, Rhagoletis pomonella, apple maggot, Sitodiplosis mosellana, orange wheat blossom midge, stomoxys calcitruns, stable fly, Tahanus spp. and Tipula spp.

Hemiptera, such as Acrosternum hilare, green stink bug, Blissus leucopterus, chinch bug, Calocoris norvegicus, potato mirid, Cimex hemipterus, tropical bed bug, Cimex lectularius, bed hug, Daghertus fasciatus, Dichelops furcatus, Dysdercus suturellus, cotton stainer, Edessa meditabunda, Eurygaster maura, cereal bug, Euschistus heros, Euschistus servus, brown stink bug, Helopeltis antonii, Helopeltis theivora, tea blight plantbug, Lagynotomus spp., Leptocorisa oratorius, Leptocorisa varicorni, Lygus spp., plant bug, Lygus hesperus, western tarnished plant bug, Maconellicoccus hirsutus, Neurocolpus longirostris, Nezara viridula, southern green stink bug, PhyLocoris spp., Phytocoris californicus, Phytocoris relativus, Piezodorus guildingi, Poecilocapsus lineatus, fourlined plant bug, Psallus vaccinicola, Pseudacysta perseae, Scaptocoris castanea and Triatoma spp., bloodsuckingconenose bug, kissing bug.

Homoptera, such as Acrythosiphonpisum, pea aphid, Adelges spp., adelgids, Aleurodes proletella, Aleurodicus disperses, Aleurothrixus flecosus, woolly whitefly, Aluacaspis spp., Amrasca bigutella bigutella, Aphrophora spp., leafhopper, Aonidiella aurantii, California red scale, Aphis spp., Aphis gossypii, cotton aphid, Aphis pomi, apple aphid, Aulacorthitm solan, foxglove aphid, Bemisia spp., Bemisia argentifolii, Bemisia tabaci, sweetpotato whitefly, Brachycolus noxius, Russian aphid, Brachycorynclia asparagi, asparagus aphid, Brevennia rehi, Brevicoryne brassicae, Ceroplastes spp., Ceroplastes rubens, red wax scale, Chionaspis spp., Chrysomphalus spp., Coccus spp., Dysaphis plantaginea, rosy apple aphid, Empoasca spp., Eriosoma lanigerum, woolly apple aphid, Icerya purchasi, cottony cushion scale, Idioscopus nitidulus, mango leafhopper, Laodelphax striatellus, smaller brown planthopper, Lepidosaphes spp., Macrosiphum spp., Macrosiphum euphorbiae, potato aphid, Macrosiphum granarium, English grain aphid, Macrosiphum rosae, rose aphid, Macrosteles quadrilineatus, aster leafhopper, Mahanarva frimbiolata, Metopolophium dirhodum, rose grain aphid, Midis longicornis, Myzus persicae, green peach aphid, Nephotettix spp., Nephotettix cinctipes, green leafhopper, Nilaparvata lugens, brown planthopper, Parlatoria pergandii, chaff scale, Parlatoria ziziphi, ebony scale, Peregrinus maidis, corn delphacid, Philaenus spp., Phylloxera vitifoliae, grape phylloxera, Physokermes piceae, spruce bud scale, Planococcus spp., Pseudococcus spp., Pscudococcus brevipes, pine apple mealybug, Quadraspidiotus perniciosus, San Jose scale, Rhapalosiphum spp., Rhapalosiphum maida, corn leaf aphid, Rhapalosiphum padi, oatbird-cherry aphid, Saissetia spp., Saissetia oleae, Schizaphis graminum, greenbug, Sitobion avenge, Sogatella furcifera, white-backed planthopper, Therioaphis spp., Toumeyella spp., Toxoptera spp., Trialeurodes spp., Trialeurodes vaporariorum, greenhouse whitefly, Trialeurodes abutiloneus, bandedwing whitefly, Unaspis spp., Unaspis yanonensis, arrowhead scale and Zulia entreriana.

Hymenoptera, such as Acromyrrmex spp., Athalia rosae, Atta spp., leafcutting ants, Camponotus spp., carpenter ant, Diprion spp., sawfly, Formica spp., Iridomyrmex humilis, Argentineant, Monomorium ssp., Monomorium minumum, little black ant, Monomorium pharaonis, haraoh ant, Neodiprion spp., Pogonomyrmex spp., Polistes spp., paper wasp, Solenopsis spp., Tapoinoma sessile, odorous house ant, Tetranomorium spp., pavement ant, Vespula spp., yellow jacket and Xylocopa spp., carpenter bee.

Isoptera, such as Coptotermes spp., Coptotermes curvignathus, Coptotermes frenchii, Coptotermes formosanus, Formosan subterranean termite, Cornitermes spp., nasute termite, Cryptotermes spp., Heterotermes spp., desert subterranean termite, Heterotermes aureus, Kalotermes spp., Incistitermes spp., Macrotermes spp., fungus growing termite, Marginitermes spp., Microcerotermes spp., harvester termite, Microtermes obesi, Procornitermes spp., Reticulitermes spp., Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis, Reticulitermes virginicus, Schedorhinotermes spp. and Zootermopsis spp.

Lepidoptera, such as Achoea Janata, Adoxophyes spp., Adoxophyes orana, Agrotis spp., Agrotis ipsilon, Alabama argillacea, cotton leafworm, Amorbia cuneana, Amyelosis transitella, navel orangeworm, Anacamptodes defectaria, Anarsia lineatella, peach twig borer, Anomis sabulijera, jute looper, Anticarsia gemmatalis, velvetbean caterpillar, Archips argyrospila) (fruit tree leafroller, Archips rosana, rose leaf roller, Ar gyrotaenia spp., tortricid moths, Argyrotaenia citrana, orange tortrix, Autographa gamma, Bonagota cranaodes, Borbo cinnara, rice leaf folder, Bucculatrix thurberiella, cotton leafperforator, Caloptilia spp., Capua reticulana, Carposina niponensis, peach fruit moth, Chilo spp., Chlumetia transversa, mango shoot borer, Choristoneura rosaceana, oblique banded leaf roller, Chrysodeixis spp., Cnaphalocerus medinalis, grass leafroller, Colias spp., Conpomorpha cramerella, Cossus cossus, Crambus spp., Sod webworms, Cydia funebrana, plum fruit moth, Cydia molesta, oriental fruit moth, Cydia nignicana, pea moth, Cydia pomonella, codling moth, Darna diducta, Diaphania spp., stem borer, Diatr aea spp., stalk borer, Diatraea saccharalis, sugarcane borer, Diatraea grainosella, southwester corn borer, Earias spp., Earias insulata, Egyptian bollworm, Earias vit.ella, rough northern bollworm, Ecdytopopha aurantianum, Elasmopalpus lignosellus, lesser cornstalk borer, Epiphysias postruttana, light brown, apple moth, Ephestia spp., Ephestia cautella, almond moth, Ephestia elutella, tobbaco moth, Ephestia kuehniella, Mediterranean flour moth, Epimeces spp, Epinotia aporema, Erionota thrax, banana skipper, Eupoecilia ambiguella, grape berry moth, Euxoa auxiliaris, army cutworm, Feltia spp., Gortyna spp., Grapholita molesta, oriental fruit moth, Hedylepta indicata, bean leaf webber, Helicoverpa spp., Helicoverpa armigera, cotton bollworm, Helicoverpa zea, Heliothis spp., Heliothis virescens, tobacco budworm, Hellula undalis, cabbage webworm, Indarbela spp. Keiferia lycopersicella, tomato pinworm, Leucinodes orbonalis, eggplant fruit borer, Leucoptera malifoliella, Lithocollectis spp., Lobesia botrana, grape fruit moth, Loxagrotis spp., Loxagrotis albicosta, western bean cutworm, Lymantria dispar, gypsy moth, Lyonetiaclerkella, apple leafminer, Mahasena corbetti, oil palm bagworm, Malacosoma spp., tent caterpillars, Mamestra brassicae, cabbage armyworm, Maruca testulalis, Metisa plana, Mythimna unipuncta, true armyworm, Neoleucinodes elegantalis, small tomato borer, Nymphula depunctalis, rice caseworm, Operophthera brumata, winter moth, Ostrinia nubilalis, European corn borer, Oxydia vesulia, Pandemis cerasana, common currant tortrix, Pandemis heparana, brown apple tortrix, Papilio demodocus, Pectinophora gossypiella, pink bollworm, Peridroma spp., Peridroma saucia, variegated cutworm, Perileucoptera coffeella, white coffee leafminer, Phthorimaea operculella, potato tuber moth, Phyllocnisitis citrella, Phyllonorycter spp., Pieris rapae, imported cabbageworm, Plathypena scabra, Plodia interpunctella, Indian meal moth, Plutella xylostella, diamondback moth, Polychrosis viteana, grape berry moth, Prays endocarps, Prsys oleae, olive moth, Pseudaletia spp., Pseudaletia unipunctata, Pseudoplusia includens, soybean looper, Rachiplusia nu, Scirpophaga incertulas, Sesamia spp., Sesamia inferens, pink rice stemborer, Sesamia nonagrioides, Setora nitens, Sitotroga cerealella, Angoumois grain moth, Sparganothis pilleriana, Spodoptera spp., Spodoptera exigua, beet armyworm, Spodoptera fugiperda, fall armyworm, Spodoptera oridania, southern armyworm, Synanthedon spp., Thecla basilides, Thermisia gemmatalis, Tineola bisselliella, webbing clothes moth, Trichoplusia ni, cabbage looper, Tuts absoluta, Yponomeuta spp., Zeuzeracoffeae, red branch borer and Zeuzera pyrina, eopard moth.

Mallophaga, chewing lice, such as Bovicola ovis, sheep biting louse, Menacanthus stramineus, chicken body louse and Menopon gallinea, common hen house, Orthoptera, such as Anabrus simplex, Mormon cricket, Gryllotalpidae, mole cricket, Locusta migratoria, Melanoplus spp., Microcentrum retinerve, angular winged katydid, Pterophylla spp., histocerca gregaria, Scudderia furcata, fork tailed bush katydid and Valanga nigricorni, sucking louse, such as Haematopinus spp., Linognathus ovillus, sheep louse, Pediculus humanus capitis, Pediculus humanus humanus and Pthirus pubis, crab louse.

Siphonaptera, such as Ctenocephal ides canis, dog flea, Ctenocephalides felis, cat flea and Pulex irritanshuman flea.

Thysanoptera, such as Frankliniella fusca, tobacco thrip, Frankliniella occidentalis, western flower thrips, Frankliniella shultzei, Frankliniella williamsi, corn thrip, Ileliothrips haemorrhaidalis, greenhouse thrip, Riphiphorothrips cruentatus, Scirtothrips spp, Scirtothrips cirri, citrus thrip, Scirtothrips dorsalis, yellow tea thrips, Taeniothrips rhopalantennalis and Thrips spp.

Thysanura, bristletail, such as Lepisma spp, silverfish and Thermobia spp.

Acarina, mite and tick, such as Acarapsis woodi, tracheal mite of honeybee, Acarus spp., Acarus siro, grain mite, Aceria mangiferae, mango bud mite, Aculops spp., Aculops lycopersici, tomato russet mite, Aculops pelekasi, Aculus pelekassi, Aculus schlechtendali, apple rust mite, Amblyomma amcricanum, lone star tick, Boophilus spp., Brevipalpus obovatus, privet mite, Brevipalpus phoenicis, red and black flat mite, Demodex spp., mange mites, Dermacentor spp., Dermacentor variabilis, american dog tick, Dermatophagoides pteronyssinus, house dust mite, Eotetranycus spp., Eotetranychus carpini, yellow spider mite, Epitimerus spp., Eriophyes spp., I ; odes spp., Metatetranycus spp., Notoedres cati, Oligonychus spp., Oligonychus coffee, Oligonychus ilicus, southernred mite, anonychus spp., Panonychus cirri, citrus red mite, Panonychus ulmi, European red mite, Phyllocoptruta oleivora, citrus rust mite, Polyphagotarsonemun latus, broad mite, Rhipicephalus sanguineus, brown dog tick, Rhizoglyphus spp., bulb mite, Sarcoptes scabiei, itch mite, Tegolophus perseaflorae, Tetranychus spp., Tetranychus urticae, twospotted spider mite and Varroa destructor.

Nematoda, such as Aphelenchoides spp., bud and leaf & pine wood nematode, Belonolaimus spp., sting nematodes, Criconemella spp., ring nematodes, Dirofilaria immitis, dog heartworm, Ditylenchus spp., Heterodera spp., cyst nematode, Heterodera zeae, corn cyst nematode, Hirschmanniella spp., root nematodes, Hoplolaimus spp., lance nematodes, Meloidogyne spp., Meloidogyne incognita, Onchocerca volvulus, hook-tail worm, PraLylenchus spp., lesion nematode, Radopholus spp., burrowing nematode and Rotylenchus reniformis, kidney-shaped nematode.

Symphyla, such as Scutigerella immaculata.

Thanks to their positive characteristics, the compounds mentioned above can be advantageously used in protecting crops of farming and gardening, domestic and breeding animals, as well as environments frequented by human beings from pathogens, insects and pest mites.

In order to obtain desired effect, the dosage of the compounds to be applied can vary with various factors, for example, the used compound, the protected crop, the type of harmful organism, the degree of infestation, the climatic conditions, the application method and the adopted formulation.

The dosage of compounds in the range of 10 g to 5 kg per hectare can provide a sufficient control.

A further object of the present invention also includes fungicidal, insecticidal/acaricidal compositions containing the compounds having general formula I as active ingredient, and the weight percentage of the active ingredient in the composition is 0.5-99%. The fungicidal, insecticidal/acaricidal compositions also include the carrier being acceptable in agriculture, forestry and public health.

The compositions of the present invention can be used in the form of various formulations. Usually, the compounds having general formula I as active ingredient can be dissolved in or dispersed in carriers or made to a formulation so that they can be easily dispersed as an fungicide or insecticide. For example: these chemical formulations can be made into wettable powder, oil miscible flowable, aqueous suspension, aqueous emulsion, aqueous solution or emulsifiable concentrates and so on. Therefore, in these compositions, at least a liquid or solid carrier is added, and usually suitable surfactant(s) can be added when needed.

Still also provided by the present invention are the application methods for controlling phytopathogenic fungi, insects, pest mites which is to apply the compositions of the present invention to the phytopathogenic fungi or their growing loci. The suitable effective dosage of the compounds of the present invention is usually within a range of 10 g/ha to 1000 g/ha, preferably from 20 g/ha to 500 g/ha.

For some applications, one or more other fungicides, insecticides/acaricides, herbicides, plant growth regulators or fertilizer can be added into the fungicidal, insecticidal/acaricidal compositions of the present invention to make additional merits and effects.

It should be noted that variations and changes are permitted within the claimed scopes in the present invention.

DETAILED DESCRIPTION OF THE INVENTION

The present invention is illustrated by the following examples, but without being restricted thereby. (All raw materials are commercially available unless otherwise specified.)

PREPARATION EXAMPLES

Example 1

The Preparation of Intermediate 4,5-dichloro-6-methylpyrimidine

1) The Preparation of 4-hydroxyl-5-chloro-6-methylpyrimidine

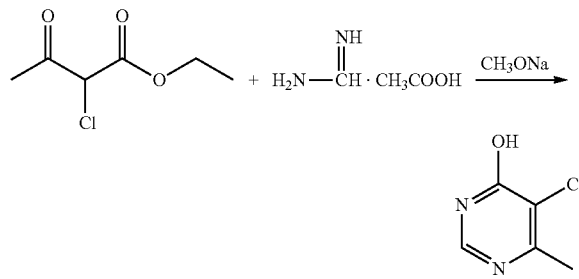

A solution of 8.80 g (0.16 mol) of CH$_3$ONa in methanol was added slowly to a solution of 11.30 g (0.11 mol) of formimidamideacetate in 50 mL of methanol at room temperature under stirring, the mixture was stirred for another 2 h after addition at room temperature. Followed by addition of 11.17 g (0.068 mol) of ethyl 2-chloro-3-oxobutanoate, the mixture was continued stirring for another 5-7 h at room temperature. After the reaction was over by Thin-Layer Chromatography monitoring, the reaction mixture was concentrated under reduced pressure and pH was adjusted to 5-6 with HCl, and then filtered to afford orange-yellow solid, the water phase was extracted with ethyl acetate (3×50 mL), dried over anhydrous magnesium sulfate, filtered and then concentrated under reduced pressure. The residue was dissolved to 50 ml of ethyl acetate, stand overnight to obtain 6.48 g as orange-yellow solid with yield of 66%. m.p. 181~184° C.

2) The Preparation of Intermediate 4,5-dichloro-6-methylpyrimidine

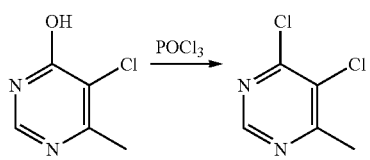

50 ml of POCl$_3$ was added dropwise to a solution of 14.5 g (0.1 mol) of 4-hydroxyl-5-chloro-6-methylpyrimidine in 50 mL of toluene, the mixture was refluxed for 5-7 h after addition. After the reaction was over by Thin-Layer Chromatography monitoring, the reaction mixture was concentrated under reduced pressure to remove toluene and extra POCl$_3$, and then poured into ice water. The water phase was extracted with ethyl acetate (3×50 mL), the organic phases were merged, dried over anhydrous magnesium sulfate, filtered and then concentrated under reduced pressure. The residue was purified through silica column (ethyl acetate/petroleum ether=1:5, as an eluent) to give14.43 g as yellow liquid with yield of 88.5%.

Example 2

The Preparation of Intermediate 4,5-dichlorothieno[2,3-d]pyrimidine

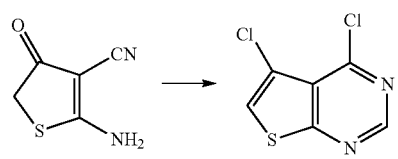 [SMILES: N#CC1=C(N)SCC1=O ; Clc1csc2ncnc(Cl)c12]

To a solution of2-amino-4-oxo-4,5-dihydrothiophene-3-carbonitrile (70 g, 0.5 mol) dissolved in 250 mL phosphoryl trichloridein an ice-bath was added38 ml DMF for about 30 min, and reacted for 1 h at the room temperature, then heated to 75° C. for 3 h. After the reaction was over by Thin-Layer Chromatography monitoring, the mixture was cooled to the room temperature and poured into ice-water, the water phase was extracted with ethyl acetate (3×80 mL), the organic phases were merged, filtered to get 89.1 g 4,5-dichlorothieno[2,3-d]pyrimidine as dark-gray solid with yield of 86.9%, the m.p. is 160-161° C. .

Example 3

The Preparation of Intermediate 4-chloroquinazoline

1) The Preparation of Intermediate quinazolin-4(3H)-one

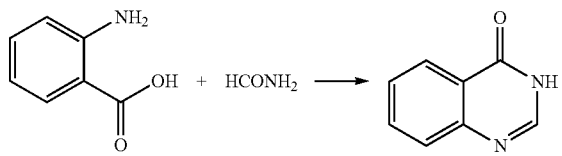

2-aminobenzoic acid (13.7 g, 0.1 mol) and formamide20 ml were placed in a 250 ml three-necked flask, then heated to 140° C. and reacted for 4-10 hours, and monitored by TLC (Thin-Layer Chromatography) until the reaction was over. 80 ml water was added under the stirring condition when the solution was cooled to 100° C., then cooled to the room temperature, filtered and washed the solid with anhydrous diethyl ether to get 10.96 g quinazolin-4(3H)-one as brown solid with yield of 75.1%.

2) The Preparation of Intermediate 4-chloroquinazoline

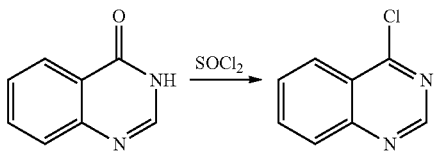

Quinazolin-4(3H)-one(14.6 g, 0.1 mol) was dissolved in 50 mL sulfuryl dichloride, and then heated to reflux for 4-6 h. After the reaction was over by Thin-Layer Chromatography monitoring, the mixture was poured into ice water and stirred for about 30 min, filtered and washed the solid with anhydrous diethyl ether to get 10.96 g 4-chloroquinazoline as brown solid with yield of 92.7%.

Example 4

The Preparation of Intermediate 2-(1-(4-chlorophenyl)-1H-pyrazol-3-yloxy)ethanamine hydrochloride 1) The Preparation of N-Boc-2-bromoethylamine

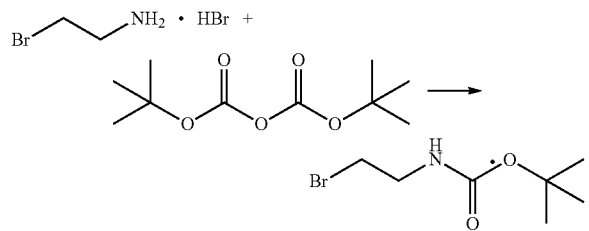

To a solution of 2-bromoethylamine hydrobromide 20.5 g (0.1 mol) and sodium bicarbonate10.08 g (0.12 mol) in 80 mL tetrahydrofuran and 50 ml water was dropwise added di-tert-butyl dicarbonate21.80 g (0.1 mol) at room temperature, then the reaction mixture was continued stirring for 4-10 hrs, and monitored by TLC (Thin-Layer Chromatography) until the reaction was over, the excessive solvent was evaporated under reduced pressure. Then the mixture was poured into (3×50 mL) of ethyl acetate to separate the organic layer, the organic phase was washed with 50 mL of brine, dried and evaporated under reduced pressure to obtain 21.84 g target intermediate as colourless oil with yield of 97.5%.

2) The Preparation of tert-butyl 2-(1-(2-chlorophenyl)-1H-pyrazol-3-yloxy)ethylcarbamate

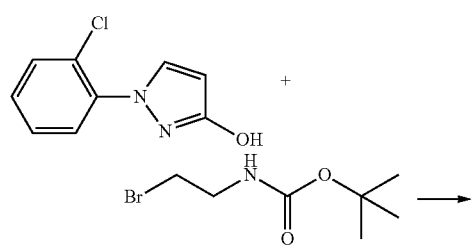

-continued

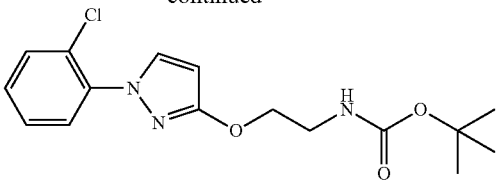

To a solution of 2.24 g (0.01 mol) tert-butyl 2-bromoethylcarbamate and 1.94 g (0.01 mol) 1-(2-chlorophenyl)-1H-pyrazol-3-ol (refer to Organic Preparations and Procedures International, 34(1), 98-102; 2002) in 50 mL butanone was added 2.76 g (0.02 mol) potassium carbonate. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3 ×50 mL) ethyl acetate to separate the organic layer, the organic phase was washed with 50 mL of brine, dried and evaporated under reduced pressure, the residual was purified via silica column (ethyl acetate/petroleum ether=1:6, as an eluent) to obtain 2.73 g tert-butyl 2-(1-(4-chlorophenyl)-1H-pyrazol-3-yloxy)ethylcarbamate as yellow solid with yield of 81.1%.

3) The Preparation of 2-(1-(2-chlorophenyl)-1H-pyrazol-3-yloxy)ethanamine hydrochloride

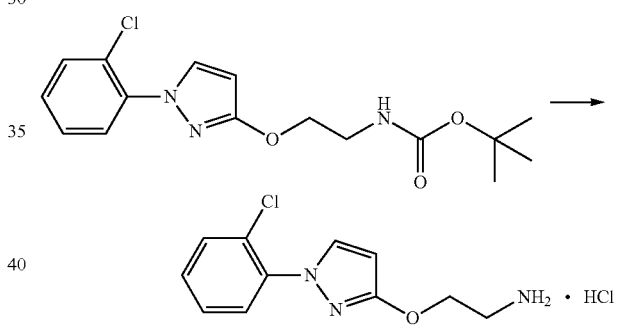

To a solution of tert-butyl 2-(1-(2-chlorophenyl)-1H-pyrazol-3-yloxy)ethylcarbamate 3.37 g (0.01 mol) in 50 mL ethyl acetate was dropwise added 6 mL concentrated hydrochloric acid. The solid was dissolved, the reaction mixture stir for4-5 hours,and monitored by TLC (Thin-Layer Chromatography) until the reaction was over, the excessive solvent was evaporated under reduced pressure. Then the mixture was poured into 10 mL of dichloromethane to stir for half an hour and filtered to give 2.16 g target intermediate as white solid.

Example 5

The Preparation of the Compound 31-19

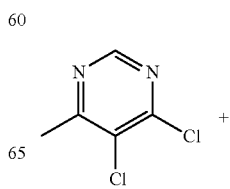

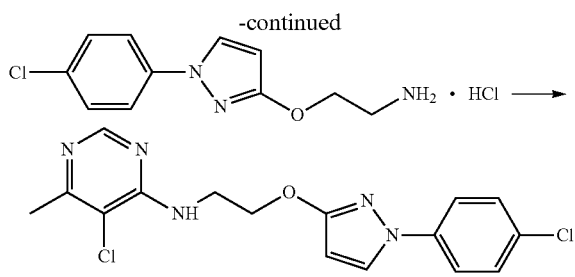

To a solution of 1.62 g (0.01 mol) 4,5-dichloro-6-methylpyrimidine and 2.74 g (0.01 mol) 2-(1-(4-chlorophenyl)-1H-pyrazol-3-yloxy)ethanaminehydrochloride in 50 mL toluene was added 4.45 g (0.022 mol) triethylamine. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:4, as an eluent, boiling range 60-90° C.) to obtain 2.90 g compound 31-19 as white solid with yield of 79.9%.

$^1$H-NMR (300 MHz, internal standard: TMS, solvent: CDCl$_3$) δ(ppm):2.44(3H, s), 3.90-3.98(2H, q), 4.48(2H, t), 5.93(1H, d), 5.94(1H, t), 7.37(2H, dd), 7.52(2H, dd), 7.71 (1H, d), 8.39(1H,s).

Example 6

The Preparation of the Compound 40-17

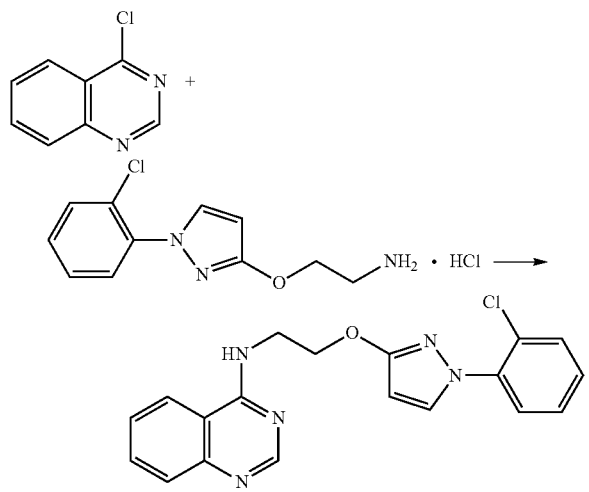

To a solution of 1.64 g (0.01 mol) 4-chloroquinazoline and 2.74 g (0.01 mol) 2-(1-(2-chlorophenyl)-1H-pyrazol-3-yloxy)ethanaminehydrochloride in 50 mL toluene was added 4.45 g (0.022 mol) triethylamine. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:4, as an eluent, boiling range 60-90° C.) to obtain 2.61 g compound 40-17 as white solid with yield of 70.1%. m.p. 186.6° C.

$^1$H-NMR (300 MHz, internal standard: TMS, solvent: CDCl$_3$) δ(ppm): 8.65(s, 1H, Quinazoline-3-H), 7.73(d, J=2.4 Hz, 1H, Pyrazole-5-H), 7.40-7.72 (m, 5H, Ph-3,4,5, 6-5H), 7.40-7.72(m, 4H, Quinazoline-5,6,7,8-4H), 5.97(d, J=2.4 Hz, 1H, Pyrazole-4-H), 5.90(s, 1H, NH), 4.63(t, 2H, O—CH$_2$), 4.06(m, 2H, N—CH$_2$).

Example 7

The Preparation of the Compound 44-19

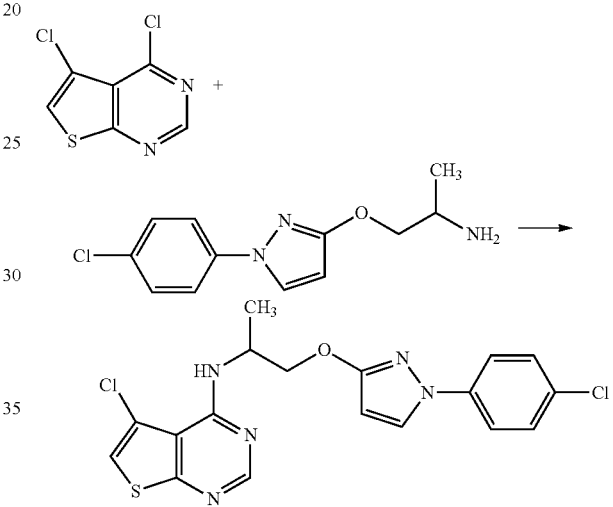

To a solution of 0.41 g (0.002 mol) 4,5-dichlorothieno[2,3-d]pyrimidine and 0.51 g (0.002 mol) 1-(1-(4-chlorophenyl)-1H-pyrazol-3-yloxy)propan-2-amine in 50 mL toluene was added 0.45 g (0.011 mol) triethylamine. The reaction mixture was continued stirring and heating to reflux for 4-10 hours, and monitored by TLC (Thin-Layer Chromatography) until the reaction was over, the excessive solvent was evaporated under reduced pressure. then the mixture was poured into (3×50 mL) ethyl acetate to separate the organic layer, the organic phase was washed with 50 mL of brine, dried and evaporated under reduced pressure, the residual was purified via silica column (ethyl acetate/petroleum ether=1:4, as an eluent, boiling range 60-90° C.) to obtain 0.53 g compound 44-19 as white solid with yield of 63.7%.

$^1$H-NMR (300 MHz, internal standard: TMS, solvent: CDCl$_3$) δ(ppm): 1.48(3H, d), 4.40-4.46(2H, m), 4.85(1H, q), 5.95(1H, d), 7.03(1H, d), 7.26(1H, s), 7.48(2H, d), 7.51(2H, d), 7.90(1H, d), 8.47(1H, s).

Other compounds of the present invention were prepared according to the above examples.

Physical properties and $^1$HNMR spectrum ($^1$HNMR, 300 MHz, internal standard: TMS, ppm) of some compounds of this invention are as follows:

Compound 30-1-4: m.p. 152.9° C. δ(CDCl$_3$) 8.29(s, 1H, Pyrimidine-H), 7.68(d, J=2.4 Hz, 1H, Pyrazole-5-H),7.51-7.56(m, 2H, Ph-2,6-2H), 7.08-7.15(m, 2H, Ph-3,5-2H), 5.91

(d, J=2.4 Hz, 1H, Pyrazole-4-H), 5.56(s, 1H, NH), 4.49(t, 2H, O—CH$_2$), 3.91-3.96(m, 2H, N—CH$_2$), 2.05(s, 3H, CH$_3$).

Compound 30-1-19: m.p. 156.1° C. δ(CDCl$_3$) 8.30(s, 1H, Pyrimidine-H), 7.72(d, J=2.4 Hz, 1H, Pyrazole-5-H), 7.52 (d, J=9 Hz, 2H, Ph-2,6-2H), 7.39(d, J=9 Hz, 2H, Ph-3,5-2H), 5.93(d, J=2.4 Hz, 1H, Pyrazole-4-H), 5.50(s, 1H, NH), 4.49(t, 2H, O—CH$_2$), 3.94(m, 2H, N—CH$_2$), 2.06(s,3H, CH$_3$).

Compound 30-1-21: m.p. 126.8° C. δ(CDCl$_3$) 8.28(s, 1H, Pyrimidine-H), 7.73(d, J=2.7 Hz, 1H, Pyrazole-5-H), 7.49-7.51 (m, 2H, Ph-3,6-2H), 7.34(d, 1H, Ph-5-H), 5.94(d, J=2.7 Hz, 1H, Pyrazole-4-H), 5.64(s, 1H, NH), 4.47(t, 2H, O—CH$_2$), 3.93(m, 2H, N—CH$_2$), 2.04(s,3H, CH$_3$).

Compound 30-1-25: m.p. 172.7° C. δ(CDCl$_3$) 8.31(s, 1H, Pyrimidine-H), 7.73(d, J=2.7 Hz, 1H, Pyrazole-5-H), 7.50 (d, 2H, Ph-2,6-2H), 7.20(s, 1H, Ph-4-H), 5.96(d, J=2.7 Hz, 1H, Pyrazole-4-H), 5.40(s, 1H, NH), 4.50(t, 2H, O—CH$_2$), 3.94-3.98(m, 2H, N—CH$_2$), 2.11(s, 3H, CH$_3$).

Compound 30-1-30: m.p. 175.9° C. δ(CDCl$_3$) 8.27(s, 1H, Pyrimidine-H), 7.47(s, 2H, Ph-3,5-2H), 7.34(d, J=2.7 Hz, 1H, Pyrazole-5-H), 5.96(d, J=2.7 Hz, 1H, Pyrazole-4-H), 5.70(s, 1H, NH), 4.45(t, 2H, O—CH$_2$), 3.88-3.92(m, 2H, N—CH$_2$), 2.06(s, 3H, CH$_3$).

Compound 30-1-49: m.p. 170.8° C. δ(CDCl$_3$) 8.31(s, 1H, Pyrimidine-H), 7.82(d, J=2.7 Hz, 1H, Pyrazole-5-H), 7.65-7.73(d, 4H, PhH),6.00(d, J=2.7 Hz, 1H, Pyrazole-4-H), 5.34(s, 1H, NH), 4.51(t, 2H, O—CH$_2$), 3.93-3.99(m, 2H, N—CH$_2$), 2.09(s, 3H, CH$_3$).

Compound 30-1-57: m.p. 137.8° C. δ(CDCl$_3$) 8.29(s, 1H, Pyrimidine-H), 7.70(d, J=2.4 Hz, 1H, Pyrazole-5-H), 7.45 (d, J=8.4 Hz, 2H, Ph-2,6-2H), 7.22(d, J=8.4 Hz, 2H, Ph-3,5-2H), 5.89(d, J=2.4 Hz, 1H, Pyrazole-4-H), 5.70(s, 1H, NH), 4.51(t, 2H, O—CH$_2$), 3.90-3.95(m, 2H, N—CH$_2$), 2.37(s, 3H, PhCH$_3$), 2.03(s, 3H, CH$_3$).

Compound 30-1-78: oil. δ(CDCl$_3$) 8.30(s, 1H, Pyrimidine-H), 7.68(d, J=2.4 Hz, 1H, Pyrazole-5-H), 7.51-7.60(m, 2H, Ph-2,6-2H),7.26-7.33(m, 2H, Ph-3,5-2H), 5.93(d, J=2.4 Hz, 1H, Pyrazole-4-H), 5.46(s, 1H, NH),4.49(t, 2H, O—CH$_2$), 3.92-3.97(m, 2H, N—CH$_2$), 2.07(s, 3H, CH$_3$).

Compound 30-2-19: m.p. 111.9° C. δ(CDCl$_3$) 8.17(s, 1H, Pyrimidine-H), 7.72(d, J=2.7 Hz, 1H, Pyrazole-5-H), 7.53 (d, J=6.9 Hz, 2H, Ph-2,6-2H), 7.38(d, J=7.9 Hz, 2H, Ph-3,5-2H), 6.07(s, 1H, NH), 5.92(d, J=2.4 Hz, 1H, Pyrazole-4-H), 4.48(t, 2H, O—CH$_2$), 3.92(m, 2H, N—CH$_2$), 3.74(s,3H, CH$_3$).

Compound 30-3-19: oil. δ(CDCl$_3$) 10.35(s, 1H, CHO), 8.45(s, 1H, Pyrimidine-H), 7.70(d, J=2.7 Hz, 1H, Pyrazole-5-H), 7.51 (d, J=9.3 Hz, 2H, Ph-2,6-2H), 7.37(d, J=9.3 Hz, 2H, Ph-3,5-2H), 6.00(s, 1H, NH), 5.93(d, J=2.7 Hz, 1H, Pyrazole-4-H), 4.48(t, 2H, O—CH$_2$), 4.05(m, 2H, N—CH$_2$).

Compound 30-4-19: m.p. 143.7° C. δ(CDCl$_3$) 8.30(s, 1H, Pyrimidine-H), 7.72(d, J=2.4 Hz, 1H, Pyrazole-5-H), 7.52 (d, J=8.7 Hz, 2H, Ph-2,6-2H), 7.38(d, J=8.7 Hz, 2H, Ph-3,5-2H), 6.29(s, 1H, NH), 5.93(d, J=2.7 Hz, 1H, Pyrazole-4-H), 4.50(t, 2H, O—CH$_2$), 3.94(m, 2H, N—CH$_2$).

Compound 31-4: m.p. 139.2° C. δ(CDCl$_3$) 8.38(s, 1H, Pyrimidine-H), 7.67(d, J=2.4 Hz, 1H, Pyrazole-5-H), 7.51-7.56(m, 2H, Ph-2,6-2H),7.07-7.13(m, 2H, Ph-3,5-2H), 6.01 (s, 1H, NH), 5.91(d, J=2.4 Hz, 1H, Pyrazole-4-H), 4.48(t, 2H, O—CH$_2$), 3.93-3.95(m, 2H, N—CH$_2$), 2.43(s,3H, CH$_3$).

Compound 31-18: m.p. 146.7° C. δ(CDCl$_3$) 8.39(s, 1H, Pyrimidine-H), 7.73(d, J=2.4 Hz, 1H, Pyrazole-5-H), 7.63 (s, 1H, Ph-2-H), 7.43(d, 1H, Ph-6-H), 7.33(t, 1H, Ph-5-H), 7.19(d, 1H, Ph-4-H), 5.96(s, 1H, NH), 5.94(d, J=2.4 Hz, 1H, Pyrazole-4-H), 4.50(t, 2H, O—CH$_2$), 3.95(m, 2H, N—CH$_2$), 2.44(s,3H, CH$_3$).

Compound 31-21: m.p. 155.6° C. δ(CDCl$_3$) 8.37(s, 1H, Pyrimidine-H), 7.73(d, J=2.7 Hz, 1H, Pyrazole-5-H), 7.53 (s, 1H, Ph-3-H), 7.50(d, J=1.8 Hz, 1H, Ph-6-H), 7.34(d, J=1.8 Hz, 1H, Ph-5-H), 6.09(s, 1H, NH), 5.94(d, J=2.7 Hz, 1H, Pyrazole-4-H), 4.46(t, 2H, O—CH$_2$), 3.93(m, 2H, N—CH$_2$), 2.44(s,3H, CH$_3$).

Compound 31-23: oil. δ(CDCl$_3$) 8.37(s, 1H, Pyrimidine-H), 7.31-7.46(m, 4H, Pyrazole-5-H, PhH), 6.12(s, 1H, NH), 5.96(d, 1H, Pyrazole-4-H), 4.45(t, 2H, O—CH$_2$), 3.89-3.95 (m, 2H, N—CH$_2$), 2.45(s, 3H, CH$_3$).

Compound 31-25: m.p. 144.1° C. δ(CDCl$_3$) 8.40(s, 1H, Pyrimidine-H), 7.71(d, J=2.7 Hz, 1H, Pyrazole-5-H), 7.49-7.51(m, 2H, Ph-2,6-2H), 7.18(s, 1H, Ph-4-H),5.96(d, J=2.7 Hz, 1H, Pyrazole-4-H), 5.92(s, 1H, NH),4.49(t, 2H, O—CH$_2$), 3.94-3.96(m, 2H, N—CH$_2$), 2.45(s, 3H, CH$_3$).

Compound 31-30: oil. δ(CDCl$_3$) 8.37(s, 1H, Pyrimidine-H), 7.46(s, 2H, Ph-3,5-2H), 7.33(d, J=2.4 Hz, 1H, Pyrazole-5-H), 6.06(s, 1H, NH), 5.96(d, J=2.4 Hz, 1H, Pyrazole-4-H), 4.43(t, 2H, O—CH$_2$), 3.89-3.95(m, 2H, N—CH$_2$), 2.46(s, 3H, CH$_3$).

Compound 31-49: m.p. 187.0° C. δ(CDCl$_3$) 8.39(s, 1H, Pyrimidine-H), 7.80(d, J=2.4 Hz, 1H, Pyrazole-5-H), 7.69(s, 4H, PhH), 6.00(d, J=2.4 Hz, 1H, Pyrazole-4-H), 5.91(s, 1H, NH), 4.50(t, 2H, O—CH$_2$), 3.92-3.98(m, 2H, N—CH$_2$), 2.44(s, 3H, CH$_3$).

Compound 31-57: m.p. 127.3° C. δ(CDCl$_3$) 8.38(s, 1H, Pyrimidine-H), 7.69(d, J=2.4 Hz, 1H, Pyrazole-5-H), 7.46 (d, J=8.7 Hz, 2H, Ph-2,6-2H), 7.19(d, J=8.7 Hz, 2H, Ph-3,5-2H), 6.04(s, 1H, NH), 5.89(d, J=2.4 Hz, 1H, Pyrazole-4-H), 4.48(t, 2H, O—CH$_2$), 3.91-3.96(m, 2H, N—CH$_2$), 2.43 (s, 3H, CH$_3$), 2.36(s, 3H, PhCH$_3$).

Compound 31-69: m.p. 171.0° C. δ(CDCl$_3$) 8.39(s, 1H, Pyrimidine-H), 7.81(d, J=2.4 Hz, 1H, Pyrazole-5-H), 7.62-7.70 (m, 4H, Ph-2,3,5,6-4H), 5.98(d, J=2.4 Hz, 1H, Pyrazole-4-H), 5.95(s, 1H, NH), 4.50(t, 2H, O—CH$_2$), 3.96(m, 2H, N—CH$_2$), 2.43(s,3H, CH$_3$).

Compound 31-78: m.p. 134.7° C. δ(CDCl$_3$) 8.39(s, 1H, Pyrimidine-H), 7.72(d, J=2.4 Hz, 1H, Pyrazole-5-H), 7.58-7.62(m, 2H, Ph-2,6-2H),7.26-7.29(m, 2H, Ph-3,5-2H), 5.96 (s, 1H, NH)5.94(d, J=2.4 Hz, 1H, Pyrazole-4-H), 4.49(t, 2H, O—CH$_2$), 3.92-3.98(m, 2H, N—CH$_2$), 2.44(s, 3H, CH$_3$).

Compound 32-1: m.p. 92.2° C. δ(CDCl$_3$) 8.43(s, 1H, Pyrimidine-H), 7.75(d, J=2.7 Hz, 1H, Pyrazole-5-H), 7.59 (d, J=8.4 Hz, 2H, Ph-2,6-2H), 7.41(m, 2H, Ph-3,5-2H), 7.22(m, 1H, Ph-4-H), 6.05(s, 1H, NH), 5.92(d, J=2.7 Hz, 1H, Pyrazole-4-H), 4.50(t, 2H, O—CH$_2$), 3.95(m, 2H, N—CH$_2$), 2.76(m, 2H, CH$_2$), 1.24(t,3H, CH$_3$).

Compound 32-4: m.p. 123.9° C. δ(CDCl$_3$) 8.43(s, 1H, Pyrimidine-H), 7.67(d, J=2.4 Hz, 1H, Pyrazole-5-H), 7.51-7.56 (m, 2H, Ph-2,6-2H), 7.07-7.13(m, 2H, Ph-3,5-2H), 6.01(s, 1H, NH), 5.91(d, J=2.4 Hz, 1H, Pyrazole-4-H), 4.78(t, 2H, O—CH$_2$), 3.91-3.96(m, 2H, N—CH$_2$), 2.73-2.80 (m, 2H, CH$_2$), 1.24(t,3H, CH$_3$).

Compound 32-17: m.p. 75.4° C. δ(CDCl$_3$) 8.42(s, 1H, Pyrimidine-H), 7.74(d, J=2.4 Hz, 1H, Pyrazole-5-H), 7.57 (d, 1H, Ph-6-H), 7.48(d, J=1.5 Hz, 1H, Ph-3-H), 7.26-7.36 (m, 2H, Ph-4,5-2H), 6.09(s, 1H, NH), 5.94(d, J=2.4 Hz, 1H, Pyrazole-4-H), 4.47(t, 2H, O—CH$_2$), 3.93(m, 2H, N—CH$_2$), 2.77(m, 2H, CH$_2$), 1.25(t,3H, CH$_3$).

Compound 32-18: m.p. 100.9° C. δ(CDCl$_3$) 8.44(s, 1H, Pyrimidine-H), 7.73(d, J=2.4 Hz, 1H, Pyrazole-5-H), 7.64 (s, 1H, Ph-2-H), 7.45(d, 1H, Ph-6-H), 7.33(t, 1H, Ph-5-H), 7.18(d, 1H, Ph-4-H), 5.99(s, 1H, NH), 5.94(d, J=2.4 Hz, 1H, Pyrazole-4-H), 4.49(t, 2H, O—CH$_2$), 3.95(m, 2H, N—CH$_2$), 2.77(m, 2H, CH$_2$), 1.27(t,3H, CH$_3$).

Compound 32-19: m.p. 138.6° C. δ(CDCl$^3$) 1.24(3H, t), 2.71-2.82(2H, q), 3.90-3.98(2H, q), 4.49(2H, t), 5.93(1H, d), 6.01(1H, t), 7.37(2H, d), 7.53(2H, d), 7.72(1H, d), 8.44(1H, s).

Compound 32-21: m.p. 97.6° C. δ(CDCl$_3$) 8.41(s, 1H, Pyrimidine-H), 7.73(d, J=2.4 Hz, 1H, Pyrazole-5-H), 7.51 (s, 1H, Ph-3-H), 7.49(d, 1H, Ph-6-H), 7.28(d, 1H, Ph-5-H), 6.09(s, 1H, NH), 5.95(d, J=2.4 Hz, 1H, Pyrazole-4-H), 4.46(t, 2H, O—CH$_2$), 3.94(m, 2H, N—CH$_2$), 2.76(m, 2H, CH$_2$), 1.25(t,3H, CH$_3$).

Compound 32-23: oil. δ(CDCl$_3$) 8.41(s, 1H, Pyrimidine-H), 7.27-7.46(m, 4H, Pyrazole-5-H, PhH), 6.12(s, 1H, NH), 5.96(d, 1H, Pyrazole-4-H), 4.45(t, 2H, O—CH$_2$), 3.90-3.95 (m, 2H, N—CH$_2$), 2.73-2.82(m, 2H, CH$_2$), 1.22-1.28(m, 3H, CH$_3$).

Compound 32-25: m.p. 104.9° C. δ(CDCl$_3$) 8.46(s, 1H, Pyrimidine-H), 7.71(d, J=2.7 Hz, 1H, Pyrazole-5-H), 7.49(s, 2H, Ph-2,6-2H), 7.17(s, 1H, Ph-4-H), 5.98(s, 1H, NH), 5.96(d, J=2.7 Hz, 1H, Pyrazole-4-H), 4.49(t, 2H, O—CH$_2$), 3.93-3.96(m, 2H, N—CH$_2$), 2.77-2.80(m, 2H, CH$_2$), 1.25(t, 3H, CH$_3$).

Compound 32-30: oil. δ(CDCl$_3$) 8.42(s, 1H, Pyrimidine-H), 7.46(s, 2H, Ph-3,5-2H), 7.33(d, J=2.4 Hz, 1H, Pyrazole-5-H), 6.05(s, 1H, NH), 5.96(d, J=2.4 Hz, 1H, Pyrazole-4-H), 4.43(t, 2H, O—CH$_2$), 3.89-3.95(m, 2H, N—CH$_2$), 2.74-2.82 (m, 2H, CH$_2$), 1.26(t, 3H, CH$_3$).

Compound 32-49: m.p. 145.1° C. δ(CDCl$_3$) 8.44(s, 1H, Pyrimidine-H), 7.80(d, J=2.4 Hz, 1H, Pyrazole-5-H), 7.69(s, 4H, PhH), 6.00(d, J=2.4 Hz, 1H, Pyrazole-4-H), 5.91(s, 1H, NH), 4.51(t, 2H, O—CH$_2$), 3.93-3.98(m, 2H, N—CH$_2$), 2.72-2.78(m,2H, CH$_2$), 1.21-1.28(m,3H, CH$_3$).

Compound 32-57: m.p. 112.5° C. δ(CDCl$_3$) 8.43(s, 1H, Pyrimidine-H), 7.69(d, J=2.4 Hz, 1H, Pyrazole-5-H), 7.46 (d, J=8.7 Hz, 2H, Ph-2,6-2H), 7.19(d, J=8.7 Hz, 2H, Ph-3,5-2H), 6.04(s, 1H, NH), 5.89(d, J=2.4 Hz, 1H, Pyrazole-4-H), 4.48(t, 2H, O—CH$_2$), 3.91-3.97(m, 2H, N—CH$_2$), 2.72-2.80(m,2H, CH$_2$), 2.36(s, 3H, CH$_3$), 1.24(t,3H, CH$_3$).

Compound 32-69: m.p. 119.9° C. δ(CDCl$_3$) 8.44(s, 1H, Pyrimidine-H), 7.81(d, J=2.4 Hz, 1H, Pyrazole-5-H), 7.64-7.68 (m, 4H, Ph-2,3,5,6-4H), 5.98(d, J=2.4 Hz, 1H, Pyrazole-4-H), 5.95(s, 1H, NH), 4.51(t, 2H, O—CH$_2$), 3.96(m, 2H, N—CH$_2$), 2.77(m, 2H, CH$_2$), 1.24(t,3H, CH$_3$).

Compound 32-78: m.p. 102.1° C. δ(CDCl$_3$) 8.45(s, 1H, Pyrimidine-H), 7.66(d, J=2.4 Hz, 1H, Pyrazole-5-H), 7.52-7.62(m, 2H, Ph-2,6-2H),7.28-7.33(m, 2H, Ph-3,5-2H), 5.98 (s, 1H, NH), 5.94(d, J=2.4 Hz, 1H, Pyrazole-4-H), 4.49(t, 2H, O—CH$_2$), 3.94-3.96(m, 2H, N—CH$_2$), 2.75-2.78(m, 2H, CH$_2$), 1.24(t, 3H, CH$_3$).

Compound 33-1: m.p. 73.6° C. δ(CDCl$_3$) 8.23(s, 1H, Pyrimidine-H), 7.75(d, J=2.4 Hz, 1H, Pyrazole-5-H), 7.59 (d, J=8.4 Hz, 2H, Ph-2,6-2H), 7.42(m, 2H, Ph-3,5-2H), 7.23(m, 1H, Ph-4-H), 6.70(t,1H, CHF$_2$), 6.22(s, 1H, NH), 5.90(d, J=2.4 Hz, 1H, Pyrazole-4-H), 4.36(t, 2H, O—CH$_2$), 3.75(m, 2H, N—CH$_2$).

Compound 33-4: m.p. 115.2° C. δ(CDCl$_3$) 8.56(s, 1H, Pyrimidine-H), 7.67(d, J=2.4 Hz, 1H, Pyrazole-5-H), 7.51-7.56(m, 2H, Ph-2,6-2H), 7.07-7.14(m, Ph-3,5-2H), 6.69(t, J=5 3.4 Hz, 1H, CF$_2$H), 6.43(s, 1H, NH), 5.91(d, J=2.4 Hz, 1H, Pyrazole-4-H), 4.52(t, 2H, O—CH$_2$), 3.95-4.01(m, 2H, N—CH$_2$).

Compound 33-18: m.p. 99.3° C. δ(CDCl$_3$) 8.56(s, 1H, Pyrimidine-H), 7.74(d, J=2.4 Hz, 1H, Pyrazole-5-H), 7.64 (s, 1H, Ph-2-H), 7.44(d, 1H, Ph-6-H), 7.33(t, 1H, Ph-5-H), 7.18(d, 1H, Ph-4-H). 6.70(t, 1H, CHF$_2$), 6.37(s, 1H, NH), 5.94(d, J=2.7 Hz, 1H, Pyrazole-4-H), 4.53(t, 2H, O—CH$_2$), 3.99(m, 2H, N—CH$_2$).

Compound 33-19: m.p. 142.8° C. δ(CDCl$_3$) 4.00-4.05(2H, q), 4.56(2H, t), 5.96(1H, s), 6.50(1H, s), 6.75(1H, t), 7.40 (2H, d), 7.51(2H, d), 7.75(1H, s), 8.60(1H, s).

Compound 33-21: m.p. 136.5° C. δ(CDCl$_3$) 8.55(s, 1H, Pyrimidine-H), 7.72(d, J=2.4 Hz, 1H, Pyrazole-5-H), 7.51 (s, 1H, Ph-3-H), 7.49(d, 1H, Ph-6-H), 7.35(d, 1H, Ph-5-H), 6.70(t,1H, CHF$_2$), 6.39(s, 1H, NH), 5.94(d, J=2.4 Hz, 1H, Pyrazole-4-H), 4.49(t, 2H, O—CH$_2$), 3.97(m, 2H, N—CH$_2$).

Compound 33-25: m.p. 126.5° C. δ(CDCl$_3$) 8.58(s, 1H, Pyrimidine-H), 7.72(d, J=2.4 Hz, 1H, Pyrazole-5-H), 7.49-7.51(m,2H, Ph-2,6-2H), 7.19(d,1H, Ph-4-H), 6.72(t, J=53.40 Hz, 1H, CF$_2$H), 6.30(s, 1H, NH), 5.96(d, J=2.4 Hz, 1H, Pyrazole-4-H), 4.53(t, 2H, O—CH$_2$), 3.97-4.03(m, 2H, N—CH$_2$).

Compound 33-30: m.p. 132.9° C. δ(CDCl$_3$) 8.54(s, 1H, Pyrimidine-H), 7.47(s,2H, Ph-3,5-2H), 7.34(d, J=2.4 Hz, 1H, Pyrazole-5-H), 6.73(t, J=53.7 Hz, 1H, CF$_2$H), 6.52(s, 1H, NH)5.96(d, J=2.4 Hz, 1H, Pyrazole-4-H), 4.46(t, 2H$_2$O—CH$_2$), 3.94-3.99(m, 2H, N—CH$_2$).

Compound 33-49: m.p. 151.7° C. δ(CDCl$_3$) 8.57(s, 1H, Pyrimidine-H), 7.82(d, J=2.4 Hz, 1H, Pyrazole-5-H), 7.70 (s,4H, PhH), 6.70(t, J=53.70 Hz, 1H, CF$_2$H), 6.52(s, 1H, NH), 6.01(d, J=2.4 Hz, 1H, Pyrazole-4-H), 4.54(t, 2H, O—CH$_2$), 3.98-4.03(m, 2H, N—CH$_2$).

Compound 33-57: m.p. 106.6° C. δ(CDCl$_3$) 8.56(s, 1H, Pyrimidine-H), 7.71(d, J=2.4 Hz, 1H, Pyrazole-5-H), 7.46 (d, J=8.4 Hz, 2H, Ph-2,6-2H), 7.21(d, J=8.4 Hz, 2H, Ph-3,5-2H), 6.69(t, J=54.00 Hz, 1H, CF$_2$H), 6.52(s, 1H, NH), 5.89(d, J=2.4 Hz, 1H, Pyrazole-4-H), 4.53(t, 2H, O—CH$_2$), 3.95-4.00(m, 2H, N—CH$_2$), 2.37(s, 3H, CH$_3$).

Compound 33-69: m.p. 122.3° C. δ(CDCl$_3$) 8.57(s, 1H, Pyrimidine-H), 7.81(d, J=2.7 Hz, 1H, Pyrazole-5-H), 7.01-7.64 (m, 4H, Ph-2,3,5,6-4H), 6.70(t,1H, CHF$_2$), 6.31(s, 1H, NH), 5.98(d, J=2.7 Hz, 1H, Pyrazole-4-H), 4.54(t, 2H, O—CH$_2$), 4.00(m, 2H, N—CH$_2$).

Compound 35-19: δ(CDCl$_3$) 1.42(3H, d), 4.38(2H, d), 4.65(1H, s), 5.93(1H, d), 6.06-6.08(1H, m), 7.38(2H, d), 7.51(2H, d), 7.71(1H, d), 8.28(1H,s).

Compound 36-19: m.p. 80-82° C. δ(CDCl$_3$) 1.42(3H, d), 2.42(3H, s), 4.37(2H, d), 4.65-4.67(1H, m), 5.91(1H, s), 5.93(1H, d), 7.36(2H, d), 7.53(2H, d), 7.70(1H, d), 8.40(1H, s).

Compound 37-19: δ(CDCl$_3$) 1.24(3H, t), 1.42(3H, d), 2.73-2.77(2H, q), 4.37(2H, d), 4.39(1H, s), 5.78-5.82(1H, m), 5.93(1H, d), 7.38(2H, d), 7.52(2H, d), 7.70(1H, d), 8.43(1H,s).

Compound 40-1: oil. δ(CDCl$_3$) 8.66(s, 1H, Quinazoline-3-H), 7.76(d, J=2.4 Hz, 1H, Pyrazole-5-H), 7.72-7.75 (m, 5H, Ph-2,3,4,5,6-5H), 7.72-7.75 (m, 4H, Quinazoline-5,6,7,8-4H), 6.22(s, 1H, NH), 5.90(d, J=2.4 Hz, 1H, Pyrazole-4-H), 4.36(t, 2H, O—CH$_2$), 3.75(m, 2H, N—CH$_2$).

Compound 40-4: m.p. 155.7° C. δ(CDCl$_3$) 8.67(s, 1H, Quinazoline-3-H), 7.82(d, 1H, Quinazoline-6-H), 7.67(d, J=2.7 Hz, 1H, Pyrazole-5-H), 7.53-7.65(m, 4H, Ph-2,6-2H, Quinazoline-7,8-2H), 7.10-7.19(m, 3H, Ph-3,5-2H, Quinazoline-9-H), 6.95(s, 1H, NH), 5.94(d, J=2.7 Hz, 1H, =CH), 4.62(t, 2H, CH$_2$), 4.05-4.10(m, 2H, CH$_2$).

Compound 40-18: m.p. 146.1° C. δ(CDCl$_3$) 8.68(s, 1H, Quinazoline-3-H), 7.74(d, J=2.7 Hz, 1H, Pyrazole-5-H), 7.63-7.71 (m, 4H, Ph-2, 4,5,6-4H), 7.31-7.54 (m, 4H, Quinazoline-5,6,7,8-4H), 6.78(s, 1H, NH), 5.96(d, J=2.7 Hz, 1H, Pyrazole-4-H), 4.63(t, 2H, O—CH$_2$), 4.10(m, 2H, N—CH$_2$).

Compound 40-19: m.p. 176.4° C. δ(CDCl₃) 4.10-4.15 (2H, q), 4.67(2H, t), 5.99(1H, s), 7.11(1H, s), 7.44(2H, d), 7.58(2H, d), 7.66(1H, d), 7.71-7.76(2H, d), 7.90(1H, d), 8.70(1H, s).

Compound 40-21: m.p. 141.7° C. δ(CDCl₃) 8.66(s, 1H, Quinazoline-3-H), 7.72(d, J=2.7 Hz, 1H, Pyrazole-5-H), 7.80-7.83 (m, 3H, Ph-3,5,6-3H), 7.51-7.58 (m, 4H, Quinazoline-5,6,7,8-4H), 6.90(s, 1H, NH), 5.97(d, J=2.4 Hz, 1H, Pyrazole-4-H), 4.59(t, 2H, O—CH₂), 4.08(m, 2H, N—CH₂).

Compound 40-25: m.p. 199.9° C. δ(CDCl₃) 8.69(s, 1H, Quinazoline-3-H), 7.83(d, 1H, Quinazoline-6-H), 7.73(d, J=3.0 Hz, 1H, Pyrazole-5-H), 7.65-7.66(m, 2H, Quinazoline-7,8-H), 7.51-7.52(m, 2H, Ph-2,6-2H), 7.30-7.36(m, 1H, Quinazoline-7,8-H), 7.21-7.22(m, 1H, Ph-4-H), 6.56(s, 1H, NH), 5.99(d, J=3.0 Hz, 1H, Pyrazole-4-H), 4.62(t, 2H₂O—CH₂), 4.09-4.14(m, 2H, N—CH₂).

Compound 40-30: m.p. 170.5° C. δ(CDCl₃) 8.66(s, 1H, Quinazoline-3-H), 7.52-7.84(m, 3H, Quinazoline-6,7,9-3H), 7.46(s, 2H, Ph-3,5-2H), 7.35(d, J=2.4 Hz, 1H, Pyrazole-5-H), 7.24(t, 1H, Quinazoline-8-1H), 5.99(d, J=2.4 Hz, 1H, Pyrazole-4-H), 4.57(t, 2H, O—CH₂), 4.04-4.09(m, 2H, N—CH₂).

Compound 40-49: oil. δ(CDCl₃) 8.68(s, 1H, Quinazoline-3-H), 7.83(d, 1H, Quinazoline-6-H), 7.81(d, J=3.0 Hz, 1H, Pyrazole-5-H), 7.64-7.76(m, 5H, Quinazoline-7,8,9-H, Ph-2,6-2H), 7.31(d, 2H, Ph-3,5-2H), 6.47(s, 1H, NH), 6.02 (d, J=3.0 Hz, 1H, Pyrazole-4-H), 4.62(t, 2H, O—CH₂), 4.09-4.15(m, 2H, N—CH₂).

Compound 40-57: m.p. 178.7° C. δ(CDCl₃) 8.66(s, 1H, Quinazoline-3-H), 7.78(d, 1H, Quinazoline-6-H), 7.70(d, J=2.4 Hz, 1H, Pyrazole-5-H), 7.58-7.67(m, 3H, Quinazoline-7,8,9-H), 7.50(d, J=8.4 Hz, 2H, Ph-2,6-2H), 7.10(d, J=8.4 Hz, 2H, Ph-3,5-2H), 5.92(d, J=2.4 Hz, 1H, Pyrazole-4-H), 4.64(t, 2H, O—CH₂), 4.05-4.10(m, 2H, N—CH₂), 2.40(s, 3H, CH₃).

Compound 40-69: m.p. 170.1° C. δ(CDCl₃) 8.68(s, 1H, Quinazoline-3-H), 7.81(d, J=2.4 Hz, 1H, Pyrazole-5-H), 7.62-7.71 (m, 4H, Ph-2,3,5,6-4H), 7.62-7.71 (m, 4H, Quinazoline-5,6,7,8-4H), 6.62(s, 1H, NH), 6.00(d, J=2.7 Hz, 1H, Pyrazole-4-H), 4.64(t, 2H, O—CH₂), 4.11(m, 2H, N—CH₂).

Compound 42-1: m.p. 129.7° C. δ(CDCl₃) 8.48(s, 1H, Pyrimidine-H), 7.74(d, J=2.7 Hz, 1H, Pyrazole-5-H), 7.57 (d, J=8.4 Hz, 2H, Ph-2,6-2H), 7.40(d, 2H, Ph-3,5-2H), 7.19(m, 1H, Ph-4-H), 7.03(s,1H, Thieno-H), 6.98(s, 1H, NH), 5.92(d, J=2.4 Hz, 1H, Pyrazole-4-H), 4.55(t, 2H, O—CH₂), 4.08(m, 2H, N—CH₂).

Compound 42-4: m.p. 132.2° C. δ(CDCl₃) 8.48(s, 1H, Pyrimidine-H), 7.67(d, J=2.4 Hz, 1H, Pyrazole-5-H), 7.49-7.55(m, 2H, Ph-2,6-2H), 7.04-7.13(m, 2H, Ph-3,5-2H), 6.97 (s, 1H, Thiophene-H), 6.92(s, 1H, NH), 5.92(d, J=2.4 Hz, 1H, Pyrazole-4-H), 4.53(t, 2H, O—CH₂), 4.04-4.10(m, 2H, N—CH₂).

Compound 42-17: m.p. 122.4° C. δ(CDCl₃) 8.47(s, 1H, Pyrimidine-H), 7.74(d, J=2.4 Hz, 1H, Pyrazole-5-H), 7.54 (d, J=7.5 Hz, 1H, Ph-6-H), 7.48(d, J=7.5 Hz, 1H, Ph-3-H), 7.31-7.36(m, 2H, Ph-4,5-2H), 7.05(s,1H, Thieno-H), 7.01(s, 1H, NH), 5.94(d, J=2.1 Hz, 1H, Pyrazole-4-H), 4.53(t, 2H, O—CH₂), 4.07(m, 2H, N—CH₂).

Compound 42-18: m.p. 100.1° C. δ(CDCl₃) 8.48(s, 1H, Pyrimidine-H), 7.72(d, J=2.7 Hz, 1H, Pyrazole-5-H), 7.61 (s, 1H, Ph-2-H), 7.43(d, 1H, Ph-6-H), 7.31(t, 1H, Ph-5-H), 7.17(d, 1H, Ph-4-H), 7.04(s,1H, Thieno-H), 6.95(s, 1H, NH), 5.94(d, J=2.7 Hz, 1H, Pyrazole-4-H), 4.55(t, 2H, O—CH₂), 4.08(m, 2H, N—CH₂).

Compound 42-21: m.p. 123.1° C. δ(CDCl₃) 8.47(s, 1H, Pyrimidine-H), 7.73(d, J=2.4 Hz, 1H, Pyrazole-5-H), 7.48-7.51 (m, 2H, Ph-3,6-2H), 7.32(d, 1H, Ph-5-H), 7.05(s,1H, Thieno-H), 6.97(s, 1H, NH), 5.94(d, J=2.4 Hz, 1H, Pyrazole-4-H), 4.51(t, 2H, O—CH₂), 4.06(m, 2H, N—CH₂).

Compound 42-25: oil. δ(CDCl₃) 8.49(s, 1H, Pyrimidine-H), 7.71(d, J=2.4 Hz, 1H, Pyrazole-5-H), 7.43-7.49(m, 2H, Ph-2,6-2H), 7.14-7.19(m, 1H, Ph-4-H), 7.06(s, 1H, Thiophene-H), 6.94(s, 1H, NH), 5.96(d, J=2.4 Hz, 1H, Pyrazole-4-H), 4.55(t, 2H, O—CH₂), 4.05-4.11(m, 2H, N—CH₂).

Compound 42-30: oil. δ(CDCl₃) 8.46(s, 1H, Pyrimidine-H), 7.45(s, 2H, Ph-3,5-2H), 7.32(d, J=2.4 Hz, 1H, Pyrazole-5-H), 7.06(s, 1H, Thiophene-H), 6.98(s, 1H, NH), 5.96(d, J=2.4 Hz, 1H, Pyrazole-4-H), 4.47(t, 2H, O—CH₂), 4.04-4.07(m, 2H, N—CH₂).

Compound 42-49: m.p. 164.9° C. δ(CDCl₃) 8.49(s, 1H, Pyrimidine-H), 7.80(d, J=2.4 Hz, 1H, Pyrazole-5-H), 7.63-7.67(m, 4H, PhH), 7.04(s, 1H, Thiophene-H), 6.90(s, 1H, NH), 6.01(d, J=2.4 Hz, 1H, Pyrazole-4-H), 4.57(t, 2H, O—CH₂), 4.07-4.10(m, 2H, N—CH₂).

Compound 42-57: m.p. 113.4° C. δ(CDCl₃) 8.48(s, 1H, Pyrimidine-H), 7.68(d, J=2.7 Hz, 1H, Pyrazole-5-H), 7.44 (d, J=8.4 Hz, 2H, Ph-2,6-2H), 7.19(d, J=8.4 Hz, 2H, Ph-3,5-2H), 7.03(s, 1H, Thiophene-H), 6.03(s, 1H, NH), 5.89(d, J=2.7 Hz, 1H, Pyrazole-4-H), 4.54(t, 2H, O—CH₂), 4.04-4.10(m, 2H, N—CH₂), 2.36(s, 3H, CH₃).

Compound 42-69: m.p. 149.7° C. δ(CDCl₃) 8.48(s, 1H, Pyrimidine-H), 7.79(d, J=2.4 Hz, 1H, Pyrazole-5-H), 7.65 (m, 4H, Ph-2,3,5,6-4H), 7.03(s,1H, Thieno-H), 6.92(s, 1H, NH), 5.98(d, J=2.4 Hz, 1H, Pyrazole-4-H), 4.57(t, 2H, O—CH₂), 4.09(m, 2H, N—CH₂).

Compound 42-78: oil. δ(CDCl₃) 8.49(s, 1H, Pyrimidine-H), 7.96(d, J=2.4 Hz, 1H, Pyrazole-5-H), 7.71-7.74(m, 2H, Ph-2,6-2H), 7.29-7.33(m, 2H, Ph-3,5-2H), 7.16(s, 1H, Thiophene-H), 6.96(s, 1H, NH), 5.94(d, J=2.4 Hz, 1H, Pyrazole-4-H), 4.55(t, 2H, O—CH₂), 4.07-4.09(m, 2H, N—CH₂).

Compound 57-4: δ(CDCl₃) 2.47(3H, s), 3.92(2H, d), 4.14 (2H, t), 5.78(1H, s), 7.13(2H, t), 7.55(1H, s), 7.56-7.59(3H, m), 8.39(1H, s).

Compound 57-19: m.p. 130.0° C. δ(CDCl₃): 8.41(s,1H, Pyrimidine-H), 7.58(s,1H, Pyrazole-5-H), 7.56(d, J=9.0 Hz, 2H, Ph-2,6-2H), 7.50(s,1H, Pyrazole-3-H), 7.40(d, J=9.0 Hz, 2H, Ph-3,5-2H), 5.85(s, 1H, NH), 4.14(t, 2H, O—CH₂), 3.95-3.90(m, 2H, N—CH₂), 2.46(t, 3H, CH₃).

Compound 58-19: m.p. 134.7° C. δ(CDCl₃): 8.45(s,1H, Pyrimidine-H), 7.60(s,1H, Pyrazole-5-H), 7.56(d, J=9.0 Hz, 2H, Ph-2,6-2H), 7.50(s,1H, Pyrazole-3-H), 7.40(d, J=9. 0 Hz, 2H, Ph-3,5-2H), 5.82(s, 1H, NH), 4.15(t, 2H, O—CH₂), 3.95-3.90(m, 2H, N—CH₂), 2.84-2.77(m, 2H, CH₂), 1.27(t, 3H, CH₃).

Compound 59-19: m.p. 125.7° C. δ(CDCl₃): 8.58(s,1H, Pyrimidine-H), 7.58(s,1H, Pyrazole-5-H), 7.56(d, J=9.0 Hz, 2H, Ph-2,6-2H), 7.50(s,1H, Pyrazole-3-H), 7.40(d, J=9.0 Hz, 2H, Ph-3,5-2H), 6.74(t, J=54 Hz, 1H, CF₂H), 6.08(s, 1H, NH), 4.16(t, 2H, O—CH₂), 4.01-3.96(m, 2H, N—CH₂).

Compound 68-19: m.p. 119.2° C. δ(CDCl₃): 8.49(s, 1H, Pyrimidine-H), 7.60(s, 1H, Pyrazole-5-H), 7.55(d, J=8.7 Hz, 2H, Ph-2,6-2H), 7.51(s, 1H, Pyrazole-3-H), 7.39(d, J=8.7 Hz, 2H, Ph-3,5-2H), 7.01(s, 1H, Thiophene-H), 6.97(s, 1H, NH), 4.22(t, 2H, O—CH₂), 4.07-4.02(m, 2H, N—CH₂).

Compound 59-21: oil. δ(CDCl₃) 8.54(s, 1H, Pyrimidine-H), 8.01(s,1H, Ph-3-H), 7.57(s, 1H, Pyrazole-5-H), 7.49-7.52(m, 2H, Ph-6-H, Pyrazole-3-H), 7.35(dd, 1H, Ph-5-H), 6.73(t, J=53.7 Hz, 1H, CF₂H), 6.25(s, 1H, NH), 4.11(t, 2H, O—CH₂), 3.75-3.81(m, 2H, N—CH₂), 2.13-2.18(m, 2H, CH₂).

Compound 68-4: δ(CDCl₃) 4.03-4.04(2H, q), 4.20(2H, t), 7.10(1H, s), 7.12-7.15(2H, m), 7.25(1H, d), 7.52-7.58(4H, m), 8.48(1H,s).

Compound 116-5:δ(CDCl$_3$) 8.43(s, 1H, Pyrimidine-H), 7.68(d, J=2.7 Hz, 1H, Pyrazole-5-H), 7.49-7.54(m, 2H, Ph-2,6-2H), 7.34-7.39(m, 2H, Ph-3,5-2H), 5.86(d, J=2.7 Hz, 1H, Pyrazole-4-H), 4.56(t, 2H, O—CH$_2$), 4.03(t, 2H, N—CH$_2$), 3.22(s, 3H, NCH$_3$), 2.79-2.87(m, 2H, CH$_2$), 1.26 (t, 3H, CH$_3$).

Compound 118-69: m.p. 83.5° C. δ(CDCl$_3$) 8.28(s, 1H, Pyrimidine-H), 7.81(d, J=2.7 Hz, 1H, Pyrazole-5-H), 7.65-7.72 (m, 4H, Ph-2,3,5,6-4H), 6.15(s, 1H, NH), 5.97(d, J=2.7 Hz, 1H, Pyrazole-4-H), 4.44(t, 2H, O—CH$_2$), 3.75(m, 2H, N—CH$_2$), 2.16(m,2H, CH$_2$).

Compound 119-69: oil. δ(CDCl$_3$) 8.07(s, 1H, Pyrimidine-H), 7.81(d, J=2.4 Hz, 1H, Pyrazole-5-H), 7.65-7.72 (m, 4H, Ph-2,3,5,6-4H), 5.98(d, J=3 Hz, 1H, Pyrazole-4-H), 5.43(s, 1H, NH), 4.43(t, 2H, O—CH$_2$), 3.72(m, 2H, N—CH$_2$), 3.44(s, 2H, NH$_2$), 2.17(m,2H, CH$_2$).

Compound 120-69: oil. δ(CDCl$_3$) 8.10(s, 1H, Pyrimidine-H), 7.80(d, J=3 Hz, 1H, Pyrazole-5-H), 7.64-7.72 (m, 4H, Ph-2,3,5,6-4H), 6.03(d, J=3 Hz, 1H, Pyrazole-4-H), 5.99(s, 1H, NH), 4.43(t, 2H, O—CH$_2$), 3.84(m, 2H, N—CH$_2$), 2.17(m,2H, CH$_2$).

Compound 121-69: m.p. 96.0° C. δ(CDCl$_3$) 10.38(s, 1H, CHO), 9.47(s, 1H, NH), 8.42(s, 1H, Pyrimidine-H), 7.81(d, 1H, Pyrazole-5-H), 7.65-7.73 (m, 4H, Ph-2,3,5,6-4H), 6.03 (d, 1H, Pyrazole-4-H), 4.41(t, 2H, O—CH$_2$), 3.84(m, 2H, N—CH$_2$), 2.18(m,2H, CH$_2$).

Compound 122-69: m.p. 94.1° C. δ(CDCl$_3$) 8.28(s, 1H, Pyrimidine-H), 7.82(d, J=2.4 Hz, 1H, Pyrazole-5-H), 7.65-7.72 (m, 4H, Ph-2,3,5,6-4H), 5.95(d, J=2.7 Hz, 1H, Pyrazole-4-H), 5.35(s, 1H, NH), 4.44(t, 2H, O—CH$_2$), 3.74(m, 2H, N—CH$_2$), 2.18(m, 2H, CH$_2$), 2.14(s,3H, CH$_3$).

Compound 123-69: oil. δ(CDCl$_3$) 8.15(s, 1H, Pyrimidine-H), 7.81(d, J=2.7 Hz, 1H, Pyrazole-5-H), 7.68-7.73 (m, 4H, Ph-2,3,5,6-4H), 5.96(d, J=2.7 Hz, 1H, Pyrazole-4-H), 5.89 (s, 1H, NH), 4.41(t, 2H, O—CH$_2$), 3.85(s,3H, CH$_3$), 3.71(m, 2H, N—CH$_2$), 2.16(m,2H, CH$_2$).

Compound 124-19:m.p. 140.1° C. δ(CDCl$_3$) 8.36(s, 1H, Pyrimidine-H), 7.70(d, J=2.7 Hz, 1H, Pyrazole-5-H), 7.53 (d, J=9.0 Hz, 2H, Ph-2,6-2H), 7.37(d, J=9.3 Hz, 2H, Ph-3,5-2H), 5.91(d, J=2.7 Hz, 1H, Pyrazole-4-H), 5.87(s, 1H, NH), 4.41(t, 2H, O—CH$_2$), 3.70-3.75(m, 2H, N—CH$_2$), 2.45(s, 3H), 2.12-2.17(m, 2H, CH$_2$).

Compound 125-19:δ(CDCl$_3$) 8.42(s, 1H, Pyrimidine-H), 7.70(d, J=2.7 Hz, 1H, Pyrazole-5-H), 7.51-7.55(m, 2H, Ph-2,6-2H), 7.35-7.39(m, 2H, Ph-3,5-2H), 5.91(d, J=2.7 Hz, 1H, Pyrazole-4-H), 5.88(s, 1H, NH), 4.41(t, 2H, O—CH$_2$), 3.69-3.75(m, 2H, N—CH$_2$), 2.75-2.80(m, 2H, CH$_3$—CH$_2$), 2.12-2.18(m, 2H, CH$_2$), 1.26(t, 3H, CH$_3$).

Compound 125-69: m.p. 94.3° C. δ(CDCl$_3$) 8.42(s, 1H, Pyrimidine-H), 7.81(d, J=2.4 Hz, 1H, Pyrazole-5-H), 7.65-7.73 (m, 4H, Ph-2,3,5,6-4H), 5.97(d, J=2.7 Hz, 1H, Pyrazole-4-H), 5.89(s, 1H, NH), 4.43(t, 2H, O—CH$_2$), 3.73(m, 2H, N—CH$_2$), 2.78(m, 2H, CH$_2$CH$_3$), 2.17(m, 2H, CH$_2$), 1.26(t,3H, CH$_3$).

Compound 126-19:m.p. 132.9° C. δ(CDCl$_3$) 8.54(s, 1H, Pyrimidine-H), 7.70(d, J=2.7 Hz, 1H, Pyrazole-5-H), 7.51-7.55(m, 2H, Ph-2,6-2H), 7.35-7.40(m, 2H, Ph-3,5-2H), 6.71 (t, 1H, CHF$_2$), 6.23(s, 1H, NH), 5.91(d, J=2.7 Hz, 1H, Pyrazole-4-H), 4.43(t, 2H, O—CH$_2$), 3.73-3.79(m, 2H, N—CH$_2$), 2.13-2.19(m, 2H, CH$_2$).

Compound 126-69: oil. δ(CDCl$_3$) 8.54(s, 1H, Pyrimidine-H), 7.82(d, J=2.7 Hz, 1H, Pyrazole-5-H), 7.65-7.73 (m, 4H, Ph-2,3,5,6-4H), 6.74(t,1H, CHF$_2$), 6.29(s, 1H, NH), 5.97(d, J=2.7 Hz, 1H, Pyrazole-4-H), 4.45(t, 2H, O—CH$_2$), 3.79(m, 2H, N—CH$_2$), 2.18(m, 2H, CH$_2$).

Compound 127-19: m.p. 165.7° C. δ(CDCl$_3$) 8.66(s, 1H, Quinazoline-3-H), 7.82(d, J=2.7 Hz, 1H, Pyrazole-5-H), 7.70-7.78(m, 4H, Quinazoline-5,6,7,8-4H), 7.52 (dd, 2H, Ph-2H),7.37 (dd, 2H, Ph-2H),6.07(s, 1H, NH), 5.92(d, J=2.7 Hz, 1H, Pyrazole-4-H), 4.31(t, 2H, O—CH$_2$), 3.43-3.53 (m, 2H, N—CH$_2$), 2.02-2.08 (m, 2H, CH$_2$).

Compound 127-69: m.p. 149.7° C. δ(CDCl$_3$) 8.67(s, 1H, Quinazoline-3-H), 7.82(d, J=2.4 Hz, 1H, Pyrazole-5-H), 7.65-7.81 (m, 4H, Ph-2,3,5,6-4H), 7.65-7.81 (m, 4H, Quinazoline-5,6,7,8-4H), 6.50(s, 1H, NH), 5.98(d, J=2.7 Hz, 1H, Pyrazole-4-H), 4.50(t, 2H, O—CH$_2$), 3.89(m, 2H, N—CH$_2$), 2.26(m, 2H, CH$_2$).

Compound 128-19:δ(CDCl$_3$) 8.46(s, 1H, Pyrimidine-H), 7.70(d, J=2.7 Hz, 1H, Pyrazole-5-H), 7.50-7.54(m, 2H, Ph-2,6-2H), 7.34-7.40(m, 2H, Ph-3,5-2H), 7.05(s, 1H, Thiazole-H), 6.92(s, 1H, NH), 5.91(d, J=2.7 Hz, 1H, Pyrazole-4-H), 4.43(t, 2H, O—CH$_2$), 3.82-3.90(m, 2H, N—CH$_2$), 2.17-2.27(m, 2H, CH$_2$).

Compound 128-69: m.p. 123.5° C. δ(CDCl$_3$) 8.46(s, 1H, Pyrimidine-H), 7.81(d, J=2.4 Hz, 1H, Pyrazole-5-H), 7.64-7.71 (m, 4H, Ph-2,3,5,6-4H), 7.06(s,1H, Thieno-H), 6.92(s, 1H, NH), 5.96(d, J=2.7 Hz, 1H, Pyrazole-4-H), 4.46(t, 2H, O—CH$_2$), 3.86(m, 2H, N—CH$_2$), 2.23(m, 2H, CH$_2$).

Test of Biological Activity

The compounds of the present invention showed good activity against many pathogens, insects and pest mites in agricultural field.

Example 8

Fungicidal Testing

The compound samples of the present invention were tested in fungicidal activity in vitro or protective activity in vivo. The results of the fungicidal testing are as follows.

(1) Determination of Fungicidal Activity In Vitro

The method is as follows: High Through Put is used in the test. The compound is dissolved in a proper solvent to become a testing solution whose concentration is designed. The solvent is selected from acetone, methanol, DMF and so on according to their dissolving capability to the sample. In a no animal cule condition, the testing solution and pathogens suspension are added into the cells of 96 cells culture board, which then should be placed in the constant temperature box. 24 hours later, pathogengermination or growth can be investigated by eyeballing, and the activity in vitro of the compound is evaluated based on germination or growth of control treatment.

The activities in vitro (inhibition rate) of some compounds are as follows:

The inhibition rate against rice blast:

At the dosage of 25 ppm, the inhibition rate of compounds 30-1-4, 31-4, 31-78, 32-1, 32-4, 32-21, 32-57, 32-78, 33-4, 33-18, 35-19, 36-19, 37-19, 40-4, 40-18, 40-57, 40-69, 42-1,42-4, 42-18, 42-21, 42-57, 42-69, 42-78, 44-19, 57-4, 59-21, 68-4 and so on was more than 80% against rice blast. The contrast inhibition rate of compounds CK1, CK2, CK3, CK4 and CK5 was 0; At the dosage of 8.3 ppm, the inhibition rate of compounds 31-4, 36-19, 40-4, 40-18, 40-57, 42-1, 42-18, 42-21, 42-57, 42-69, 44-19, 57-4, 59-21, 68-4, 128-69 and so on was more than 80% against rice blast; At the dosage of 2.8 ppm, the inhibition rate of compounds 36-19, 42-1, 42-18, 42-21, 42-69, 44-19, 57-4, 59-21, 68-4 and so on was more than 80% against rice blast.

The inhibition rate against cucumber gray mold:

At the dosage of 25 ppm, the inhibition rate of compounds 36-19, 40-19, 44-19, 57-4, 59-21, 68-4 and so on was more than 80% against cucumber gray mold. The contrast inhibition rate of compounds CK1, CK2, CK3, CK4 and CK5 was 0.

(2) The Determination of Protective Activity In Vivo

The method is as follows: The whole plant is used in this test. The compound is dissolved in a proper solvent to get mother solution. The proper solvent is selected from acetone, methanol, DMF and so on according to their dissolving capability to the sample. The volume rate of solvent and testing solution (v/v) is equal to or less than 5%. The mother solution is diluted with water containing 0.1% tween-80 to get the testing solution whose concentration is designed. The testing solution is sprayed to the host plant by a special plant sprayer. The plant is inoculated with fungus after 24 hours. According to the infecting characteristic of fungus, the plant is stored in a humidity chamber and then transferred into greenhouse after infection is finished. And the other plants are placed in greenhouse directly. The activity of compound is obtained by eyeballing after 7 days in common.

The protective activities in vivo of some compounds are as follows:

The protective activity against cucumber downy mildew in vivo:

At the dosage of 400 ppm, the compounds 30-1-4, 30-1-49, 30-1-57, 31-4, 31-19, 31-18, 31-21, 31-49, 31-57, 31-69, 32-4, 32-18, 32-19, 32-21, 32-49, 33-18, 33-19, 33-21, 35-19, 36-19, 40-4, 40-18, 40-19, 40-21, 40-57, 42-1, 42-18, 42-21, 42-49, 42-57, 42-69, 42-78, 44-19, 57-4, 57-19, 58-19, 59-19, 66-19, 68-19, 68-4 and so on showed more than 80% control against cucumber downy mildew; At the dosage of 100 ppm, the compounds 30-1-19, 30-1-21, 30-1-30, 30-2-19, 31-4, 31-18, 31-19, 31-21, 31-23, 31-30, 31-69, 32-4, 32-17, 32-18, 32-19, 32-21, 32-30, 33-18, 33-19, 33-21, 33-30, 33-49, 33-57, 35-19, 36-19, 40-1, 40-4, 40-17, 40-18, 40-19, 40-21, 40-30, 42-1, 42-17, 42-18, 42-21, 42-69, 44-19, 123-69, 125-69, 126-69, 127-69, 128-69 and so on showed more than 80% control against cucumber downy mildew; At the dosage of 25 ppm, the compounds 30-1-19, 30-1-21, 30-1-30, 30-2-19, 31-18, 31-19, 31-21, 31-23, 31-30, 31-69, 32-4, 32-19, 32-30, 33-18, 33-19, 33-21, 33-30, 33-49, 33-57, 35-19, 36-19, 40-4, 40-17, 40-18, 40-19, 40-21, 40-30, 42-1, 42-17, 42-18, 42-21, 42-69, 44-19 and so on showed more than 80% control against cucumber downy mildew; At the dosage of 12.5 ppm, the compounds 30-2-19, 31-23, 32-19, 32-30, 33-21, 33-30, 33-49, 33-57, 35-19, 36-19, 40-4, 40-18, 40-19, 42-21 and so on showed more than 80% control against cucumber downy mildew; At the dosage of 6.25 ppm, the compounds 30-2-19, 31-23, 32-19, 32-30, 33-21, 33-30, 33-49, 33-57, 36-19, 40-4, 40-18, 40-19, 42-21 and so on showed more than 80% control against cucumber downy mildew.

The protective activity against wheat powdery mildew in vivo:

At the dosage of 400 ppm, the compounds 30-1-57, 30-1-21, 30-2-19, 31-18, 31-21, 31-30, 31-49, 31-57, 31-69, 31-78, 32-1, 32-17, 32-18, 32-19, 32-21, 32-30, 32-49, 32-69, 32-78, 33-4, 33-19, 33-21, 33-30, 33-49, 33-57, 33-69, 35-19, 36-19, 37-19, 40-19, 40-21, 40-69, 42-4, 42-17, 42-18, 42-21, 42-49, 42-57, 42-69, 42-78, 44-19, 57-19, 58-19, 59-19, 66-19, 68-19, 59-21, 118-69, 119-69, 122-69, 123-69, 125-69, 126-69, 127-69, 128-69 and so on showed more than 80% control against wheat powdery mildew; At the dosage of 100 ppm, the compounds 30-1-21, 30-2-19, 31-30, 31-69, 32-17, 32-19, 32-21, 32-30, 32-49, 32-69, 33-4, 33-19, 33-30, 33-49, 33-57, 33-69, 36-19, 37-19, 42-17, 42-57, 42-69, 44-19, 59-21, 118-69, 119-69, 122-69, 123-69, 125-69, 126-69, 127-69, 128-69 and so on showed more than 80% control against wheat powdery mildew; At the dosage of 25 ppm, the compounds 30-2-19, 31-30, 31-69, 32-21, 32-30, 32-69, 33-4, 33-19, 33-30, 33-49, 33-57, 33-69, 36-19, 37-19, 42-69, 44-19, 118-69, 119-69, 122-69, 123-69, 125-69, 126-69, 127-69, 128-69 and so on showed more than 80% control against wheat powdery mildew; At the dosage of 6.25 ppm, the compounds 30-2-19, 31-69, 32-69, 33-4, 33-19, 33-49, 33-57, 33-69, 36-19, 37-19, 42-69, 44-19, 118-69, 123-69, 126-69, 128-69 and so on showed more than 80% control against wheat powdery mildew.

The protective activity against corn rust in vivo:

At the dosage of 400 ppm, the compounds 31-49, 31-57, 31-69, 32-4, 32-18, 32-19, 32-49, 32-57, 32-69, 32-78, 33-4, 33-19, 33-69, 36-19, 37-19, 40-18, 40-21, 42-18, 42-21, 42-4, 42-69, 42-78, 44-19, 57-4, 59-21, 68-4 and so on showed more than 80% control against corn rust; At the dosage of 100 ppm, the compounds 31-69, 31-57, 32-49, 32-57, 32-69, 33-4, 33-69, 37-19, 42-18, 42-69, 44-19, 57-4 and so on showed more than 80% control against corn rust; At the dosage of 25 ppm, the compounds 32-49, 32-57, 32-69, 37-19, 42-69 and so on showed more than 80% control against corn rust; At the dosage of 6.25 ppm, the compounds 32-49, 37-19, 42-69 and so on showed more than 80% control against corn rust.

The protective activity against cucumber anthracnose in vivo:

At the dosage of 400 ppm, the compounds 31-4, 31-19, 31-49, 31-57, 32-4, 32-18, 32-19, 32-49, 33-4, 33-19, 40-4, 40-19, 40-57, 42-1, 42-49, 42-69 and so on showed more than 80% control against cucumber anthracnose; At the dosage of 100 ppm, the compounds 31-19, 31-49, 31-57, 32-4, 32-18, 32-19, 32-49, 33-4, 33-19, 40-4, 40-19, 40-57, 42-1, 42-49, 118-69, 122-69, 123-69, 126-69, 127-69 and so on showed more than 80% control against cucumber anthracnose; At the dosage of 25 ppm, the compounds 31-19, 31-49, 31-57, 32-4, 32-49, 33-4, 32-19, 40-19, 40-57, 42-1, 42-49, 42-69, 122-69, 123-69, 126-69, 127-69 and so on showed more than 80% control against cucumber anthracnose; At the dosage of 6.25 ppm, the compound 31-57, 32-19, 32-49, 40-57 and 42-1 showed 90% control against cucumber anthracnose.

(3) The Contrastive Test Results of Some Compounds and Contrasts

Contrastive tests were carried out between some compounds and contrasts. The test results are listed in table 129-table 132 ("///" in the following tables means no test).

TABLE 129

The comparative test of protective activity against cucumber downy mildew at 25 mg/L

| Compound No. | protective activity (%) |
| --- | --- |
| 30-1-19 | 95 |
| 30-1-21 | 100 |
| 30-1-30 | 98 |
| 30-2-19 | 98 |
| 31-18 | 95 |
| 31-19 | 100 |
| 31-21 | 90 |
| 31-23 | 100 |
| 31-30 | 100 |
| 31-69 | 100 |
| 32-4 | 95 |
| 32-17 | 70 |
| 32-18 | 60 |
| 32-19 | 100 |

TABLE 129-continued

The comparative test of protective activity against cucumber downy mildewat 25 mg/L

| Compound No. | protective activity (%) |
|---|---|
| 32-21 | 70 |
| 32-30 | 100 |
| 33-18 | 85 |
| 33-19 | 95 |
| 33-21 | 100 |
| 33-30 | 100 |
| 33-49 | 100 |
| 33-57 | 100 |
| 35-19 | 100 |
| 36-19 | 100 |
| 40-1 | 70 |
| 40-4 | 100 |
| 40-17 | 70 |
| 40-18 | 100 |
| 40-19 | 96 |
| 40-21 | 100 |
| 40-30 | 100 |
| 42-1 | 100 |
| 42-17 | 100 |
| 42-18 | 100 |
| 42-21 | 100 |
| 42-69 | 80 |
| 44-19 | 100 |
| 126-69 | 70 |
| 127-69 | 70 |
| CK1 | 20 |
| CK2 | 20 |
| CK3 | 0 |
| CK4 | 0 |
| CK5 | 0 |

TABLE 130

The comparative test of protective activity against wheat powdery mildew at 100 mg/L

| Compound No. | protective activity (%) |
|---|---|
| 30-2-19 | 100 |
| 31-30 | 98 |
| 31-69 | 100 |
| 32-19 | 100 |
| 32-21 | 100 |
| 32-30 | 100 |
| 32-69 | 100 |
| 33-4 | 100 |
| 33-19 | 100 |
| 33-30 | 100 |
| 33-49 | 100 |
| 33-57 | 100 |
| 33-69 | 100 |
| 35-19 | 70 |
| 36-19 | 100 |
| 37-19 | 95 |
| 42-69 | 100 |
| 44-19 | 100 |
| 118-69 | 100 |
| 119-69 | 100 |
| 122-69 | 100 |
| 123-69 | 100 |
| 125-69 | 100 |
| 126-69 | 100 |
| 127-69 | 100 |
| 128-69 | 100 |
| CK2 | 50 |
| CK3 | 0 |
| CK4 | 0 |
| CK5 | 0 |

TABLE 131

The comparative test of protective activity against corn rust

| Compound No. | control effect against corn rust (%) | |
|---|---|---|
| | 100 mg/L | 25 mg/L |
| 32-57 | 98 | 85 |
| 32-69 | 90 | 85 |
| 37-19 | 100 | 90 |
| 42-69 | 90 | 85 |
| CK3 | 20 | 0 |
| CK4 | 0 | 0 |
| CK5 | 70 | 60 |

TABLE 132

The comparative test of protective activity against cucumber anthracnose at 100 mg/L

| Compound No. | protective activity (%) | Compound No. | protective activity (%) | Compound No. | 保护活性 (%) protective activity (%) |
|---|---|---|---|---|---|
| 31-19 | 90 | 33-4 | 85 | 122-69 | 85 |
| 31-49 | 85 | 33-19 | 100 | 123-69 | 90 |
| 31-57 | 98 | 40-19 | 100 | 126-69 | 95 |
| 32-4 | 90 | 40-57 | 98 | 127-69 | 92 |
| 32-18 | 85 | 42-1 | 95 | CK3 | 0 |
| 32-19 | 100 | 42-69 | 95 | CK4 | 0 |
| 32-49 | 100 | 118-69 | 80 | CK5 | 0 |

Example 9

Bioactivity Test Against Insects and Mites

Determination of insecticidal activity of compounds of the present invention against a few insects were carried out by the following procedures:

Compounds were dissolved in mixed solvent (acetone:methanol=1:1), and diluted to required concentration with water containing 0.1% of tween 80.

Diamond back moth, armyworm, peach aphid and carmine spider mite were used as targets and the method of spraying by airbrush was used for determination of insecticidal biassays.

(1) Bioactivity Test Against Diamond Back Moth

The method of spraying by airbrush: The cabbage leaves were made into plates of 2 cm diameter by use of punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25° C., 60~70% R.H.). Scores were conducted and mortalities were calculated after 72 h.

Some of test results against diamond back moth:

At the dosage of 600 ppm, the compounds 33-19, 37-19 and so on showed 100% control against diamond back moth.

(2) Bioactivity Test Against Green Peach Aphid

Method: Filter papers were put in culture dishes (Diameter=6 cm), and water was dripped on filter papers for preserving moisture. Green peach aphids (*Myzus Persicae* Sulzer) were maintained on cabbage. Leaves (Diameter=3 cm) of approximately 15-30 aphids were put in the culture dishes. Bioactivity tests were used the method of Airbrush Foliar Spray, pressure=10 psi (0.7 kg/cm2), spray volume=0.5 mL. The studies were conducted at three constant temperatures 25±1 C in incubator cabinets with 60±5% RH. Survey the survival aphids after 48 h and calculate the death rates.

At the dosage of 600 ppm, the compounds 31-49, 32-17, 32-21, 32-30, 32-33, 32-57, 33-21, 33-57, 37-19, 42-1, 42-57, 59-21 and so on showed more than 80% control against Green Peach Aphid; At the dosage of 100 ppm, the compounds 32-21, 33-21, 37-19 and so on showed more than 80% control against Green Peach Aphid; At the dosage of 5 ppm, the compound 33-21 showed 100% control against Green Peach Aphid.

(3) Bioactivity Test Against Carmine Spider Mite

The method: Broadbean shoots with two true leaves in pot were taken, the healthy adults of carmine spider mite were inoculated to the leaves. The adults were counted and then sprayed with airbrush at the pressure of 0.7 kg/cm² and at dose of 0.5 ml. 3 replicates were set for each treatment. And then they were maintained in standard observation room. Scores were conducted and mortalities were calculated after 72 hrs.

Bioactivity Test Against Carmine Spider Mite:

At the dosage of 600 ppm, the compounds 30-1-57, 30-2-19, 31-23, 32-17, 32-21, 32-23, 32-30, 32-57, 32-78, 33-4, 33-57, 36-19, 37-19, 40-4, 42-17, 42-57, 42-78, 44-19, 59-21 and so on showed more than 80% control against carmine spider mite; At the dosage of 100 ppm, the compounds 32-21, 32-57, 36-19, 37-19, 42-57, 44-19 and so on showed more than 80% control against carmine spider mite; At the dosage of 10 ppm, both compounds 32-57 and 37-19 showed more than 80% control against carmine spider mite.

(4) The Contrastive Test Results of Some Compounds and Contrasts

Contrastive tests were carried out between some compounds and contrasts. The test results are listed in table 133 to table 135 ("///" in the following tables means no test).

TABLE 133 contrastive tests against diamond back moth

| Compound No. | Insecticidal activity against diamond back moth (%) 600 mg/L |
|---|---|
| 33-19 | 100 |
| 37-19 | 100 |
| CK1 | 43 |
| CK2 | 20 |
| CK3 | 0 |
| CK4 | 0 |
| CK5 | 0 |

TABLE 134 contrastive tests against peach aphid

| Compound No. | Insecticidal activity against peach aphid (%) 100 mg/L |
|---|---|
| 33-21 | 100 |
| 37-19 | 84 |
| CK1 | 0 |
| CK3 | 30 |
| CK4 | 0 |
| CK5 | 22 |

TABLE 135 contrastive tests against carmine spider mite

| | Insecticidal activity against carmine spider mite (%) | |
|---|---|---|
| Compound No. | 600 mg/L | 100 mg/L |
| 32-57 | 100 | 100 |
| 36-19 | 100 | 98 |
| 37-19 | 100 | 100 |
| 44-19 | 100 | 100 |
| CK3 | 56 | /// |
| CK4 | 59 | /// |
| CK5 | 58 | /// |

We claim:

1. A substituted pyrazole compound containing pyrimidinyl represented by formula I:

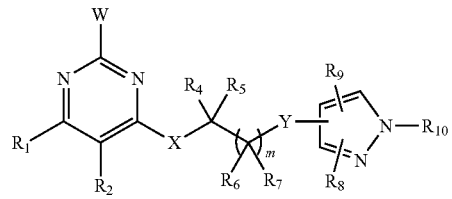

wherein $R_1$ is H, halogen, cyano, nitro, amino, carboxyl, $C_1$-$C_{12}$alkyl, halo$C_1$-$C_{12}$alkyl, $C_3$-$C_{12}$cycloalkyl, $C_1$-$C_{12}$alkoxy, halo$C_1$-$C_{12}$alkoxy, $C_1$-$C_{12}$alkylthio, halo$C_1$-$C_{12}$alkylthio, $C_1$-$C_{12}$alkylsulfinyl, $C_1$-$C_{12}$alkylsulfonyl, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_{12}$alkenoxy, halo$C_3$-$C_{12}$alkenoxy, $C_3$-$C_{12}$alkynoxy, halo$C_3$-$C_{12}$alkynoxy, $C_1$-$C_{12}$alkylamino, di($C_1$-$C_{12}$alkyl)amino, $C_1$-$C_{12}$alkylaminocarbonyl, halo$C_1$-$C_{12}$alkylaminocarbonyl, $C_1$-$C_{12}$alkoxycarbonyl, halo$C_1$-$C_{12}$alkoxycarbonyl, $C_1$-$C_{12}$alkoxy$C_1$-$C_{12}$alkyl, or $C_1$-$C_{12}$alkylthio$C_1$-$C_{12}$alkyl;

$R_2$ is H, halogen, cyano, nitro, amino, carboxyl, CHO, $C_1$-$C_{12}$alkyl, halo$C_1$-$C_{12}$alkyl, $C_1$-$C_{12}$alkoxy, or halo$C_1$-$C_{12}$alkoxy;

$R_1$, $R_2$ and their conjoint pyrimidine ring can also form a five-membered ring, six-membered ring, seven-membered ring or eight-membered ring which contains carbon atom, nitrogen atom, oxygen atom, or sulphur atom;

X is $NR_3$, O, or S;

Y is $NR_3$, O, or S;

$R_3$ is H, OH, CHO, $C_1$-$C_{12}$alkyl, halo$C_1$-$C_{12}$alkyl, $C_1$-$C_{12}$alkoxy, halo$C_1$-$C_{12}$alkoxy, $C_3$-$C_{12}$cycloalkyl, $C_1$-$C_{12}$alkylthio, $C_2$-$C_{12}$alkenylthio, $C_2$-$C_{12}$alkenyl, $C_2$-$C_{12}$alkynyl, halo$C_2$-$C_{12}$alkenyl, halo$C_2$-$C_{12}$alkynyl, $C_1$-$C_{12}$alkoxy$C_1$-$C_{12}$alkyl, halo$C_1$-$C_{12}$alkoxy$C_1$-$C_{12}$alkyl, $C_1$-$C_{12}$alkylthio$C_1$-$C_{12}$alkyl, halo$C_1$-$C_{12}$alkylthio$C_1$-$C_{12}$alkyl, $C_1$-$C_{12}$alkylsulfinyl, halo$C_1$-$C_{12}$alkylsulfinyl, $C_1$-$C_{12}$alkylsulfonyl, halo$C_1$-$C_{12}$alkylsulfonyl, $C_1$-$C_{12}$alkylaminosulfonyl, di($C_1$-$C_{12}$alkyl)aminosulfonyl, $C_1$-$C_{12}$alkylsulfonylaminocarbonyl, $C_1$-$C_{12}$alkylcarbonylaminosulfonyl, $C_3$-$C_{12}$cycloalkyloxycarbonyl, $C_1$-$C_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkylcarbonylC$_1$-C$_{12}$alkyl, C$_1$-C$_{12}$alkoxycarbonylC$_1$-C$_{12}$alkyl, C$_1$-C$_{12}$alkylaminocarbonyl, di(C$_1$-C$_{12}$alkyl)aminocarbonyl, C$_2$-C$_{12}$alkenoxycarbonyl, C$_2$-C$_{12}$alkynoxycarbonyl, C$_1$-C$_{12}$alkoxyC$_1$-C$_{12}$alkoxycarbonyl, C$_1$-C$_{12}$alkylaminothio, di(C$_1$-C$_{12}$alkyl)aminothio, unsubstituted or further substituted (hetero)arylcarbonylC$_1$-C$_6$alkyl, (hetero)arylcarbonyl, (hetero)aryloxycarbonyl, (hetero)arylC$_1$-C$_6$alkyloxycarbonyl, or (hetero)arylC$_1$-C$_6$alkyl by 1 to 5 following groups: halo, nitro, cyano, C$_1$-C$_6$alkyl, haloC$_1$-C$_6$alkyl, C$_1$-C$_6$alkoxy, or haloC$_1$-C$_6$alkoxy;

R$_4$ and R$_5$ may be the same or different and are each independently H, halogen, C$_1$-C$_{12}$alkyl, haloC$_1$-C$_{12}$alkyl, C$_1$-C$_{12}$alkoxy, or haloC$_1$-C$_{12}$alkoxy; or R$_4$, R$_5$ and their conjoint carbon can also form a C$_3$-C$_8$ cycle;

R$_6$ and R$_7$ may be the same or different and are each independently H, halogen, C$_1$-C$_{12}$alkyl, haloC$_1$-C$_{12}$alkyl, C$_1$-C$_{12}$alkoxy, or haloC$_1$-C$_{12}$alkoxy; or R$_6$, R$_7$ and their conjoint carbon can also form a C$_3$-C$_8$ cycle;

m is an integer selected from 0 to 5;

R$_8$ is H, cyano, halogen, C$_1$-C$_{12}$alkyl, haloC$_1$-C$_{12}$alkyl, C$_1$-C$_{12}$alkoxycarbonyl, haloC$_1$-C$_{12}$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 R$_{11}$;

R$_9$ is H, cyano, halogen, C$_1$-C$_{12}$alkyl, haloC$_1$-C$_{12}$alkyl, C$_1$-C$_{12}$alkoxycarbonyl, haloC$_1$-C$_{12}$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 R$_{11}$;

R$_{10}$ is C$_1$-C$_{12}$alkyl, C$_3$-C$_8$cycloalkyl, haloC$_1$-C$_{12}$alkyl, C$_1$-C$_{12}$alkylcarbonyl, haloC$_1$-C$_{12}$alkylcarbonyl, C$_1$-C$_{12}$alkylsulfonyl, haloC$_1$-C$_{12}$alkylsulfonyl, C$_1$-C$_{12}$alkoxycarbonyl, C$_1$-C$_{12}$alkoxyC$_1$-C$_{12}$alkyl, C$_1$-C$_{12}$alkoxycarbonylC$_1$-C$_{12}$alkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 R$_{11}$;

R$_{11}$ is halogen, OH, amino, cyano, nitro, C$_1$-C$_{12}$alkyl, haloC$_1$-C$_{12}$alkyl, C$_1$-C$_{12}$alkoxy, haloC$_1$-C$_{12}$alkoxy, C$_3$-C$_{12}$cycloalkyl, C$_1$-C$_{12}$alkylamino, haloC$_1$-C$_{12}$alkylamino, di(C$_1$-C$_{12}$alkyl)amino, halodi(C$_1$-C$_{12}$alkyl)amino, C(=O)NR$_{12}$R$_{12}$, C$_1$-C$_{12}$alkylthio, haloC$_1$-C$_{12}$alkylthio, C$_2$-C$_{12}$alkenyl, C$_2$-C$_{12}$alkynyl, C$_2$-C$_{12}$alkenoxy, haloC$_2$-C$_{12}$alkenoxy, C$_2$-C$_{12}$alkynoxy, haloC$_2$-C$_{12}$alkynoxy, C$_1$-C$_{12}$alkylsulfonyl, haloC$_1$-C$_{12}$alkylsulfonyl, C$_1$-C$_{12}$alkylcarbonyl, haloC$_1$-C$_{12}$alkylcarbonyl, C$_1$-C$_{12}$alkoxycarbonyl, haloC$_1$-C$_{12}$alkoxycarbonyl, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkylthioC$_1$-C$_{12}$alkyl, haloC$_1$-C$_{12}$alkylthioC$_1$-C$_{12}$alkyl, C$_1$-C$_{12}$alkoxycarbonylC$_1$-C$_{12}$alkyl, haloC$_1$-C$_{12}$alkoxycarbonylC$_1$-C$_{12}$alkyl, C$_1$-C$_{12}$alkylthiocarbonylC$_1$-C$_{12}$alkyl, haloC$_1$-C$_{12}$alkylthiocarbonylC$_1$-C$_{12}$alkyl, C$_1$-C$_{12}$alkylcarbonyloxy, haloC$_1$-C$_{12}$alkylcarbonyloxy, C$_1$-C$_{12}$alkoxycarbonyloxy, haloC$_1$-C$_{12}$alkoxycarbonyloxy, C$_1$-C$_{12}$alkylsulfonyloxy, haloC$_1$-C$_{12}$alkylsulfonyloxy, C$_1$-C$_{12}$alkoxyC$_1$-C$_{12}$alkoxy, or haloC$_1$-C$_{12}$alkoxyC$_1$-C$_{12}$alkoxy;

R$_{12}$ and R$_{13}$ may be the same or different and are each independently H, C$_1$-C$_{12}$alkyl, or haloC$_1$-C$_{12}$alkyl;

W is H, halogen, C$_1$-C$_{12}$alkyl, haloC$_1$-C$_{12}$alkyl, C$_3$-C$_8$cycloalkyl, C$_1$-C$_{12}$alkoxy, C$_1$-C$_{12}$alkylthio, or C$_1$-C$_{12}$alkylsulfonyl; and the position of Y linked to pyrazole ring is from 3-position, 4-position, or 5-position; when Y is linked to 3-position of pyrazole, R$_8$ is at the 4-position R$_9$ is at the 5-position; when Y is linked to 4-position of pyrazole, R$_8$ is at the 3-position R$_9$ is at the 5-position; when Y is linked to 5-position of pyrazole, R$_8$ is at the 3-position R$_9$ is at the 4-position;

or a salt thereof.

2. The substituted pyrazole compound containing pyrimidinyl according to claim 1, wherein R$_1$ is H, halogen, cyano, nitro, amino, carboxyl, C$_1$-C$_6$alkyl, haloC$_1$-C$_6$alkyl, C$_3$-C$_6$cycloalkyl, C$_1$-C$_6$alkoxy, haloC$_1$-C$_6$alkoxy, C$_1$-C$_6$alkylthio, C$_1$-C$_6$alkylsulfinyl, C$_1$-C$_6$alkylsulfonyl, haloC$_1$-C$_6$alkylthio, C$_2$-C$_6$alkenyl, haloC$_2$-C$_6$alkenyl, C$_2$-C$_6$alkynyl, haloC$_2$-C$_6$alkynyl, C$_3$-C$_6$alkenoxy, haloC$_3$-C$_6$alkenoxy, C$_3$-C$_6$alkynoxy, haloC$_3$-C$_6$alkynoxy, C$_1$-C$_6$alkylamino, di(C$_1$-C$_6$alkyl)amino, C$_1$-C$_6$alkylaminocarbonyl, haloC$_1$-C$_6$alkylaminocarbonyl, C$_1$-C$_6$alkoxycarbonyl, haloC$_1$-C$_6$alkoxycarbonyl, C$_1$-C$_6$alkoxyC$_1$-C$_6$alkyl, or C$_1$-C$_6$alkylthioC$_1$-C$_6$alkyl;

R$_2$ is H, halogen, cyano, nitro, amino, carboxyl, CHO, C$_1$-C$_6$alkyl, haloC$_1$-C$_6$alkyl, C$_1$-C$_6$alkoxy, or haloC$_1$-C$_6$alkoxy;

R$_1$, R$_2$ and their conjoint pyrimidine ring can also form a five-membered ring or six-membered ring which contains carbon atom, nitrogen atom, oxygen atom, or sulphur atom;

X is NR$_3$, O, or S;

Y is NR$_3$, O, or S;

R$_3$ is H, OH, CHO, C$_1$-C$_6$alkyl, haloC$_1$-C$_6$alkyl, C$_1$-C$_6$alkoxy, haloC$_1$-C$_6$alkoxy, C$_3$-C$_6$cycloalkyl, C$_1$-C$_6$alkylthio, C$_2$-C$_6$alkenylthio, C$_2$-C$_6$alkenyl, C$_2$-C$_6$alkynyl, haloC$_2$-C$_6$alkenyl, haloC$_2$-C$_6$alkynyl, C$_1$-C$_6$alkoxyC$_1$-C$_6$alkyl, haloC$_1$-C$_6$alkoxyC$_1$-C$_6$alkyl, C$_1$-C$_6$alkylthioC$_1$-C$_6$alkyl, haloC$_1$-C$_6$alkylthioC$_1$-C$_6$alkyl, C$_1$-C$_6$alkylsulfinyl, haloC$_1$-C$_6$alkylsulfinyl, C$_1$-C$_6$alkylsulfonyl, haloC$_1$-C$_6$alkylsulfonyl, C$_1$-C$_6$alkylaminosulfonyl, di(C$_1$-C$_6$alkyl)aminosulfonyl, C$_1$-C$_6$alkylsulfonylaminocarbonyl, C$_1$-C$_6$alkylcarbonylaminosulfonyl, C$_3$-C$_6$cycloalkyloxycarbonyl, C$_1$-C$_6$alkylcarbonyl, haloC$_1$-C$_6$alkylcarbonyl, C$_1$-C$_6$alkoxycarbonyl, haloC$_1$-C$_6$alkoxycarbonyl, C$_1$-C$_6$alkylcarbonylC$_1$C$_6$alkyl, C$_1$-C$_6$alkoxycarbonylC$_1$-C$_6$alkyl, C$_1$-C$_6$alkylaminocarbonyl, di(C$_1$-C$_6$alkyl)aminocarbonyl, C$_2$-C$_6$alkenoxycarbonyl, C$_2$-C$_6$alkynoxycarbonyl, C$_1$-C$_6$alkoxyC$_1$-C$_6$alkoxycarbonyl, C$_1$-C$_6$alkylaminothio, di(C$_1$-C$_6$alkyl)aminothio, unsubstituted or further substituted (hetero)arylcarbonylC$_1$-C$_6$alkyl, (hetero)arylcarbonyl, (hetero)aryloxycarbonyl, (hetero)arylC$_1$-C$_6$alkyloxycarbonyl, or (hetero)arylC$_1$-C$_6$alkyl by 1 to 5 following groups: halogen, nitro, cyano, C$_1$-C$_6$alkyl, haloC$_1$-C$_6$alkyl, C$_1$-C$_6$alkoxy, or haloC$_1$-C$_6$alkoxy;

R$_4$ and R$_5$ may be the same or different and are each independently H, halogen, C$_1$-C$_6$alkyl, haloC$_1$-C$_6$alkyl, C$_1$-C$_6$alkoxy, or haloC$_1$-C$_6$alkoxy; or R$_4$, R$_5$ and their conjoint carbon can also form a C$_3$-C$_6$ cycle;

$R_6$ and $R_7$ may be the same or different and are each independently H, halogen, $C_1$-$C_6$alkyl, halo$C_1$-$C_6$alkyl, $C_1$-$C_6$alkoxy, or halo$C_1$-$C_6$alkoxy; or $R_6$, $R_7$ and their conjoint carbon can also form a $C_3$-$C_6$ cycle;

m is selected from 0 to 4;

$R_8$ is H, cyano, halogen, $C_1$-$C_6$alkyl, halo$C_1$-$C_6$alkyl, $C_1$-$C_6$alkoxycarbonyl, halo$C_1$-$C_6$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_9$ is H, cyano, halogen, $C_1$-$C_6$alkyl, halo$C_1$-$C_6$alkyl, $C_1$-$C_6$alkoxycarbonyl, halo$C_1$-$C_6$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{10}$ is $C_1$-$C_6$alkyl, $C_3$-$C_6$cycloalkyl, halo$C_1$-$C_6$alkyl, $C_1$-$C_6$alkylcarbonyl, halo$C_1$-$C_6$alkylcarbonyl, $C_1$-$C_6$alkylsulfonyl, halo$C_1$-$C_6$alkylsulfonyl, $C_1$-$C_6$alkoxycarbonyl, $C_1$-$C_6$alkoxy$C_1$-$C_6$alkyl, $C_1$-$C_6$alkoxycarbonyl$C_1$-$C_6$alkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{11}$ is halogen, OH, amino, cyano, nitro, $C_1$-$C_6$alkyl, halo$C_1$-$C_6$alkyl, $C_1$-$C_6$alkoxy, halo$C_1$-$C_6$alkoxy, $C_3$-$C_6$cycloalkyl, $C_1$-$C_6$alkylamino, halo$C_1$-$C_6$alkylamino, di($C_1$-$C_6$alkyl)amino, halodi($C_1$-$C_6$alkyl)amino, C(=O)N$R_{12}R_{13}$, $C_1$-$C_6$alkylthio, halo$C_1$-$C_6$alkylthio, $C_2$-$C_6$alkenyl, $C_2$-$C_6$alkynyl, $C_2$-$C_6$alkenoxy, halo$C_2$-$C_6$alkenoxy, $C_2$-$C_6$alkynoxy, halo$C_2$-$C_6$alkynoxy, $C_1$-$C_6$alkylsulfonyl, halo$C_1$-$C_6$alkylsulfonyl, $C_1$-$C_6$alkylcarbonyl, halo$C_1$-$C_6$alkylcarbonyl, $C_1$-$C_6$alkoxycarbonyl, halo$C_1$-$C_6$alkoxycarbonyl, $C_1$-$C_6$alkoxy$C_1$-$C_6$alkyl, halo$C_1$-$C_6$alkoxy$C_1$-$C_6$alkyl, $C_1$-$C_6$alkylthio$C_1$-$C_6$alkyl, halo$C_1$-$C_6$alkylthio$C_1$-$C_6$alkyl, $C_1$-$C_6$alkoxycarbonyl$C_1$-$C_6$alkyl, halo$C_1$-$C_6$alkoxycarbonyl$C_1$-$C_6$alkyl, $C_1$-$C_6$alkylthiocarbonyl$C_1$-$C_6$alkyl, halo$C_1$-$C_6$alkylthiocarbonyl$C_1$-$C_6$alkyl, $C_1$-$C_6$alkylcarbonyloxy, halo$C_1$-$C_6$alkylcarbonyloxy, $C_1$-$C_6$alkoxycarbonyloxy, halo$C_1$-$C_6$alkoxycarbonyloxy, $C_1$-$C_6$alkylsulfonyloxy, halo$C_1$-$C_6$alkylsulfonyloxy, $C_1$-$C_6$alkoxy$C_1$-$C_6$alkoxy, or halo$C_1$-$C_6$alkoxy$C_1$-$C_6$alkoxy;

$R_{12}$ and $R_{13}$ may be the same or different and are each independently H, $C_1$-$C_6$alkyl, or halo$C_1$-$C_6$alkyl; and W is H, halogen, $C_1$-$C_6$alkyl, halo$C_1$-$C_6$alkyl, $C_3$-$C_6$cycloalkyl, $C_1$-$C_6$alkoxy, $C_1$-$C_6$alkylthio, or $C_1$-$C_6$alkylsulfonyl.

3. The substituted pyrazole compound containing pyrimidinyl according to claim 2, wherein $R_1$ is H, halogen, cyano, nitro, amino, carboxyl, $C_1$-$C_4$alkyl, halo$C_1$-$C_4$alkyl, $C_3$-$C_4$cycloalkyl, $C_1$-$C_4$alkoxy, halo$C_1$-$C_4$alkoxy, $C_1$-$C_4$alkylthio, $C_1$-$C_4$alkylsulfinyl, $C_1$-$C_4$alkylsulfonyl, halo$C_1$-$C_4$alkylthio, $C_2$-$C_4$alkenyl, halo$C_2$-$C_4$alkenyl, $C_2$-$C_4$alkynyl, halo$C_2$-$C_4$alkynyl, $C_3$-$C_4$alkenoxy, halo$C_3$-$C_4$alkenoxy, $C_3$-$C_4$alkynoxy, halo$C_3$-$C_4$alkynoxy, $C_1$-$C_4$alkylamino, di($C_1$-$C_4$alkyl)amino, $C_1$-$C_4$alkylaminocarbonyl, halo$C_1$-$C_4$alkylaminocarbonyl, $C_1$-$C_4$alkoxycarbonyl, halo$C_1$-$C_4$alkoxycarbonyl, $C_1$-$C_4$alkoxy$C_1$-$C_4$alkyl, or $C_1$-$C_4$alkylthio$C_1$-$C_4$alkyl;

$R_2$ is H, halogen, cyano, nitro, amino, carboxyl, CHO, $C_1$-$C_4$alkyl, halo$C_1$-$C_4$alkyl, $C_1$-$C_4$alkoxy, or halo$C_1$-$C_4$alkoxy;

$R_1$, $R_2$ and their conjoint pyrimidine ring can also form a five-membered ring, or six-membered ring which contains carbon atom, nitrogen atom, oxygen atom, or sulphur atom;

X is N$R_3$, O, or S;

$R_3$ is H, OH, CHO, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylthio, $C_2$-$C_4$alkenylthio, $C_2$-$C_4$alkenyl, $C_2$-$C_4$alkynyl, halo$C_2$-$C_4$alkenyl, halo$C_2$-$C_4$alkynyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, di($C_1$-$C_4$alkyl)aminosulfonyl, $C_1$-$C_4$alkylsulfonylaminocarbonyl, $C_1$-$C_4$alkylcarbonylaminosulfonyl, $C_3$-$C_4$cycloalkyloxycarbonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkylcarbonyl$C_1$-$C_4$alkyl, $C_1$-$C_4$alkoxycarbonyl$C_1$-$C_4$alkyl, $C_1$-$C_4$alkylaminocarbonyl, di($C_1$-$C_4$alkyl)aminocarbonyl, $C_2$-$C_4$alkenoxycarbonyl, $C_2$-$C_4$alkynoxycarbonyl, $C_1$-$C_4$alkoxy$C_1$-$C_4$alkoxycarbonyl, $C_1$-$C_4$alkylaminothio, di($C_1$-$C_4$alkyl)aminothio, unsubstituted or further substituted (hetero)arylcarbonyl$C_1$-$C_4$alkyl, (hetero)arylcarbonyl, (hetero)aryloxycarbonyl, (hetero)aryl$C_1$-$C_4$alkyloxycarbonyl, or (hetero)aryl$C_1$-$C_4$alkyl by 1 to 5 following groups: halogen, nitro, cyano, $C_1$-$C_4$alkyl, halo$C_1$-$C_4$alkyl, $C_1$-$C_4$alkoxy, or halo$C_1$-$C_4$alkoxy;

$R_4$ and $R_5$ may be the same or different and are each independently H, halogen, $C_1$-$C_4$alkyl, halo$C_1$-$C_4$alkyl, $C_1$-$C_4$alkoxy, or halo$C_1$-$C_4$alkoxy; or $R_4$, $R_5$ and their conjoint carbon can also form a $C_3$-$C_4$ cycle;

$R_6$ and $R_7$ may be the same or different and are each independently H, halogen, $C_1$-$C_4$alkyl, halo$C_1$-$C_4$alkyl, $C_1$-$C_4$alkoxy, or halo$C_1$-$C_4$alkoxy; or $R_6$, $R_7$ and their conjoint carbon can also form a $C_3$-$C_4$ cycle;

m is selected from 0 to 3;

$R_8$ is H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_9$ is H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{10}$ is $C_1$-$C_4$alkyl, $C_3$-$C_4$cycloalkyl, halo$C_1$-$C_4$alkyl, $C_1$-$C_4$alkylcarbonyl, halo$C_1$-$C_4$alkylcarbonyl, $C_1$-$C_4$alkylsulfonyl, halo$C_1$-$C_4$alkylsulfonyl, $C_1$-$C_4$alkoxycarbonyl, $C_1$-$C_4$alkoxy$C_1$-$C_4$alkyl, $C_1$-$C_4$alkoxycarbonyl$C_1$-$C_4$alkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{11}$ is halogen, OH, amino, cyano, nitro, $C_1C_4$alkyl, halo$C_1$-$C_4$alkyl, $C_1$-$C_4$alkoxy, halo$C_1$ -$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, C(=O)N$R_{12}R_{13}$, $C_1$-$C_4$alkylthio, haloC$_1$-C$_4$alkylthio, C$_2$-C$_4$alkenyl, C$_2$-C$_4$alkynyl, C$_2$-C$_4$alkenoxy, haloC$_2$-C$_4$alkenoxy, C$_2$-C$_4$alkynoxy, haloC$_2$-C$_4$alkynoxy, C$_1$-C$_4$alkylsulfonyl, haloC$_1$-C$_4$alkylsulfonyl, C$_1$-C$_4$alkylcarbonyl, haloC$_1$-C$_4$alkylcarbonyl, C$_1$-C$_4$alkoxycarbonyl, haloC$_1$-C$_4$alkoxycarbonyl, C$_1$-C$_4$alkoxyC$_1$-C$_4$alkyl, haloC$_1$-C$_4$alkoxyC$_1$-C$_4$alkyl, C$_1$-C$_4$alkylthioC$_1$-C$_4$alkyl, haloC$_1$-C$_4$alkylthioC$_1$-C$_4$alkyl, C$_1$-C$_4$alkoxycarbonylC$_1$-C$_4$alkyl, haloC$_1$-C$_4$alkoxycarbonylC$_1$-C$_4$alkyl, C$_1$-C$_4$alkylthiocarbonylC$_1$-C$_4$alkyl, haloC$_1$-C$_4$alkylthiocarbonylC$_1$-C$_4$alkyl, C$_1$-C$_4$alkylcarbonyloxy, haloC$_1$-C$_4$alkylcarbonyloxy, C$_1$-C$_4$alkoxycarbonyloxy, haloC$_1$-C$_4$alkoxycarbonyloxy, C$_1$-C$_4$alkylsulfonyloxy, haloC$_1$-C$_4$alkylsulfonyloxy, C$_1$-C$_4$alkoxyC$_1$-C$_4$alkoxy, or haloC$_1$-C$_4$alkoxyC$_1$-C$_4$alkoxy;

$R_{12}$ and $R_{13}$ may be the same or different and are each independently H, C$_1$-C$_4$alkyl, or haloC$_1$-C$_4$alkyl;

W is H, halogen, C$_1$-C$_4$alkyl, haloC$_1$-C$_4$alkyl, C$_3$-C$_4$cycloalkyl, C$_1$-C$_4$alkoxy, C$_1$-C$_4$alkylthio, or C$_1$-C$_4$alkylsulfonyl; and Y is O, the position of Y linked to pyrazole ring is from 3-position, 4-position, or 5-position; when Y is linked to 3-position of pyrazole, $R_8$ is at the 4-position and $R_9$ is at the 5-position, formula I is represented by formula I-1; when Y is linked to 4-position of pyrazole, $R_8$ is at the 3-position and $R_9$ is at the 5-position, formula I is represented by formula I-2; when Y is linked to 5-position of pyrazole, $R_8$ is at the 3-position and $R_9$ is at the 4-position, formula I is represented by formula I-3;

I-1

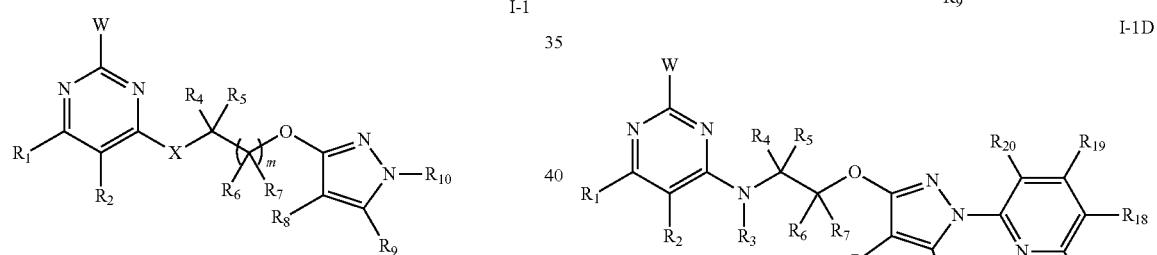

I-2

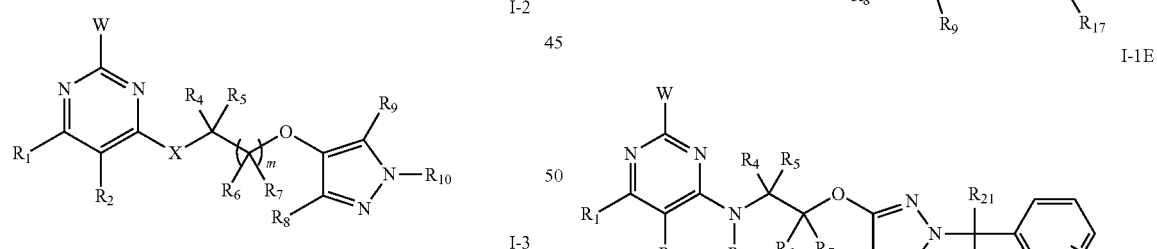

I-3

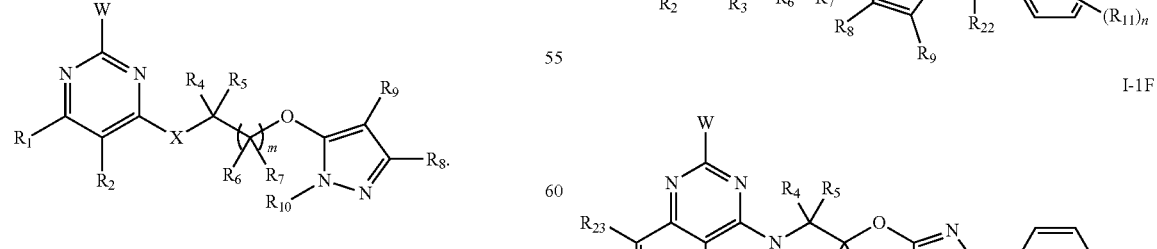

4. A substituted pyrazole compound containing pyrimidinyl represented by formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F, I-3G, I-4C, I-4F, I-4G, or a salt thereof:

I-1A

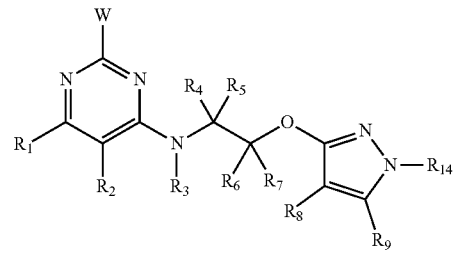

I-1B

I-1C

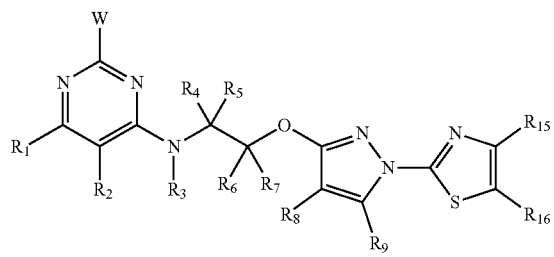

I-1D

I-1E

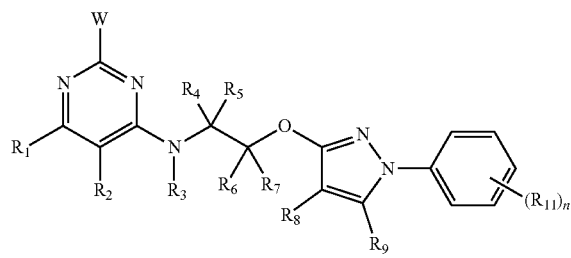

I-1F

I-1G
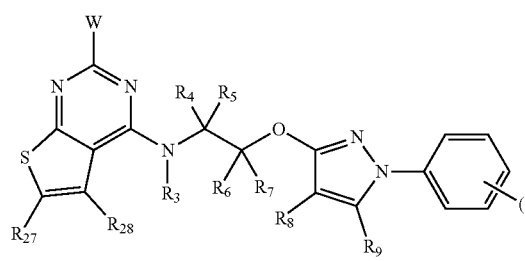
I-1H
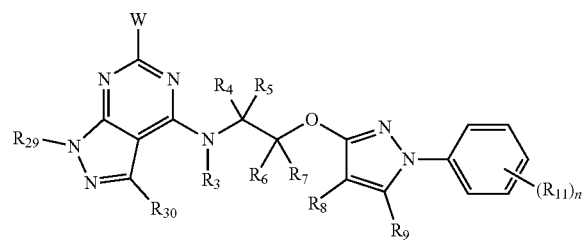
I-1I
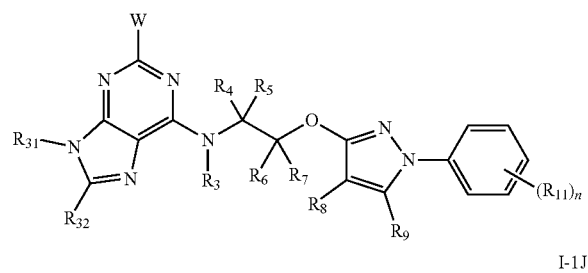
I-1J
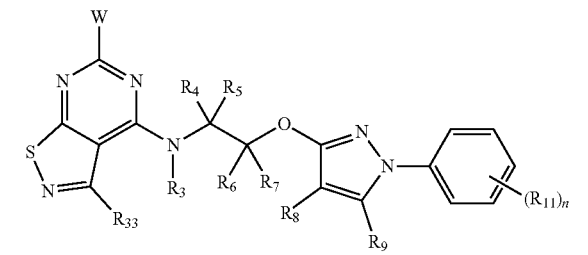
I-1K
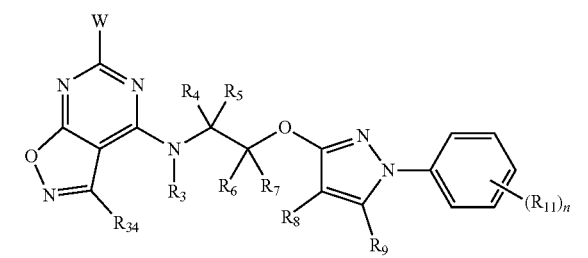
I-1L
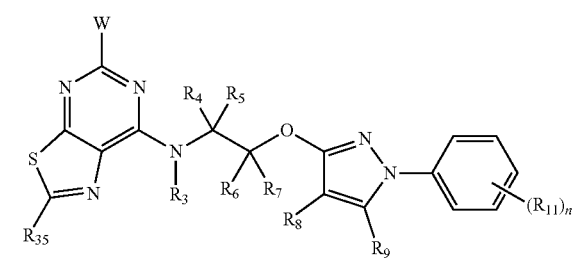
I-1M
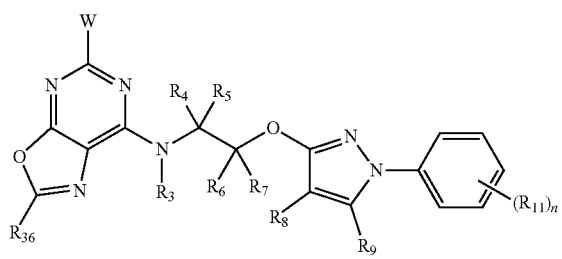
I-1N
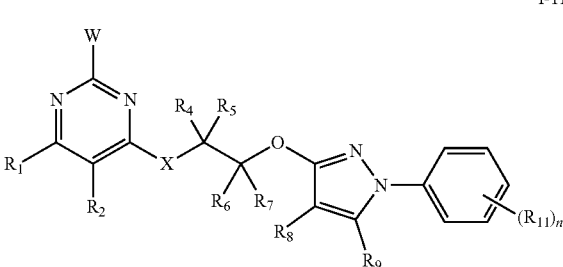
(X = O or S)
I-2A
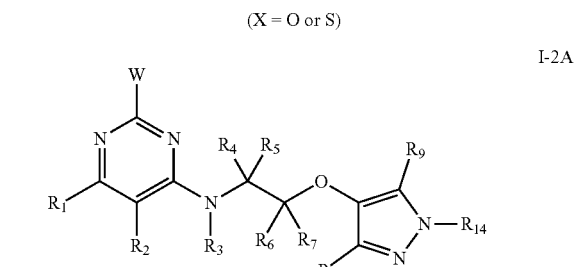
I-2B
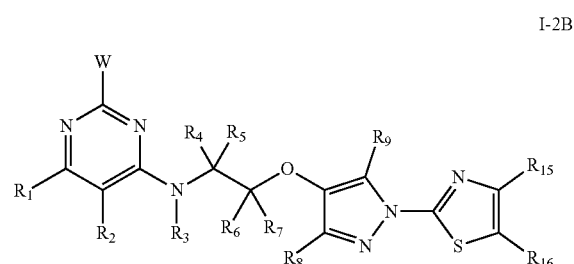
I-2C
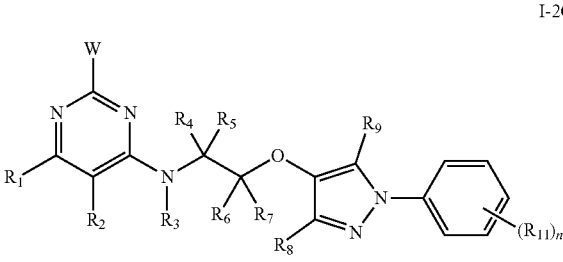
I-2D
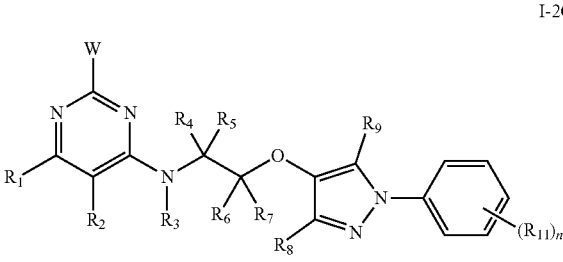

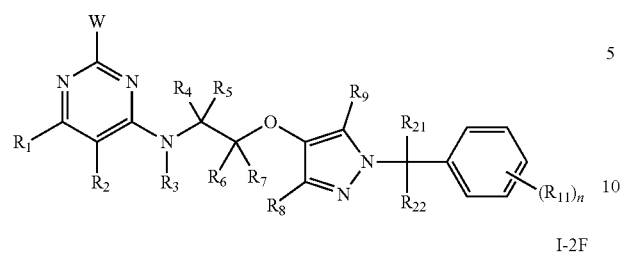
I-2E
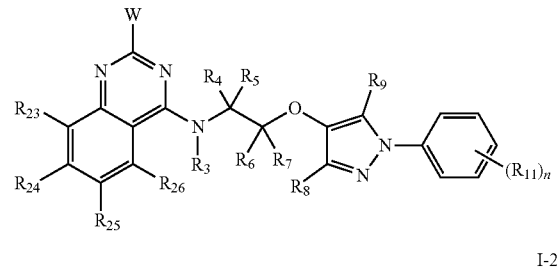
I-2F
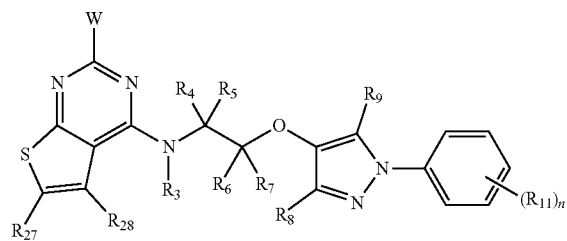
I-2G
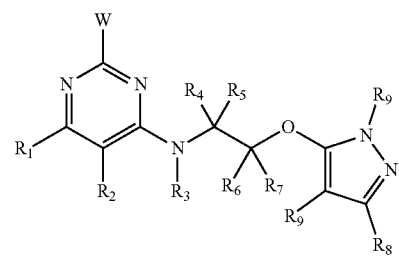
I-3A
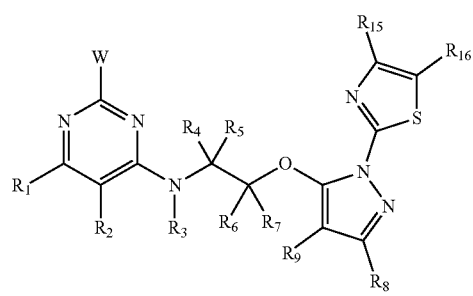
I-3B
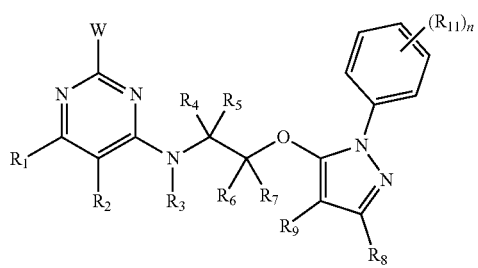
I-3C
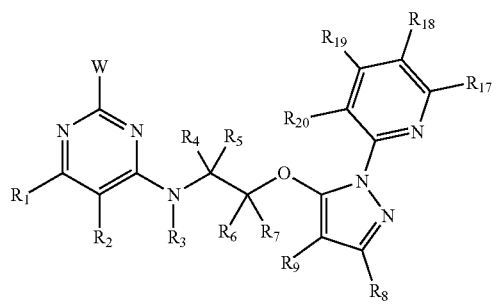
I-3D
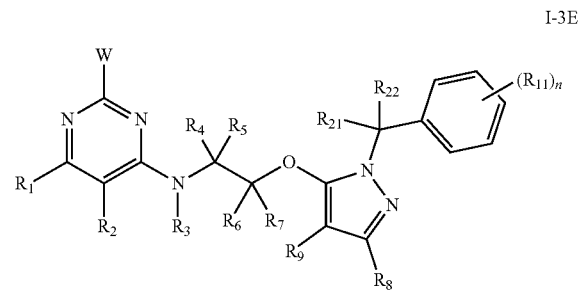
I-3E
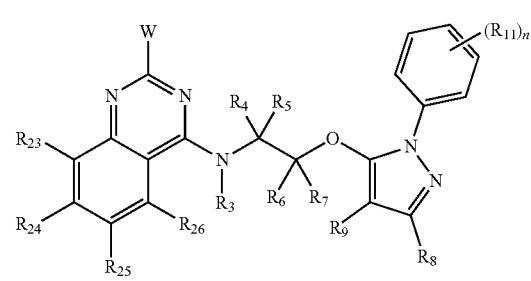
I-3F
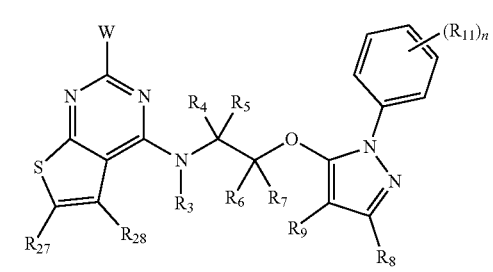
I-3G
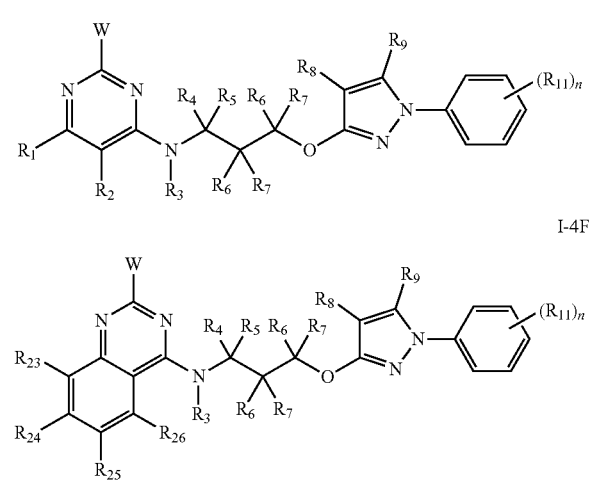
I-4C
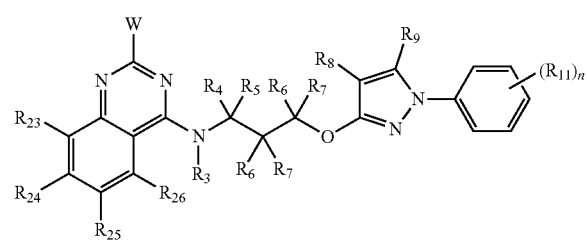
I-4F -continued

I-4G

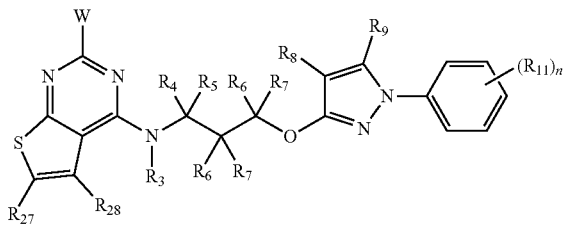

wherein $R_1$ is H, halogen, cyano, nitro, amino, carboxyl, $C_1$-$C_4$alkyl, halo$C_1$-$C_4$alkyl, $C_3$-$C_4$cycloalkyl, $C_1$-$C_4$alkoxy, halo$C_1$-$C_4$alkoxy, $C_1$-$C_4$alkylthio, halo$C_1$-$C_4$alkylthio, $C_1$-$C_4$alkylsulfinyl, $C_1$-$C_4$alkylsulfonyl, $C_2$-$C_4$alkenyl, halo$C_2$-$C_4$alkenyl, $C_2$-$C_4$alkynyl, halo$C_2$-$C_4$alkynyl, $C_3$-$C_4$alkenoxy, halo$C_3$-$C_4$alkenoxy, $C_3$-$C_4$alkynoxy, halo$C_3$-$C_4$alkynoxy, $C_1$-$C_4$alkylamino, di($C_1$-$C_4$alkyl)amino, $C_1$-$C_4$alkylaminocarbonyl, halo$C_1$-$C_4$alkylaminocarbonyl, $C_1$-$C_4$alkoxycarbonyl, halo$C_1$-$C_4$alkoxycarbonyl, $C_1$-$C_4$alkoxy$C_1$-$C_4$alkyl, or $C_1$-$C_4$alkylthio$C_1$-$C_4$alkyl;

$R_2$ is H, halogen, cyano, nitro, amino, carboxyl, CHO, $C_1$-$C_4$alkyl, halo$C_1$-$C_4$alkyl, $C_1$-$C_4$alkoxy, or halo$C_1$-$C_4$alkoxy;

$R_3$ is H, OH, CHO, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylthio, $C_2$-$C_4$alkenylthio, $C_2$-$C_4$alkenyl, $C_2$-$C_4$alkynyl, halo$C_2$-$C_4$alkenyl, halo$C_2$-$C_4$alkynyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkylsulfinyl, halo$C_1$-$C_4$alkylsulfinyl, $C_1$-$C_4$alkylsulfonyl, halo$C_1$-$C_4$alkylsulfonyl, $C_1$-$C_4$alkylaminosulfonyl, di($C_1$-$C_4$alkyl)aminosulfonyl, $C_1$-$C_4$alkylsulfonylaminocarbonyl, $C_1$-$C_4$alkylcarbonylaminosulfonyl, $C_3$-$C_4$cycloalkyloxycarbonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkylcarbonyl$C_1$-$C_4$alkyl, $C_1$-$C_4$alkoxycarbonyl$C_1$-$C_4$alkyl, $C_1$-$C_4$alkylaminocarbonyl, di($C_1$-$C_4$alkyl)aminocarbonyl, $C_2$-$C_4$alkenoxycarbonyl, $C_2$-$C_4$alkynoxycarbonyl, $C_1$-$C_4$alkoxy$C_1$-$C_4$alkoxycarbonyl, $C_1$-$C_4$alkylaminothio, di($C_1$-$C_4$alkyl)aminothio, unsubstituted or further substituted (hetero)arylcarbonyl$C_1$-$C_4$alkyl, (hetero)arylcarbonyl, (hetero)aryloxycarbonyl, (hetero)aryl$C_1$-$C_4$alkyloxycarbonyl, or (hetero)aryl$C_1$-$C_4$alkyl by 1 to 5 following groups: halogen, nitro, cyano, $C_1$-$C_4$alkyl, halo$C_1$-$C_4$alkyl, $C_1$-$C_4$alkoxy, or halo$C_1$-$C_4$alkoxy;

$R_4$ and $R_5$ may be the same or different and are each independently H, halogen, $C_1$-$C_4$alkyl, halo$C_1$-$C_4$alkyl, $C_1$-$C_4$alkoxy, or halo$C_1$-$C_4$alkoxy; or $R_4$, $R_5$ and their conjoint carbon can also form a $C_3$-$C_4$ cycle;

$R_6$ and $R_7$ may be the same or different and are each independently H, halogen, $C_1$-$C_4$alkyl, halo$C_1$-$C_4$alkyl, $C_1$-$C_4$alkoxy, or halo$C_1$-$C_4$alkoxy; or $R_6$, $R_7$ and their conjoint carbon can also form a $C_3$-$C_4$ cycle;

$R_8$ is H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_9$ is H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{11}$ is halogen, OH, amino, cyano, nitro, $C_1$-$C_4$alkyl, halo$C_1$-$C_4$alkyl, $C_1$-$C_4$alkoxy, halo$C_1$-$C_4$alkoxy, $C_3$-$C_4$cycloalkyl, $C_1$-$C_4$alkylamino, halo$C_1$-$C_4$alkylamino, di($C_1$-$C_4$alkyl)amino, halodi($C_1$-$C_4$alkyl)amino, $C(=O)NR_{12}R_{13}$, $C_1$-$C_4$alkylthio, halo$C_1$-$C_4$alkylthio, $C_2$-$C_4$alkenyl, $C_2$-$C_4$alkynyl, $C_2$-$C_4$alkenoxy, halo$C_2$-$C_4$alkenoxy, $C_2$-$C_4$alkynoxy, halo$C_2$-$C_4$alkynoxy, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, $C_1$-$C_4$alkoxy$C_1$-$C_4$alkyl, halo$C_1$-$C_4$alkoxy$C_1$-$C_4$alkyl, $C_1$-$C_4$alkylthio$C_1$-$C_4$alkyl, halo$C_1$-$C_4$alkylthio$C_1$-$C_4$alkyl, $C_1$-$C_4$alkoxycarbonyl$C_1$-$C_4$alkyl, halo$C_1$-$C_4$alkoxycarbonyl$C_1$-$C_4$alkyl, $C_1$-$C_4$alkylthiocarbonyl$C_1$-$C_4$alkyl, halo$C_1$-$C_4$alkylthiocarbonyl$C_1$-$C_4$alkyl, $C_1$-$C_4$alkylcarbonyloxy, halo$C_1$-$C_4$alkylcarbonyloxy, $C_1$-$C_4$alkoxycarbonyloxy, halo$C_1$-$C_4$alkoxycarbonyloxy, $C_1$-$C_4$alkylsulfonyloxy, halo$C_1$-$C_4$alkylsulfonyloxy, $C_1$-$C_4$alkoxy$C_1$-$C_4$alkoxy, or halo$C_1$-$C_4$alkoxy$C_1$-$C_4$alkoxy;

n is an integer selected from 0 to 5, when n is 0, the benzene ring is unsubstituted phenyl; when n is more than 1, $R_{11}$ may be the same or different;

$R_{12}$ and $R_{13}$ may be the same or different and are each independently H, $C_1$-$C_4$alkyl, or halo$C_1$-$C_4$alkyl;

$R_{14}$ is $C_1$-$C_4$alkyl, $C_3$-$C_4$cycloalkyl, halo$C_1$-$C_4$alkyl, $C_1$-$C_4$alkylcarbonyl, halo$C_1$-$C_4$alkylcarbonyl, $C_1$-$C_4$alkylsulfonyl, halo$C_1$-$C_4$alkylsulfonyl, $C_1$-$C_4$alkoxycarbonyl, $C_1$-$C_4$alkoxy$C_1$-$C_4$alkyl, or $C_1$-$C_4$alkoxycarbonyl$C_1$-$C_4$alkyl;

$R_{15}$ and $R_{16}$ may be the same or different and are each independently H, halogen, amino, cyano, nitro, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{17}$, $R_{18}$, $R_{19}$, and $R_{20}$ may be the same or different and are each independently H, halogen, cyano, nitro, $C_1$-$C_4$alkyl, halo$C_1$-$C_4$alkyl, $C_1$-$C_4$alkoxy, or halo$C_1$-$C_4$alkoxy;

$R_{21}$ and $R_{22}$ may be the same or different and are each independently H, halogen, OH, cyano, nitro, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{23}$, $R_{24}$, $R_{25}$, and $R_{26}$ may be the same or different and are each independently H, halogen, OH, amino, cyano, nitro, $C_1$-$C_4$alkyl, halo$C_1$-$C_4$alkyl, $C_1$-$C_4$alkoxy, halo$C_1$-$C_4$alkoxy or $C_3$-$C_4$cycloalkyl;

$R_{27}$ and $R_{28}$ may be the same or different and are each independently H, halogen, $C_1$-$C_4$alkyl, halo$C_1$-$C_4$alkyl, $C_1$-$C_4$alkoxy, halo$C_1$-$C_4$alkoxy, $C_1$-$C_4$alkylthio, halo$C_1$-$C_4$alkylthio, $C_3$-$C_4$cycloalkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{29}$ is $C_1$-$C_4$alkyl, halo$C_1$-$C_4$alkyl, $C_3$-$C_4$cycloalkyl, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{30}$ is H, cyano, halogen, $C_1$-$C_4$alkyl, halo$C_1$-$C_4$alkyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{31}$ is $C_1$-$C_4$alkyl, halo$C_1$-$C_4$alkyl, $C_3$-$C_4$cycloalkyl, $C_1$-$C_4$alkylsulfonyl, halo$C_1$-$C_4$alkylsulfonyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{32}$ is H, cyano, halogen, $C_1$-$C_4$alkyl, halo$C_1$-$C_4$alkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{33}$ and $R_{34}$ may be selected respectively from $C_1$-$C_4$alkyl, halo$C_1$-$C_4$alkyl, $C_3$-$C_4$cycloalkyl, $C_1$-$C_4$alkylcarbonyl, halo$C_1$-$C_4$alkylcarbonyl, $C_1$-$C_4$alkoxycarbonyl, halo$C_1$-$C_4$alkoxycarbonyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{35}$ and $R_{36}$ may be selected respectively from H, cyano, halogen, $C_1$-$C_4$alkyl, halo$C_1$-$C_4$alkyl, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$; and W is H, halogen, $C_1$-$C_4$alkyl, halo$C_1$-$C_4$alkyl, $C_3$-$C_4$cycloalkyl, $C_1$-$C_4$alkoxy, halo$C_1$-$C_4$alkoxy, or $C_1$-$C_4$alkylsulfonyl; and wherein the salt is formed from a compound represented by formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F, I-3G, I-4C, I-4F, or I-4G and hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid, or citric acid.

5. The substituted pyrazole compound containing pyrimidinyl according to claim 4 having formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F, I-3G, I-4C, I-4F, or I-4G, wherein $R_1$ is H, F, Cl, Br, I, CN, $NO_2$, $NH_2$, carboxyl, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $CH_2OCH_3$, $CH_2OCH_2CH_3$, or $CH_2OCH_2CF_3$;

$R_2$ is H, F, Cl, Br, I, CN, $NO_2$, $NH_2$, carboxyl, CHO, $CH_3$, $C_2H_5$, $OCH_3$, $OC_2H_5$, or $OCH_2CF_3$;

$R_3$ is H, OH, CHO, $COCH_3$, $COC_2H_5$, $COC_3H_7$, $COCF_3$, COPh, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CH_2CF_3$, $OCH_3$, $OC_2H_5$, $OCH_2CF_3$,

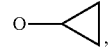

$SCH_3$, $SC_2H_5$, $CH_2CH=CH_2$, $CH_2C\equiv CH$, $SO_2CH_3$, $SO_2CH_2CH_3$, $SO_2CH_2CF_3$, $SO_2NHCH_3$, $SO_2NHC_2H_5$, $SO_2N(CH_3)_2$, $SO_2N(C_2H_5)_2$, $CONHSO_2CH_3$, $COOCH_3$, $COOC_2H_5$, $COOC_3H_7$-n, $COOC_3H_7$-i, $CONHCH_3$, $CON(CH_3)_2$, $COOCH=CH_2$, $COOC\equiv CH$, $SNHCH_3$, $SNHC_2H_5$, or $SN(CH_3)_2$;

$R_4$ and $R_5$ may be the same or different and are each independently H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, n-$C_3H_7O$, i-$C_3H_7O$, n-$C_4H_9O$, s-$C_4H_9O$, i-$C_4H_9O$, or t-$C_4H_9O$;

$R_6$ and $R_7$ may be the same or different and are each independently H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $OCH_3$, $OC_2H_5$, n-$C_3H_7O$, i-$C_3H_7O$, n-$C_4H_9O$, s-$C_4H_9O$, i-$C_4H_9O$, or t-$C_4H_9O$;

$R_8$ is H, CN, F, Cl, Br, I, $CH_3$, $C_2H_5$, or $CF_3$;

$R_9$ is H, CN, F, Cl, Br, I, $CH_3$, $C_2H_5$, or $CF_3$;

$R_{11}$ is F, Cl, Br, I, CN, $NH_2$, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, $COOCH_3$, $COOC_2H_5$, $CONH_2$, $CONHCH_3$, $CONHC_2H_5$, or $CON(CH_3)_2$;

n is selected from 0 to 5, when n is 0, the benzene ring is unsubstituted phenyl; when n is more than 1, $R_{11}$ may be the same or different;

$R_{14}$ is $CH_3$, $C_2H_5$, n-$C_3H_7$, i-$C_3H_7$, n-$C_4H_9$, s-$C_4H_9$, i-$C_4H_9$, t-$C_4H_9$, cyclopropyl, cyclobutyl, $CH_2F$, $CH_2Cl$, $CHF_2$, $CF_3$ or $CH_2CF_3$;

$R_{15}$ and $R_{16}$ may be the same or different and are each independently H, F, Cl, Br, I, $NH_2$, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{17}$, $R_{18}$, $R_{19}$, and $R_{20}$ may be the same or different and are each independently H, F, Cl, Br, I, CN, $NO_2$, $CH_3$, $CF_3$, $OCH_3$, or $OCF_3$;

$R_{21}$ and $R_{22}$ may be the same or different and are each independently H, F, Cl, Br, I, OH, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{23}$, $R_{24}$, $R_{25}$, and $R_{26}$ may be the same or different and are each independently H, F, Cl, Br, I, $NH_2$, CN, $NO_2$, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, or $OCH_2CF_3$;

$R_{27}$ and $R_{28}$ may be the same or different and are each independently H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, $CH_2CF_3$, $OCH_3$, $OCH_2CH_3$, n-$C_3H_7O$, i-$C_3H_7O$, n-$C_4H_9O$, s-$C_4H_9O$, i-$C_4H_9O$, t-$C_4H_9O$, $OCF_3$, $OCH_2CF_3$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{29}$ is $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $SO_2CH_3$, $SO_2CH_2CH_3$, $COCH_3$, $COC_2H_5$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{30}$ is H, CN, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{31}$ is $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $SO_2CH_3$, $SO_2CH_2CH_3$, $COCH_3$, $COC_2H_5$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{32}$ is H, CN, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{33}$ and $R_{34}$ may be selected respectively from $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, cyclopropyl, $COCH_3$, $COC_2H_5$, $COOCH_3$, $COOC_2H_5$, $COOCH_2CF_3$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$;

$R_{35}$ and $R_{36}$ may be selected respectively from H, CN, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CF_3$, $CCl_3$, $CF_2Cl$, $CFCl_2$, unsubstituted or further substituted (hetero)aryl, (hetero)arylmethyl, (hetero)arylcarbonyl, (hetero)arylmethylcarbonyl, or (hetero)aryloxycarbonyl by 1 to 5 $R_{11}$; and W is H, F, Cl, Br, I, $CH_3$, $C_2H_5$, n-$C_3H_7$, i-$C_3H_7$, n-$C_4H_9$, s-$C_4H_9$, i-$C_4H_9$, t-$C_4H_9$, $CH_2F$, $CH_2Cl$, $CHF_2$, $CF_3$, $CH_2CF_3$, $OCH_3$, $OC_2H_5$, $SCH_3$, $SC_2H_5$, $SO_2CH_3$, or $SO_2CH_2CH_3$; and wherein the salt is formed from a compound represented by formula I-1A, I-1B, I-1C, I-1D, I-1E, I-1F, I-1G, I-1H, I-1I, I-1J, I-1K, I-1L, I-1M, I-1N, I-2A, I-2B, I-2C, I-2D, I-2E, I-2F, I-2G, I-3A, I-3B, I-3C, I-3D, I-3E, I-3F, I-3G, I-4C, I-4F, or I-4G and hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid, or citric acid.

6. The substituted pyrazole compound containing pyrimidinyl according to claim 5 having formula I-1C, I-1F, I-1G, I-2C, I-2F, I-2G, I-4C, I-4F, or I-4G, wherein $R_1$ is H, F, Cl, Br, I, $CH_3$, $C_2H_5$, or $CHF_2$;

$R_2$ is H, F, Cl, Br, I, $NO_2$, $NH_2$, CHO, $CH_3$, $C_2H_5$, $OCH_3$, or $OC_2H_5$;

$R_3$ is H, $CH_3$, $COCH_3$, $COCF_3$, $OCH_3$, $SCH_3$, $CH_2CH=CH_2$, $SO_2CH_3$, $SO_2NHCH_3$, $SO_2N(CH_3)_2$, $COOCH_3$, $CONHCH_3$, $CON(CH_3)_2$, $SNHCH_3$, or $SN(CH_3)_2$;

$R_4$ and $R_5$ may be the same or different and are each independently H, F, Cl, Br, or $CH_3$;

$R_6$ and $R_7$ are H;

$R_8$ is H;

$R_9$ is H;

$R_{11}$ is F, Cl, Br, I, CN, $NO_2$, $CH_3$, $CF_3$, $OCH_3$, or $OCF_3$;

n is selected from 0 to 5, when n is 0, the benzene ring is unsubstituted phenyl; when n is more than 1, $R_{11}$ may be the same or different;

$R_{23}$, $R_{24}$, $R_{25}$, and $R_{26}$ may be the same or different and are each independently H, F, Cl, Br, I, or $CH_3$;

$R_{27}$ and $R_{28}$ may be the same or different and are each independently H, F, Cl, Br, or I; and W is H, F, Cl, Br, I, or $CH_3$; and wherein the salt is formed from a compound represented by formula I-1C, I-1F, I-1G, I-2C, I-2F, I-2G, I-4C, I-4F or I-4G and hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid, or citric acid.

7. The substituted pyrazole compound containing pyrimidinyl according to claim 5 having formula I-1C, I-1F, I-1G, I-2C, I-2G, I-4C, I-4F, or I-4G, wherein $R_1$ is F, Cl, Br, I, $CH_3$, $C_2H_5$, or $CHF_2$;

$R_2$ is F, Cl, Br, I, $NO_2$, $NH_2$, CHO, $CH_3$, or $OCH_3$;

$R_3$ is H, $CH_3$, $COCH_3$, $OCH_3$, $CH_2CH=CH_2$, $SO_2CH_3$, $COOCH_3$, $CONHCH_3$, $CON(CH_3)_2$, or $SN(CH_3)_2$;

$R_4$ and $R_5$ may be the same or different and are each independently H or $CH_3$;

$R_6$ and $R_7$ are H;

$R_8$ is H;

$R_9$ is H;

$R_{11}$ is F, Cl, Br, I, CN, $NO_2$, $CH_3$, $CF_3$, $OCH_3$, or $OCF_3$;

n is selected from 1 to 5, when n is more than 1, $R_{11}$ may be the same or different;

$R_{23}$, $R_{24}$, $R_{25}$, and $R_{26}$ are H;

$R_{27}$ is H;

$R_{28}$ is Cl; and

W is H, F, Cl, Br, or I; and wherein the salt is formed from a compound represented by formula I-1C, I-1F, I-1G, I-2C, I-2G, I-4C, I-4F or I-4G and hydrochloric acid, sulfuric acid, phosphoric acid, formic acid, acetic acid, trifluoroacetic acid, oxalic acid, methylsulfonic acid, p-toluenesulfonic acid, benzoic acid, alizaric acid, maleic acid, fumaric acid, sorbic acid, malic acid, or citric acid.

8. A preparation method of the substituted pyrazole compound containing pyrimidinyl according to claim 3, wherein the preparation method of the formula I-1 is as follows:

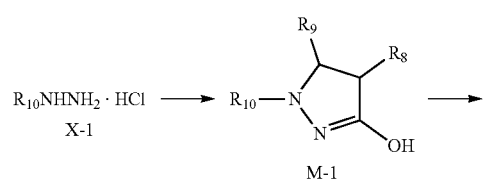

-continued

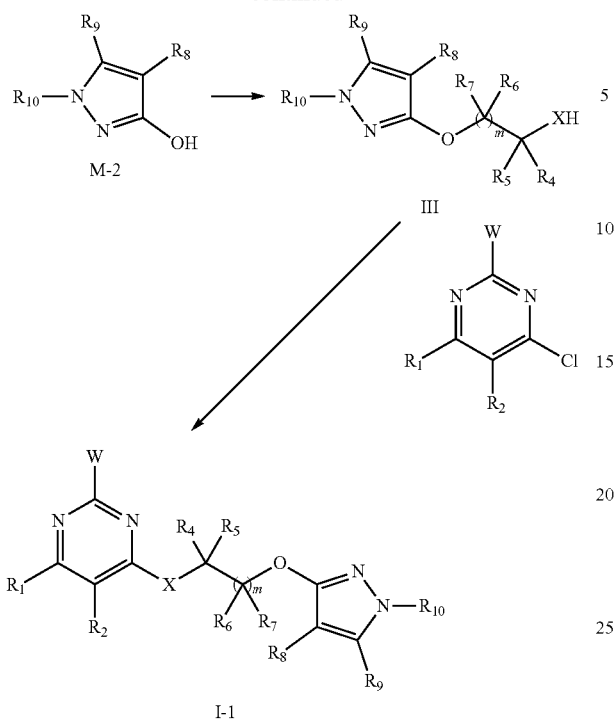

the preparation method of the formula I-2 is as follows:

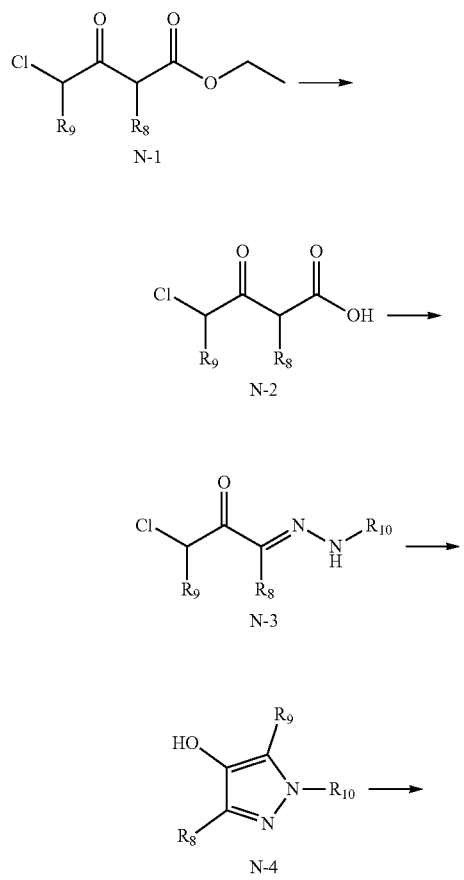

-continued

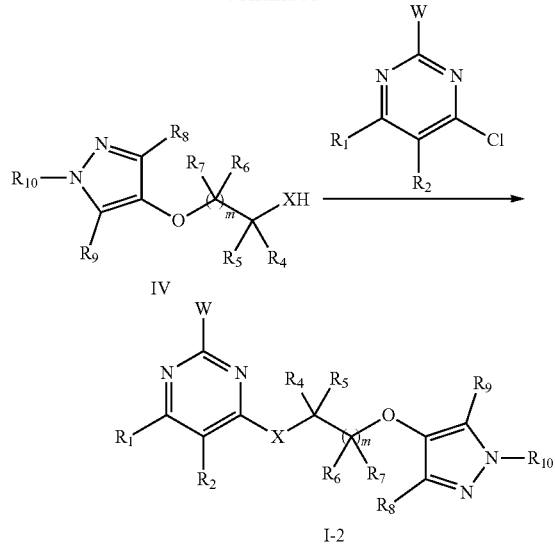

the preparation method of the formula I-3 is as follows:

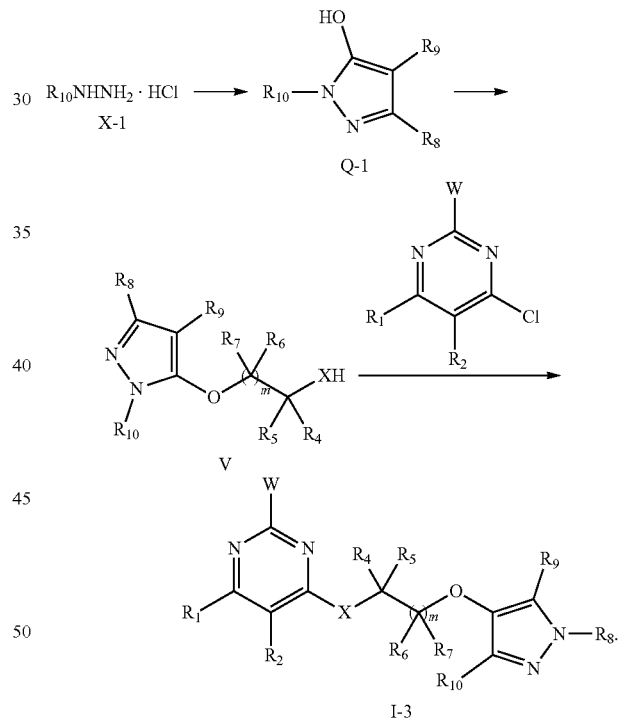

9. A composition comprising a compound according to claim 1.

10. A fungicide, insecticide, or acaricide composition comprising a compound according to claim 1 as an active ingredient and an acceptable carrier.

11. The fungicide, insecticide, or acaricide composition of claim 10, wherein the amount of the compound in the composition is 0.1-99 wt % of the total weight of the composition.

12. A method of making a fungicide, insecticide, or acaricide, the method comprising adding an amount of a compound according to claim 1 to a composition, wherein the amount of the compound in the composition is 0.1-99 wt % of the total weight of the composition.

13. A composition comprising a compound according to claim 4.

14. A fungicide, insecticide, or acaricide composition comprising a compound according to claim 4 as an active ingredient and an acceptable carrier.

15. The fungicide, insecticide, or acaricide composition of claim 14, wherein the amount of the compound in the composition is 0.1-99 wt % of the total weight of the composition.

16. A method of making a fungicide, insecticide, or acaricide, the method comprising adding an amount of a compound according to claim 4 to a composition, wherein the amount of the compound in the composition is 0.1-99 wt % of the total weight of the composition.

* * * * *